United States Patent
Shturman et al.

[19]

[11] Patent Number: 6,129,734
[45] Date of Patent: *Oct. 10, 2000

[54] ROTATIONAL ATHERECTOMY DEVICE WITH RADIALLY EXPANDABLE PRIME MOVER COUPLING

[75] Inventors: Leonid Shturman, Minneapolis, Minn.; Leonid Volkov, Moscow, Russian Federation

[73] Assignee: Shturman Cardiology Systems, Inc., Minneapolis, Minn.

[ * ] Notice: This patent is subject to a terminal disclaimer.

[21] Appl. No.: 08/957,942

[22] Filed: Oct. 27, 1997

Related U.S. Application Data

[63] Continuation-in-part of application No. 08/792,101, Jan. 31, 1997, Pat. No. 5,779,722, which is a continuation-in-part of application No. 08/785,991, Jan. 21, 1997, Pat. No. 5,893,857.

[51] Int. Cl.[7] .................................................. A61B 17/22
[52] U.S. Cl. .............................. 606/159; 606/180; 604/22
[58] Field of Search .............................. 606/1, 159, 167, 606/170, 171, 184, 185, 180; 604/19, 22

[56] References Cited

U.S. PATENT DOCUMENTS

| | | |
|---|---|---|
| 1,851,146 | 3/1932 | Banker . |
| 3,712,438 | 1/1973 | Roddy et al. . |
| 3,937,222 | 2/1976 | Banko . |
| 4,679,557 | 7/1987 | Opie et al. . |
| 4,857,046 | 8/1989 | Stevens et al. . |
| 4,926,986 | 5/1990 | Noel . |
| 5,501,694 | 3/1996 | Ressemann et al. . |
| 5,584,843 | 12/1996 | Wulfman et al. . |
| 5,681,336 | 10/1997 | Clement et al. . |

FOREIGN PATENT DOCUMENTS

| | | |
|---|---|---|
| 244 058 | 11/1987 | European Pat. Off. . |
| 0 321 319 | 6/1989 | European Pat. Off. . |
| 761 398 | 9/1933 | France . |
| 1000163 | 10/1996 | Netherlands . |
| WO 94/12132 | 6/1994 | WIPO . |
| WO 96/37153 | 11/1996 | WIPO . |
| WO 97/14470 | 4/1997 | WIPO . |

*Primary Examiner*—Glenn K. Dawson
*Attorney, Agent, or Firm*—Fredrikson & Byron, P.A.

[57] ABSTRACT

A rotatable atherectomy device having an exchangeable drive shaft cartridge and a rotatable prime mover coupling. The cartridge has a rotatable drive shaft socket carried by a carriage. The coupling radially expands during rotation such that it interlocks with the socket to drive a tissue removal implement on the end of a drive shaft attached to the cartridge. Upon slow or no rotation of the socket, the coupling disengages from the socket to allow for exchange of the cartridge.

157 Claims, 66 Drawing Sheets

ROTATIONAL ATHERECTOMY DEVICE WITH RADIALLY EXPANDABLE PRIME MOVER COUPLING

The present application is a continuation-in-part of U.S. patent application Ser. No. 08/792,101, filed 31 Jan. 1997 and now U.S. Pat. No. 5,779,722, which is, in turn, a continuation-in-part of U.S. patent application Ser. No. 08/785,991, filed 21 Jan. 1997 and now U.S. Pat. No. 5,893,857.

FIELD OF THE INVENTION

The invention relates to devices and methods for removing tissue from body passageways, such as removal of atherosclerotic plaque from arteries, utilizing a rotational atherectomy device. In particular, the invention relates to improvements in a rotational atherectomy device having an exchangeable drive shaft. This invention may also have additional uses unrelated to atherectomy devices.

BACKGROUND OF THE INVENTION

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (Auth), a rotating burr covered with an abrasive cutting material, such as diamond grit (diamond particles or dust), is carried at the distal end of a flexible, rotatable drive shaft.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

U.S. Pat. No. 5,314,407 (Auth) shows details of a type of handle which may be used in conjunction with rotational atherectomy devices of the type shown in the Auth '134 and Shturman '438 patents. A handle of the type shown in the Auth '407 patent has been commercialized by Heart Technology, Inc. (Redmond, Wash.), now owned by Boston Scientific Corporation (Natick, Mass.) in the rotational atherectomy device sold under the trademark Rotablator®. The handle of the Rotablator® device includes a variety of components, including a compressed gas driven turbine, a mechanism for clamping a guide wire extending through the drive shaft, portions of a fiber optic tachometer, and a pump for pumping saline through the drive shaft.

The connection between the drive shaft (with its associated burr) and the turbine in the Rotablator® device is permanent; yet, frequently it is necessary to use more than one size burr during an atherectomy procedure. That is, often a smaller size burr is first used to open a stenosis to a certain diameter, and then one or more larger size burrs are used to open the stenosis further. Such use of multiple burrs of subsequently larger diameter is sometimes referred to as a "step up technique" and is recommended by the manufacturer of the Rotablator® device. In the multiple burr technique it is necessary to use a new Rotablator® device for each such successive size burr. Accordingly, there is a need for an atherectomy system that would permit a physician to use only one handle throughout an entire procedure and to attach to such handle an appropriate drive shaft and tissue removing implement (e.g., a burr) to initiate the procedure and then exchange the drive shaft and the tissue removing implement for a drive shaft having a tissue removing implement of a different size or even a different design.

A subsequent version of the Rotablator® has been introduced with the ability to exchange a flexible distal portion of the drive shaft together with a burr for another distal portion of a drive shaft having a different size burr. Technical details of such a system are contained in international patent application No. WO 96/37153. This system utilizes a flexible drive shaft having a connect/disconnect feature allowing the physician to disconnect the exchangeable distal portion of the flexible drive shaft together with the burr from the flexible proximal portion of the drive shaft which is connected to the turbine of the handle, thus permitting the burr size to be changed without discarding the entire atherectomy unit. Each exchangeable drive shaft portion is disposed within its own exchangeable catheter and catheter housing. The flexible proximal portion of the drive shaft in this system is permanently attached to the turbine and is not exchanged. This system has been commercialized by Boston Scientific under the trademark Rotalink System™. While the Rotalink System™ does permit one to change the burr size, the steps required to actually disconnect the exchangeable portion of the drive shaft and replace it with another exchangeable portion of the drive shaft are quite involved and require relatively intricate manipulation of very small components.

First, a catheter housing must be disconnected from the handle and moved distally away from the handle to expose portions of both the proximal and distal sections of the flexible drive shaft which contain a disconnectable coupling. This coupling is disconnected by sliding a lock tube distally, permitting complementary lock teeth on the proximal and distal portions of the flexible drive shaft to be disengaged from each other. A similar flexible distal drive shaft portion with a different burr may then be connected to the flexible proximal portion of the drive shaft. To accomplish such assembly, the lock tooth on the proximal end of the distal replacement portion of the drive shaft must first be both longitudinally and rotationally aligned with the complementary lock tooth at the distal end of the proximal portion of the drive shaft. Since the flexible drive shaft typically is less than 1 mm in diameter, the lock teeth are similarly quite small in size, requiring not insignificant manual dexterity and visual acuity to properly align and interlock the lock teeth. Once the lock teeth have been properly interlocked with each other, the lock tube (also having a very small diameter) is slid proximally to secure the coupling. The catheter housing must then be connected to the handle housing.

While this system does permit one to exchange one size burr (together with a portion of the drive shaft) for a burr of another size, the exchange procedure is not an easy one and must be performed with considerable care. The individual performing the exchange procedure must do so while wearing surgical gloves to protect the individual from the blood of the patient and to maintain the sterility of the elements of the system. Surgical gloves diminish the tactile sensations of the individual performing the exchange procedure and therefore make such exchange procedure even more difficult.

Accordingly, it would be desirable to have an atherectomy device permitting easier attachment and/or exchange of the drive shaft and its tissue removing implement.

SUMMARY OF THE INVENTION

One embodiment of the present invention provides a rotational atherectomy device which includes an exchangeable drive shaft cartridge and a rotatable, radially expandable prime mover coupling. The exchangeable drive shaft cartridge desirably includes a rotatable drive shaft socket carried by a drive shaft carriage; a longitudinally extendable tube extending distally from the drive shaft carriage; an elongated catheter having a proximal end portion which is operatively connected to and may be generally aligned with a distal end portion of the longitudinally extendable tube; and a rotatable flexible drive shaft. The flexible drive shaft has proximal, intermediate and distal portions, the proximal portion being attached to the drive shaft socket, the intermediate portion being disposed primarily within the longitudinally extendable tube and the catheter, and the distal portion extending distally from the catheter and having a tissue removal implement. The prime mover coupling desirably is carried by a prime mover carriage and is connected to a prime mover for rotation therewith.

The drive shaft socket of this embodiment of the invention is sized to receive a length of the prime mover coupling therein such that the prime mover coupling does not effectively engage an interior surface of the drive shaft socket when the coupling is not rotating. However, the prime mover coupling radially expands to effectively engage the socket upon sufficiently rapid rotation of the prime mover, causing the socket and the drive shaft to rotate together with the prime mover coupling and the prime mover.

As a result, when the prime mover is not rotating, the drive shaft is disconnected from the prime mover, thereby permitting the exchangeable drive shaft cartridge to be replaced by another exchangeable drive shaft cartridge. Although this design permits replacement of the exchangeable drive shaft cartridge, it should be recognized that a user may choose not to actually replace one exchangeable drive shaft cartridge with another during a single procedure, e.g. where a single tissue removal implement achieves the clinical objective.

In one preferred embodiment, the prime mover coupling includes a coupling base and at least two flexible pins, each pin being anchored adjacent one end thereof to the coupling base and having another end which is free to deflect radially outwardly to engage the drive shaft socket when the prime mover is rotated. These flexible pins may be adapted to deflect radially outwardly into frictional engagement with the interior engagement surface of the drive shaft socket in response to rotation of the prime mover.

In a preferred embodiment, the drive shaft carriage and the prime mover carriage are longitudinally moveable with respect to one another from an operational position wherein a length of the prime mover coupling is received within the drive shaft socket to a non-operational position wherein the prime mover coupling is withdrawn from the drive shaft socket. In the operational position, the drive shaft carriage and the prime mover carriage can be interconnected to move together as a unit to move the drive shaft and its tissue removal implement along a vascular lumen of a patient's body.

In a further embodiment, the rotational atherectomy device includes a handle which carries the prime mover carriage and which is adapted to releasably hold the drive shaft cartridge. The handle may comprise a distal portion adapted to releasably hold the drive shaft cartridge, a proximal portion carrying the prime mover carriage, and an elongated rod connecting the distal and proximal portions of the handle to one another.

A preferred embodiment includes a flexible fluid supply tubing attached to the exchangeable drive shaft cartridge. The flexible fluid supply tubing may be in fluid communication with a drive shaft lumen of the drive shaft cartridge, the drive shaft lumen being defined by a lumen of the catheter and a lumen of the longitudinally extendable tube. Optimally, the drive shaft lumen includes a reduced inner diameter segment, the reduced inner diameter segment being positioned proximally of where the fluid supply tubing delivers fluid to the drive shaft lumen, thereby reducing flow of fluid proximally along the drive shaft lumen.

In yet another embodiment, the prime mover carriage carries a coupling shield which restricts radial expansion of the prime mover coupling upon rotation of the prime mover when the prime mover coupling is not properly received within the drive shaft socket. This coupling shield may be carried by the prime mover coupling and can be moved away from a distal end of the coupling to permit the coupling to be properly received within the drive shaft socket so the coupling can engage the socket upon rotation of the prime mover.

An alternative embodiment of the invention provides a simplified system for releasably connecting a drive shaft to a prime mover. This system also includes an exchangeable drive shaft cartridge and a rotatable, radially expandable prime mover coupling. This embodiment of the invention may provide a more cost-efficient approach in connection with medical devices and may be used successfully in fields unrelated to medical devices. The exchangeable drive shaft cartridge desirably includes rotatable drive shaft socket carried by a drive shaft carriage and a rotatable drive shaft having a proximal portion attached to the drive shaft socket. The prime mover coupling is connected to a prime mover for rotation therewith, the prime mover coupling comprising a coupling base and at least two flexible pins, each pin being anchored adjacent one end thereof to the coupling base and having another end which is free to deflect radially outwardly to engage the drive shaft socket when the prime mover is rotated. The drive shaft socket of this embodiment is sized to receive the free end portions of the pins of the prime mover coupling therein such that the pins do not contact the interior surface of the drive shaft socket when the coupling is not rotating, but the free end portions of the pins deflect into frictional engagement with the socket upon sufficiently rapid rotation of the prime mover, causing the socket and the drive shaft to rotate together with the prime mover coupling and the prime mover. As a result, when the prime mover is not rotating, the drive shaft is disconnected from the prime mover, thereby permitting the exchangeable drive shaft cartridge to be replaced by another exchangeable drive shaft cartridge, if so desired.

The present invention also contemplates a method of removing tissue from passageways in a human body or removing a variety of materials from various cavities or passageways. This method may be used in a variety of industrial applications to clean or enlarge passageways, as well as to clean or form a variety of cavities. First, a tissue removal device is provided. The tissue removal device has an exchangeable drive shaft cartridge and a rotatable, radially expandable prime mover coupling. The exchangeable drive shaft cartridge includes a rotatable drive shaft socket carried by a drive shaft carriage; a longitudinally extendable tube extending distally from the drive shaft carriage; an elongated catheter having a proximal end portion which is operatively connected to a distal end portion of the longitudinally extendable tube; and a rotatable flexible drive shaft having proximal, intermediate and distal portions, the proximal portion being attached to the drive shaft socket, the intermediate portion being disposed primarily within the longitudinally extendable tube and the catheter, and the distal portion extending distally from the catheter and having a tissue removal implement. The prime mover coupling is carried by a prime mover carriage and connected to a prime mover for rotation therewith.

In accordance with this method, a length of the prime mover coupling is positioned within the drive shaft socket such that the prime mover coupling does not effectively engage an interior surface of the drive shaft socket. The prime mover coupling is then rotated at a speed sufficient to cause it to radially expand to effectively engage the drive shaft socket, causing the socket and the drive shaft to rotate together with the prime mover coupling and the prime mover. Rotation of the prime mover is then stopped, thereby disconnecting the drive shaft from the prime mover. If so desired, once the drive shaft is so disconnected from the prime mover, the exchangeable drive shaft cartridge can be replaced with another exchangeable drive shaft cartridge.

In atherectomy applications, the flexible drive shaft and the catheter are advanced over a guide wire into a body passageway of interest. The rest of the assembled device typically is also advanced over the guide wire, but remains outside the patient's body. The prime mover and the prime mover coupling are rotated at a speed sufficient to cause the prime mover coupling to radially expand to effectively engage the drive shaft socket, causing the socket and the drive shaft to rotate together with the prime mover coupling and the prime mover. The rotating flexible drive shaft and its tissue removal implement are advanced against the material to be removed. When the desired amount of material has been removed, the prime mover may be stopped or slowed down and the flexible drive shaft and the catheter are withdrawn from the patient's body. When rotation of the prime mover is stopped, the drive shaft is disconnected from the prime mover. If so desired, once the drive shaft is so disconnected from the prime mover, the exchangeable drive shaft cartridge can be replaced with another exchangeable drive shaft cartridge having a tissue removal implement of different size or even different design and the procedure spelled out above may be repeated on the same or a different passageway.

It should be noted that, for some medical applications, and even for some atherectomy applications, the use of a guide wire may not be necessary for some or all of the procedure. In some applications, special guiding catheters may be employed together with or instead of a guide wire.

In industrial applications, the catheter around the drive shaft may not be needed and there may be no need for either a guide wire or a guiding catheter. For other specific applications (both medical and non-medical), other components may be omitted from the exchangeable drive shaft cartridge or the prime mover coupling. For example, there may be no need for the longitudinally extendable tube.

DETAILED DESCRIPTION OF THE PREFERRED EMBODIMENTS

Figure 1:
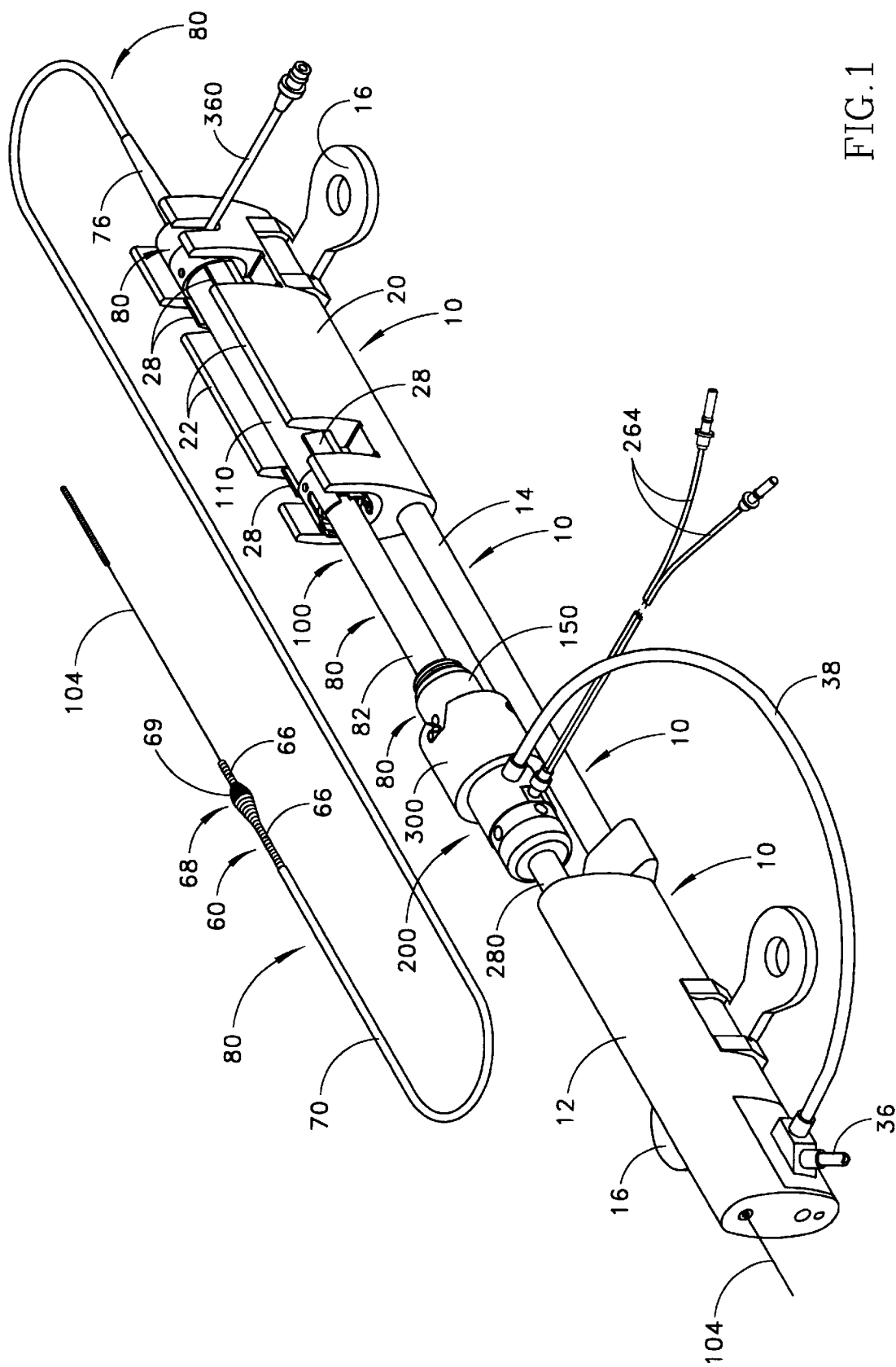
FIG. 1 is a perspective view of one embodiment of a rotational atherectomy device of the present invention showing the exchangeable drive shaft cartridge attached to the handle and illustrating the drive shaft carriage and the prime mover carriage interconnected to move together as a unit.

FIG. 1 illustrates in perspective view one embodiment of an atherectomy device of the invention. The device desirably includes a handle 10. The handle 10 has a proximal portion 12 which carries a prime mover carriage 200, a distal portion 20 adapted to releasably hold an exchangeable drive shaft cartridge 80, and an intermediate portion 14 which serves to connect the proximal and distal portions of the handle to one another.

The prime mover carriage 200 is longitudinally moveable with respect to the handle 10 by being connected to a telescoping tube 280 which is slidably received in the proximal portion 12 of the handle 10. The prime mover carriage 200 carries a prime mover coupling 330 which is connected to a prime mover for rotation therewith. (The prime mover coupling 330 and the prime mover are not seen in FIG. 1, but are discussed below in connection with FIGS. 26 and 36–39, for example.)

The exchangeable drive shaft cartridge 80 includes a drive shaft carriage 150, a longitudinally extendable tube 100 extending distally from the drive shaft carriage, an elongated catheter 70 operatively connected to a distal end portion of the longitudinally extendable tube, and a rotatable flexible drive shaft 60. The flexible drive shaft 60 is desirably rotatable over a guide wire 104 and includes a proximal portion 62, an intermediate portion 64 and a distal portion 66. The proximal portion 62 of the drive shaft 60 is attached to a drive shaft socket 180 carried by the drive shaft carriage 150. (The proximal portion 62 of the drive shaft 60 and the drive shaft socket 180 are not shown in FIG. 1, but are discussed below in connection with FIGS. 24 and 25, for example.) The intermediate portion 64 of the drive shaft 60 is disposed primarily within the longitudinally extendable tube 100 and the catheter 70 and therefore is not visible in FIG. 1. The distal portion 66 of the drive shaft extends distally from the catheter 70 and includes a tissue removal implement 68. The tissue removal implement in the illustrated embodiment comprises an enlarged diameter section of the drive shaft which has a generally conical proximal portion and a generally convex distal portion. The convex distal portion is covered with an abrasive material to define an abrasive segment 69 of the drive shaft. (Such a tissue removal implement is described in U.S. patent application Ser. No. 08/679,470, filed 15 Jul. 1996.) It should be understood that any suitable tissue removal implement 68 may be used, including an eccentric tissue removal implement (such as is described in U.S. patent application Ser. No. 08/911,586, filed 14 Aug. 1997) or the diamond-coated burr proposed by Auth in U.S. Pat. No. 4,990,134.

In FIG. 1, the drive shaft carriage 150 and the prime mover carriage 200 are interconnected so they can be moved together as a unit.

As is described in more detail below (e.g., in connection with FIGS. 36–39), the prime mover coupling 330 of the prime mover carriage 200 is adapted to effectively engage the drive shaft socket 180 of the drive shaft carriage 150 upon sufficiently rapid rotation of the prime mover. This will, in turn, cause the drive shaft socket 180 and the drive shaft 60 to rotate together with the prime mover coupling 330 and the prime mover. However, when the prime mover is not rotating, the prime mover coupling 330 becomes disengaged from the drive shaft socket 180, thereby permitting the drive shaft carriage 150 to be disconnected from the prime mover carriage 200. As a result, one exchangeable drive shaft cartridge 80 can be disconnected from the distal portion 20 of the handle 10 and replaced by another exchangeable drive shaft cartridge.

The exchangeable drive shaft cartridge 80 comprises a generally tubular housing 110. In a preferred embodiment, the distal portion 20 of the handle 10 includes at least one complementary clamp 28 for releasably holding the tubular housing 110 of the drive shaft cartridge 80 within a longitudinally extending groove 24 which is formed in the distal portion 20 of the handle. In this embodiment, the longitudinally extending groove 24 (better seen in FIGS. 13 and 14, for example) is upwardly open and is defined by a pair of opposing walls 22.

As is described in more detail below (e.g., in connection with FIGS. 24 and 25), the longitudinally extendable tube 100 includes outer 82 and inner 90 telescoping tubes. The outer telescoping tube 82 is connected to the drive shaft carriage 150 and the inner telescoping tube 90 is connected to a distal end piece (130 in FIG. 24, for example) of the tubular housing 110. The outer telescoping tube 82 is slidably received in an elongated annular space 120 defined between the inner surface of the tubular housing 110 and an outer surface of the inner telescoping tube 90.

Figure 2:
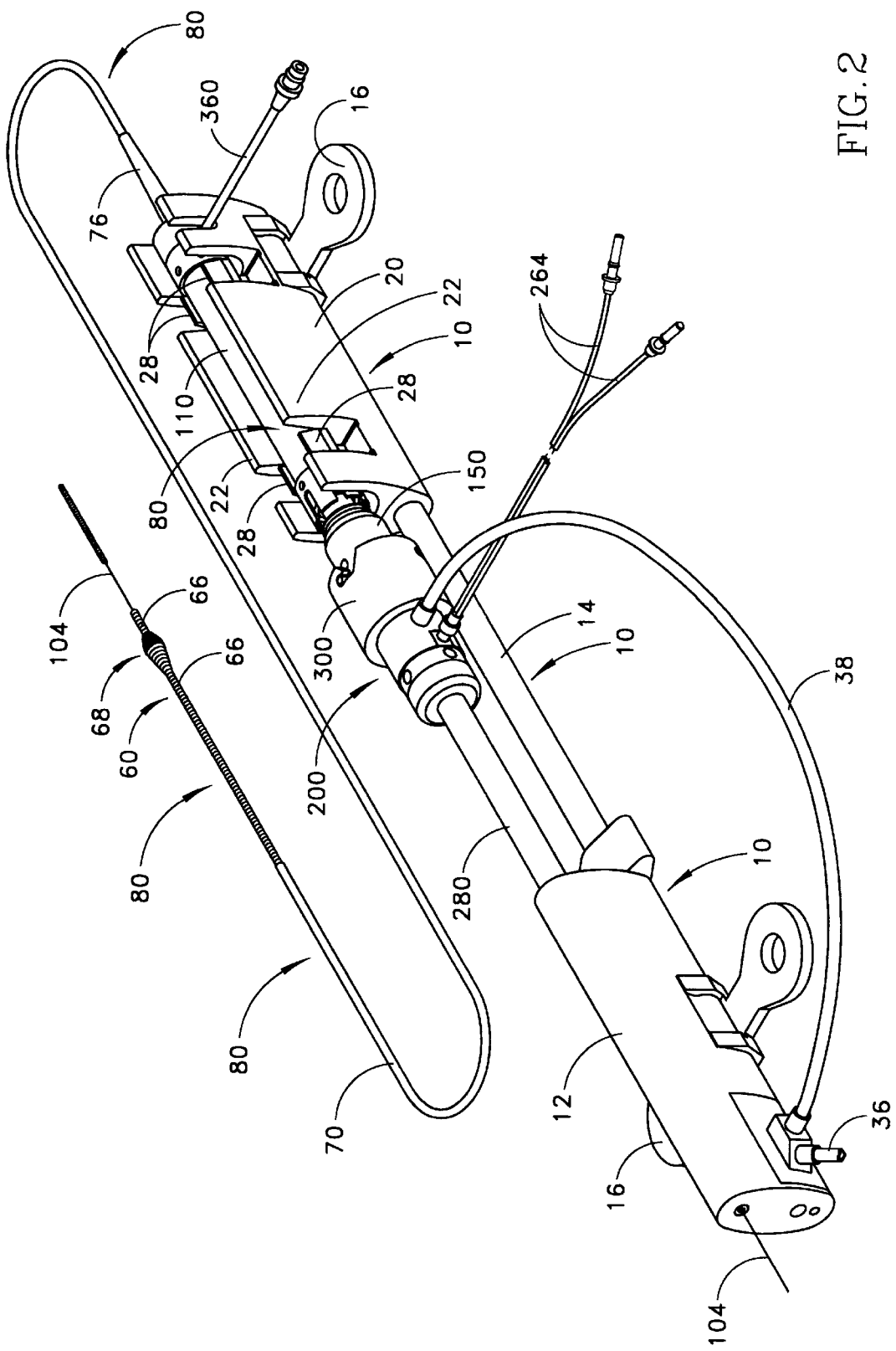
FIG. 2 is a perspective view of the device of FIG. 1 with the interconnected carriages moved distally toward a position where the drive shaft carriage becomes locked in a position which is convenient for detaching the drive shaft cartridge from the handle.

FIGS. 2–10 schematically illustrate a preferred sequence for disconnecting the drive shaft carriage 150 from the prime mover carriage 200. First, as shown in FIG. 2, the interconnected carriages 150 and 200 are moved forward to shorten the longitudinally extendable tube 100 so that its telescoping tubular components are not damaged when the drive shaft cartridge 80 is removed from the longitudinally extending groove 24 in the distal portion 20 of the handle 10.

FIGS. 3–6 illustrate a preferred embodiment wherein the tubular housing 110 and the drive shaft carriage 150 carry complementary fittings for releasably locking the drive shaft carriage 150 to the tubular housing 110 when a majority of the length of the outer telescoping tube 82 is received within the tubular housing 110 of the drive shaft cartridge 80. In a preferred embodiment, these complementary fittings comprise at least one tab 114 carried by one of the tubular housing 110 and the drive shaft carriage 150 and a flange 154 carried by the other one of the tubular housing 110 and the drive shaft carriage 150.

In the embodiment seen in FIGS. 3–6, the proximal end of the tubular housing 110 is provided with a plurality of proximally extending resilient tabs 114 which have inwardly-extending shoulders 116 adjacent their proximal ends. If so desired, the tabs may all be integrally formed with an annular proximal collar 112 which is attached to the proximal end of the tubular housing 110. The drive shaft carriage 150 is provided with a radially outwardly extending flange 154. A groove 156 may be provided proximally of the flange 154 for receiving the shoulders 116 of the resilient tabs 114 of the tubular housing 110.

Equivalently, the flange 154 may be carried not by the drive shaft carriage 150, as shown in the illustrated embodiment, but instead by the outer telescoping tube 82. This will permit the user to releasably interlock the outer telescoping tube 82 and the tubular housing 110, thereby protecting the telescoping tubes (82 and 90) of the longitudinally extendable tube 100 from damage when the drive shaft cartridge 80 is removed from the longitudinally extending groove 24 in the distal portion 20 of the handle 10.

Figure 3:
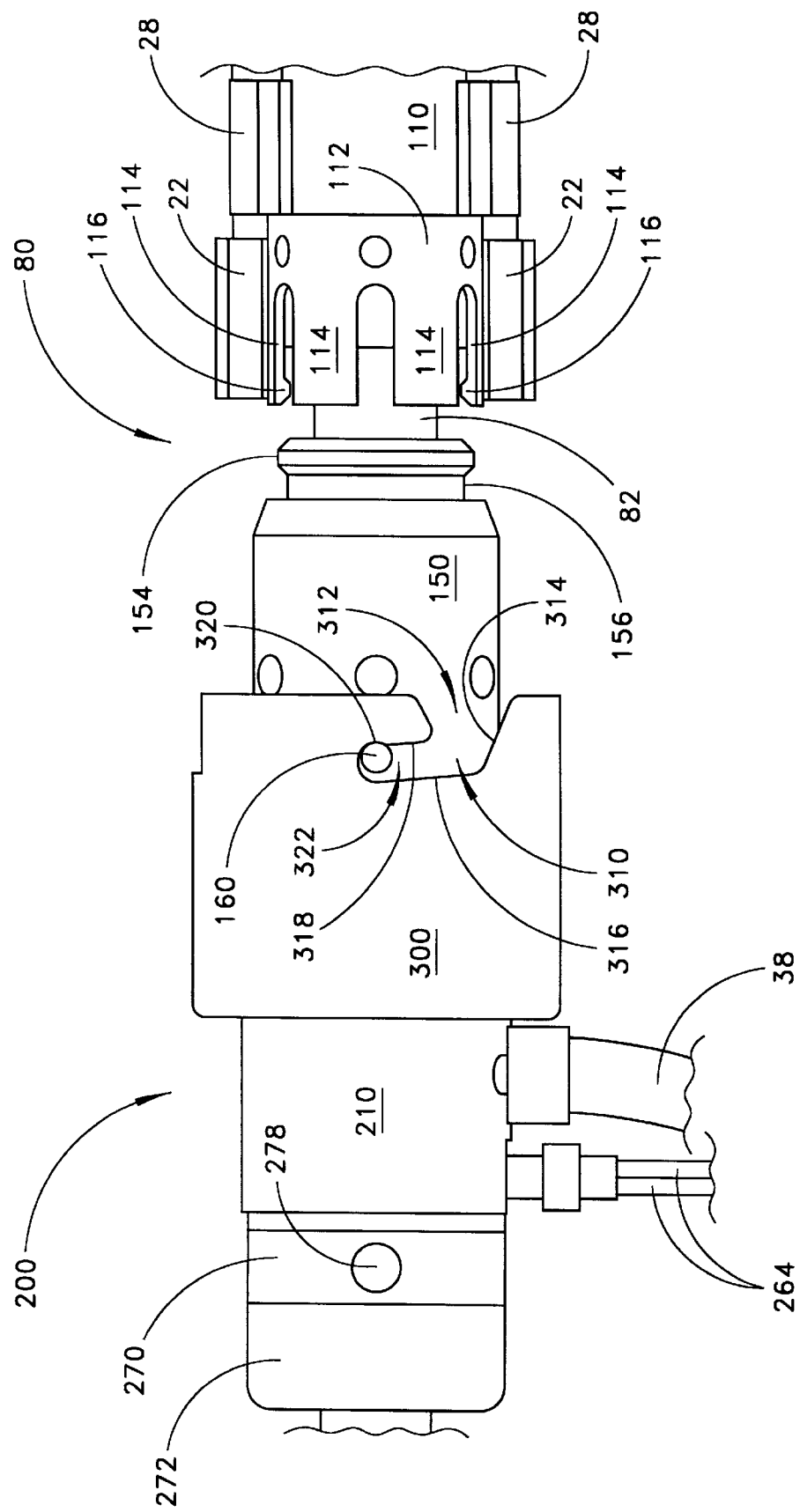
FIG. 3 is a top view of a broken-away portion of the device of FIG. 2, illustrating the interlocking elements of the exchangeable drive shaft cartridge.
Figure 4:
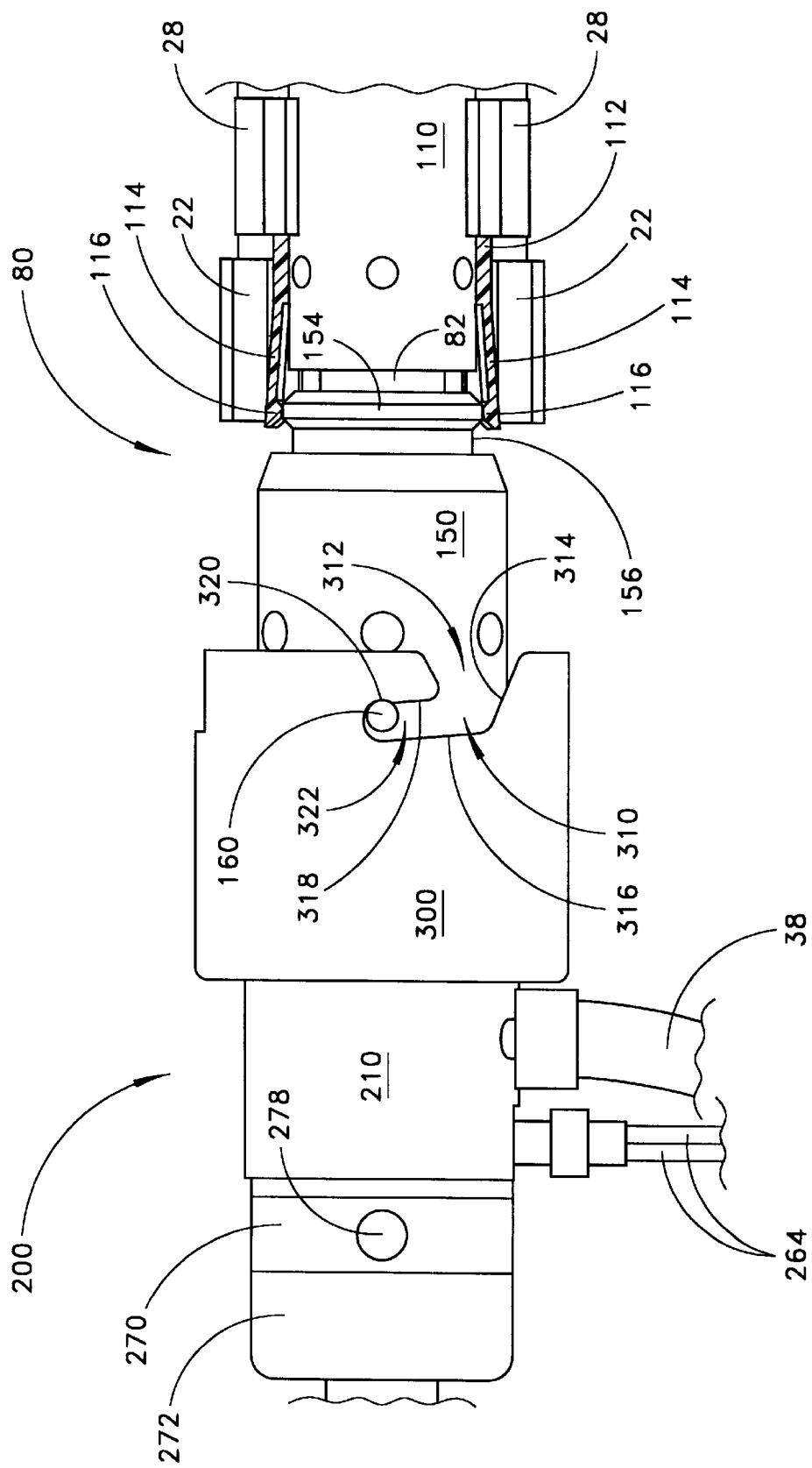
FIG. 4 is a partially cross sectional view similar to FIG. 3 showing an intermediate step in moving the drive shaft carriage to a position where the interlocking elements of the drive shaft cartridge become interlocked.
Figure 5:
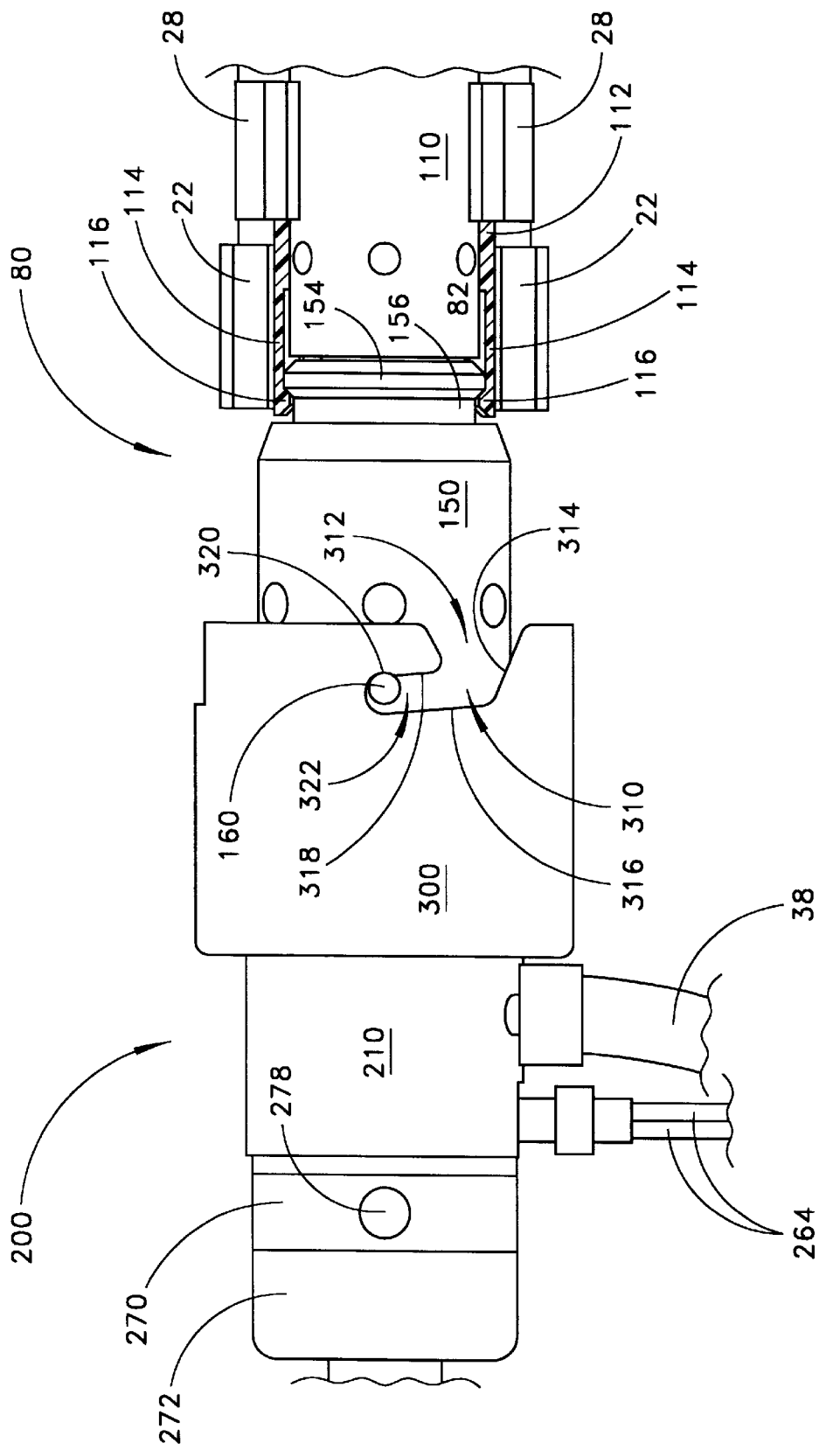
FIG. 5 is a partially cross sectional view similar to FIGS. 3 and 4 showing the interlocking elements of the exchangeable drive shaft cartridge in their interlocked position.
Figure 6:
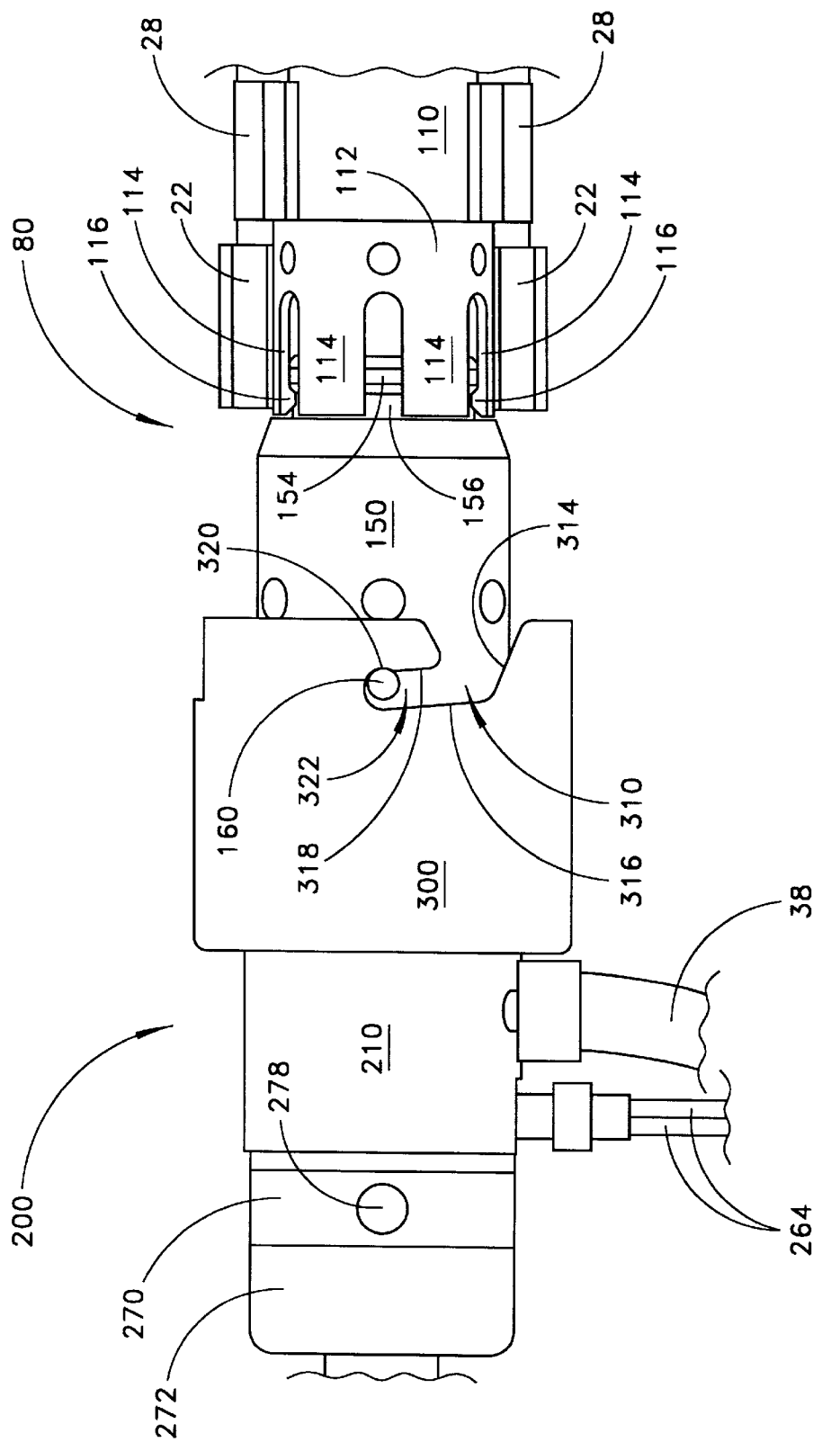
FIG. 6 is a view similar to FIG. 5, but showing the interlocking elements of the exchangeable drive shaft cartridge in a side view.

FIG. 3 is a top view of the relevant portions of FIG. 2. In the position shown in FIG. 3, most of the length of the outer telescoping tube 82 is received within the tubular housing 110 and the flange 154 is positioned close to the tabs 114. As shown in FIG. 4, further distal movement of the interconnected carriages 150 and 200 causes the proximal ends of the resilient tabs 114 to deflect radially outwardly so the shoulders 1 16 can move over the flange 154. As soon as the carriages are moved distally a little further, the shoulders 116 of the resilient tabs 114 are received in the groove 156 behind the flange 154, as shown in FIGS. 5 and 6. Since the shoulders 116 of the tabs 114 are free to circumferentially slide in the groove 156, the outer telescoping tube 82 is free to rotate with respect to both the tubular housing 110 and the inner telescoping tube 90 when the drive shaft carriage 150 is releasably locked to the tubular housing 110 of the drive shaft cartridge 80. Usually, the entire atherectomy device, including the drive shaft 60, is pulled off the guide wire 104 before the carriages 150 and 200 are disconnected.

As noted above, the drive shaft carriage 150 and the prime mover carriage 200 are designed to be releasably interconnected to move together as a unit. FIGS. 7–10 illustrate the process of disconnecting the drive shaft carriage 150 from the prime mover carriage 200. The carriages 150 and 200 are each provided with fittings which releasably interconnect the carriages. Desirably, at least one of the fittings is free to rotate with respect to the carriage with which it is associated to facilitate connection of the carriages to one another.

These fittings desirably comprise mating components of a bayonet joint, i.e., a joint in which two mechanical parts are so interconnected that they cannot be separated by longitudinal movement. In the embodiment shown in the drawings, these mating components comprise pegs 160 carried by the drive shaft carriage 150 and slots 310 formed in a bayonet collar 300 carried by the prime mover carriage 200. The bayonet collar 300 preferably is rotatable about the prime mover carriage 200.

Figure 7:
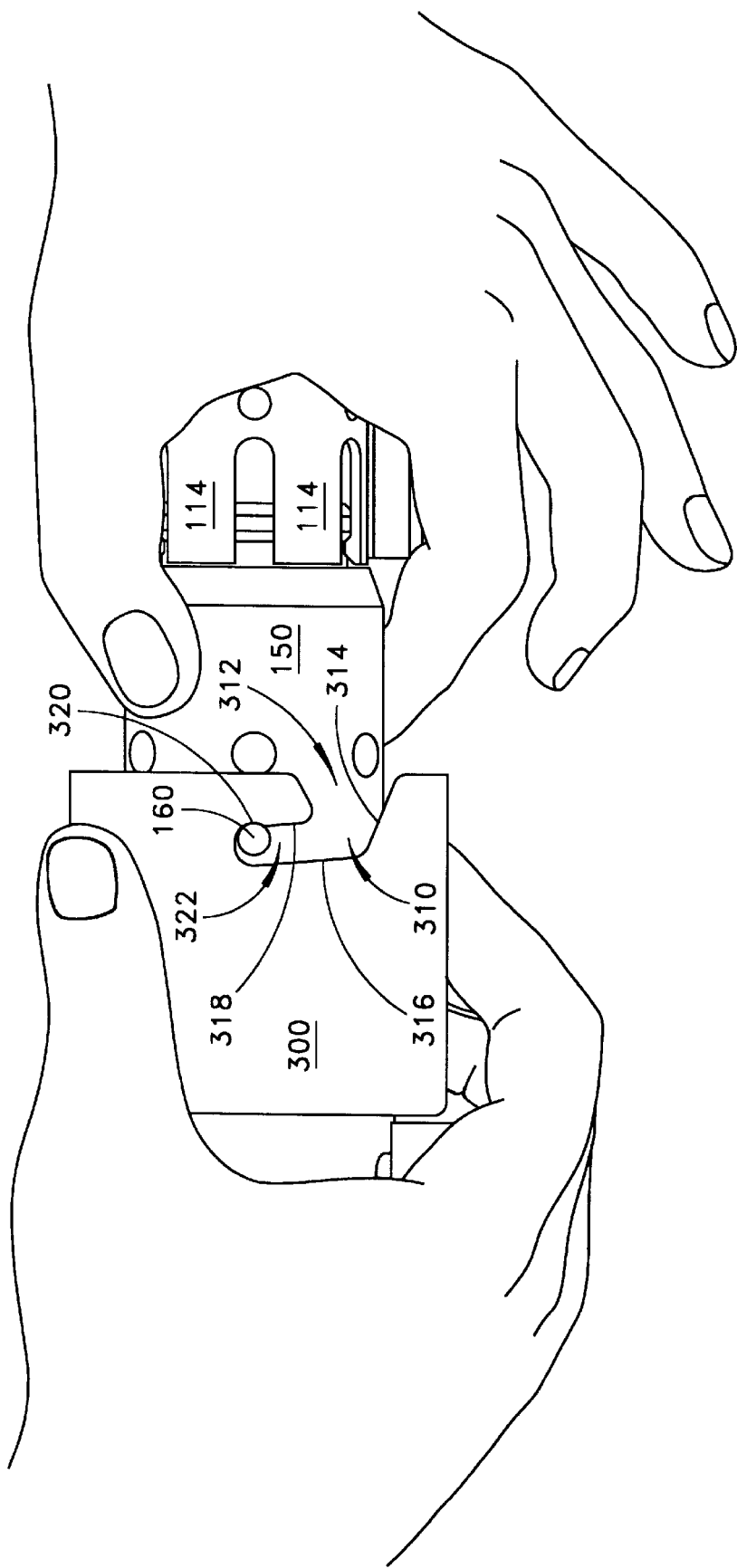
FIGS. 7–9 schematically illustrate the process of disconnecting the drive shaft carriage from the prime mover carriage.
Figure 8:
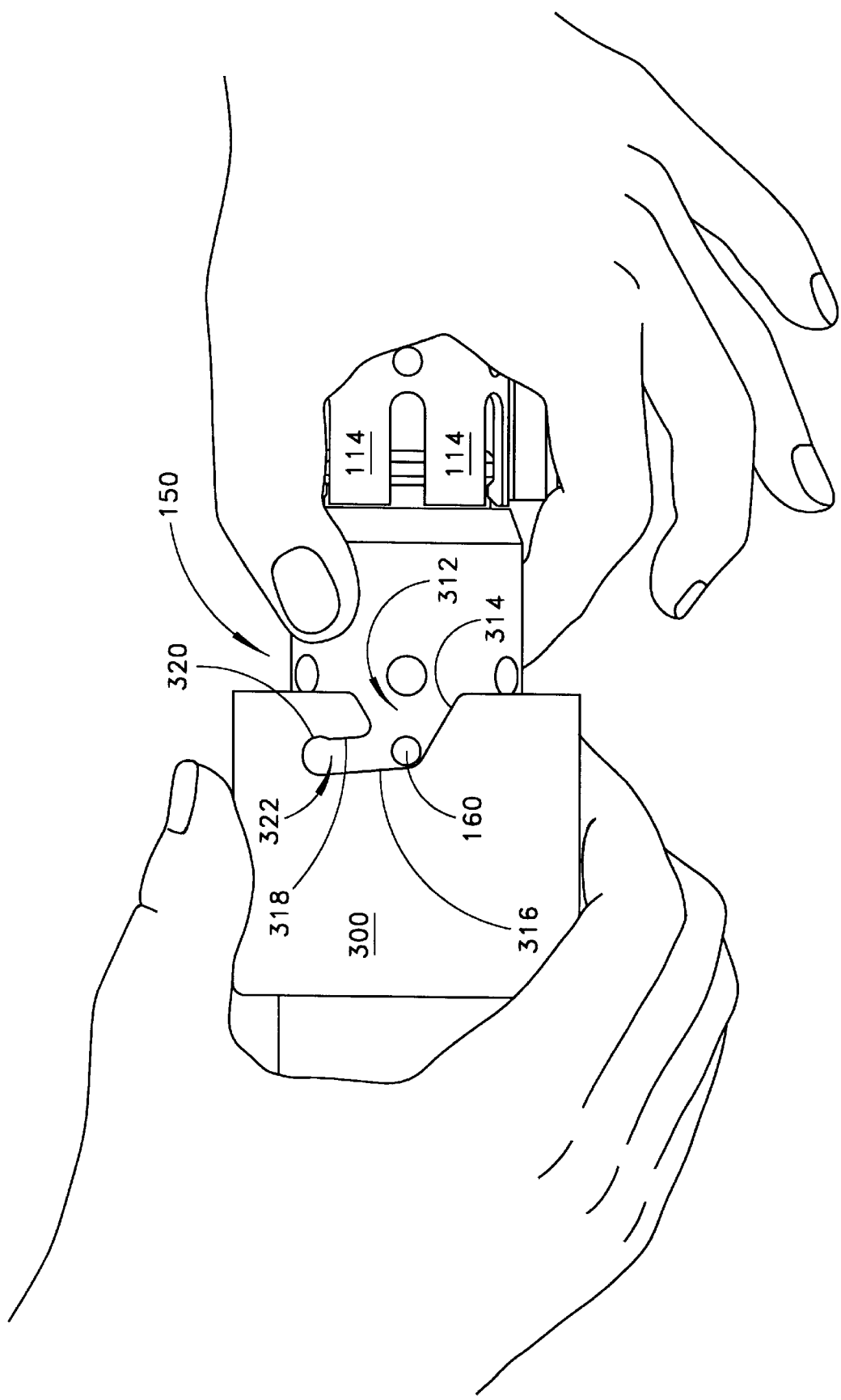
Figure 9:
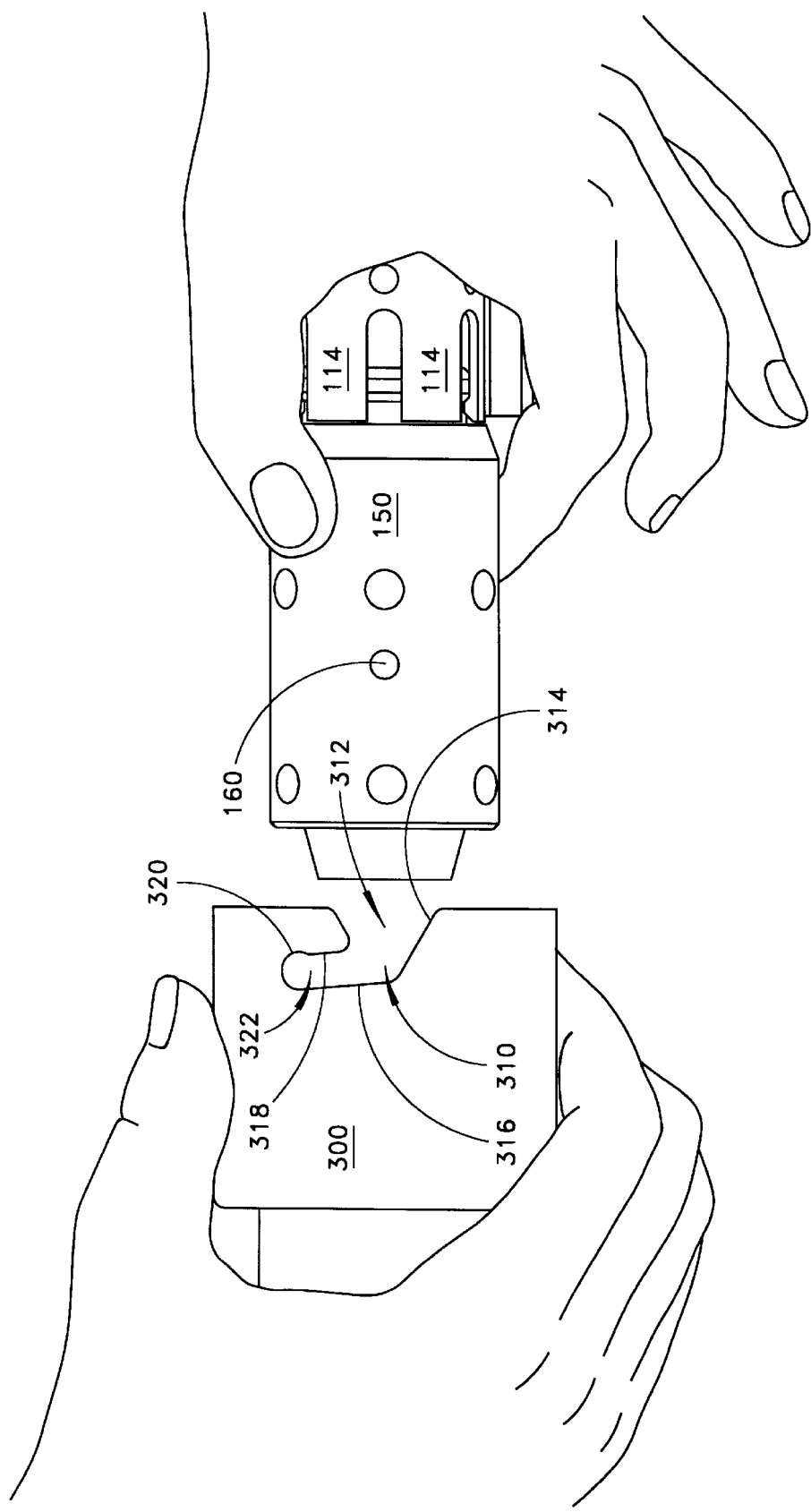

There preferably are at least three pegs 160 equiangularly spaced about the drive shaft carriage and an equal number of slots 310 which are equiangularly spaced about the bayonet collar 300. The pegs 160 slide within the slots 310 when the bayonet collar 300 is rotated. As illustrated in FIGS. 7–9, the operator manually grasps the drive shaft carriage 150 with one hand and the bayonet collar 300 with the other hand. The operator then rotates the bayonet collar until the pegs 160 reach the inlets 312 of the slots 310, as shown in FIG. 8. Once the pegs 160 reach the inlets 312 of the slots, the operator moves the bayonet collar 300 proximally, thereby moving the prime mover carriage 200 away from the drive shaft carriage 150, as shown in FIGS. 9 and 10.

Figure 10:
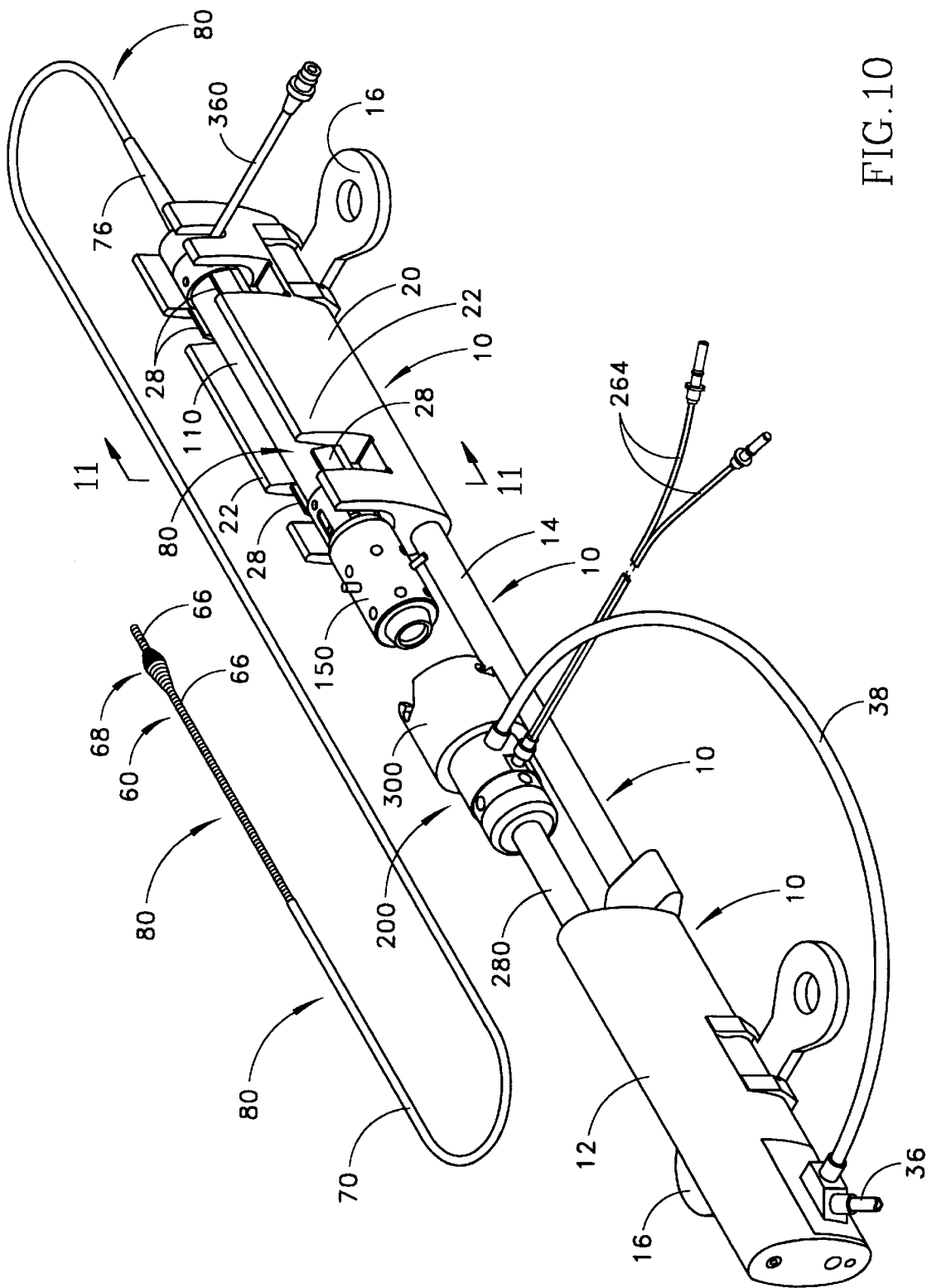
FIG. 10 is a perspective view similar to FIG. 1, but illustrating the drive shaft carriage disconnected from the prime mover carriage.
Figure 11:
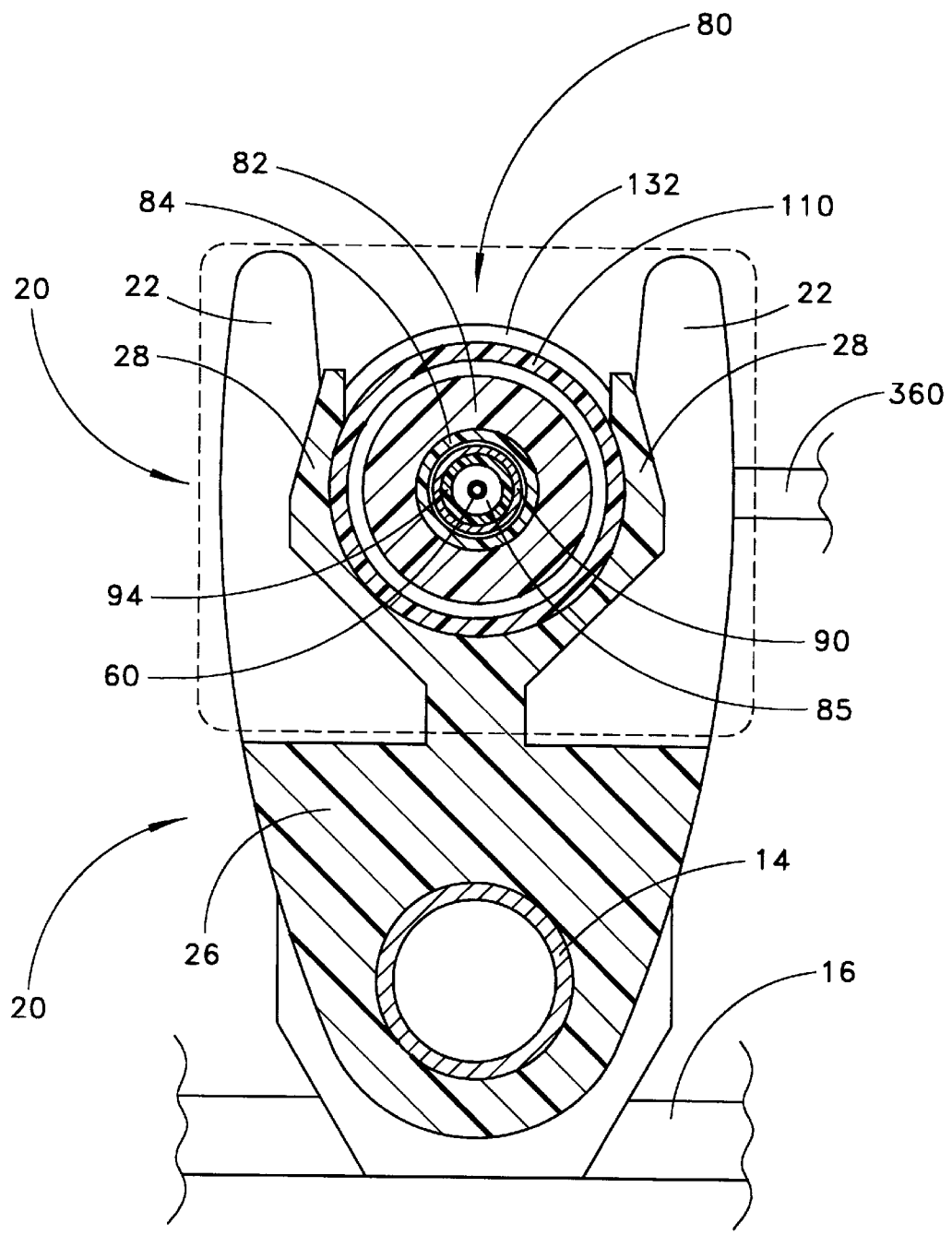
FIG. 11 is a schematic cross sectional view taken along line 11—11 in FIG. 10 and showing how the exchangeable drive shaft cartridge is attached to a distal portion of the handle.
Figure 12:
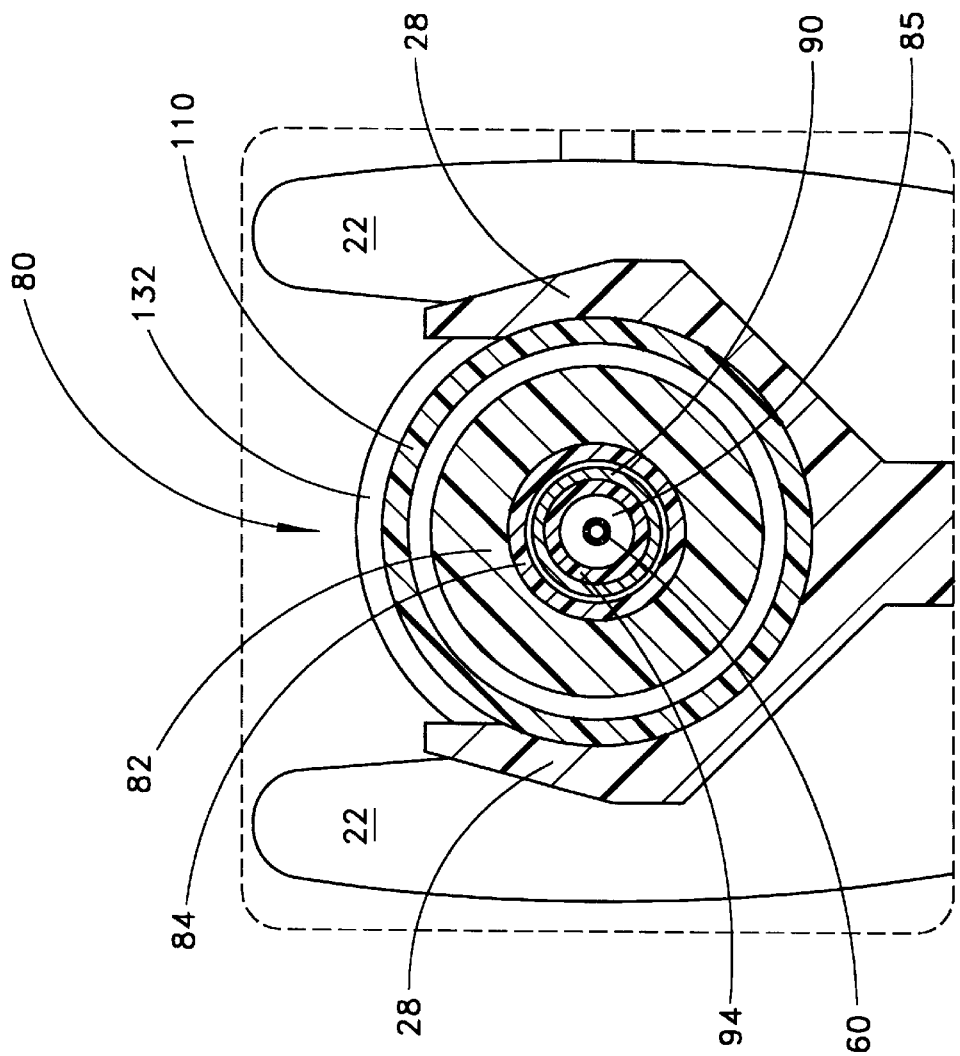
FIG. 12 is an enlarged view of the section outlined in FIG. 11.
Figure 13:
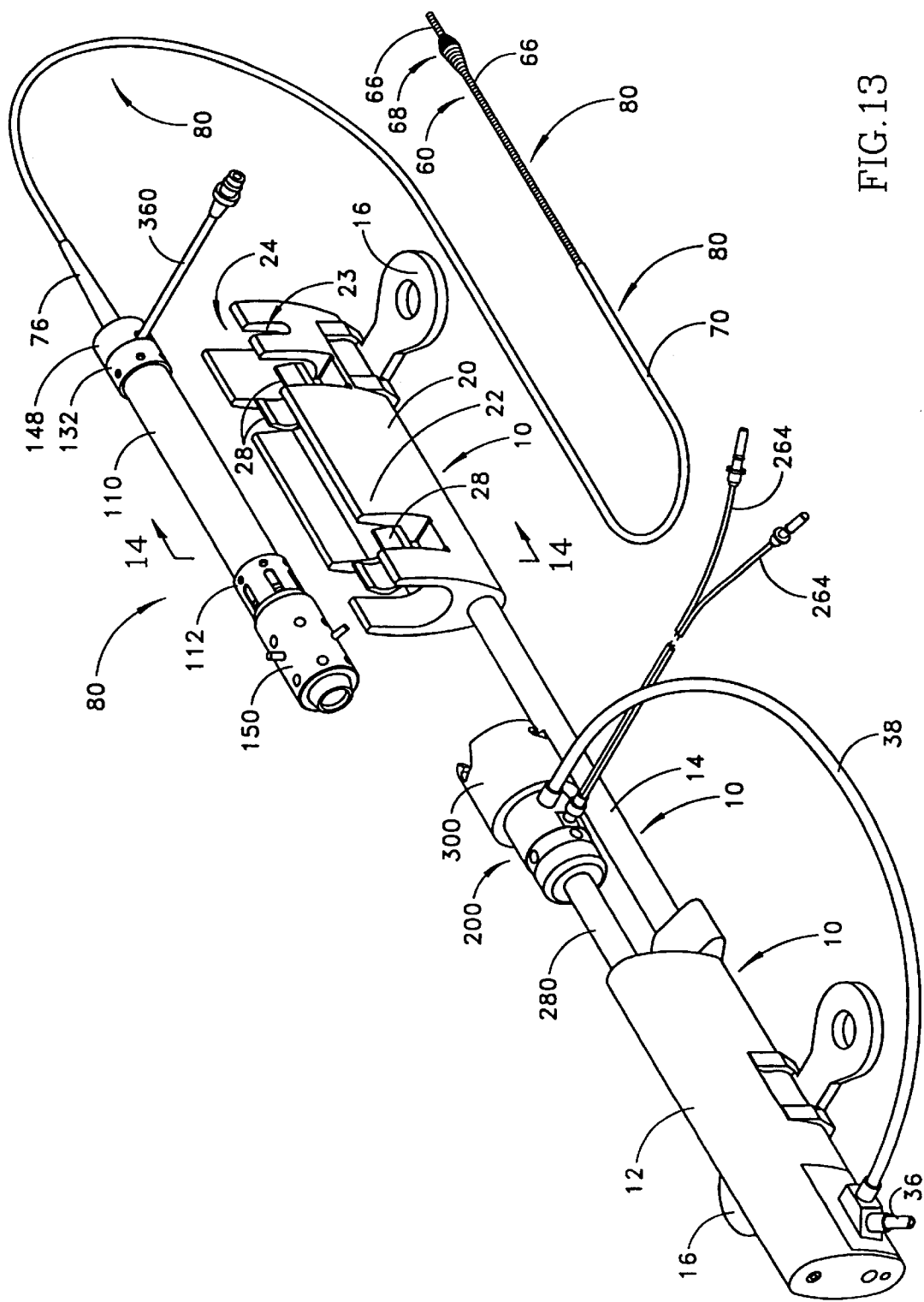
FIG. 13 is a perspective view similar to FIG. 10, but showing the exchangeable drive shaft cartridge detached from the distal portion of the handle.
Figure 14:
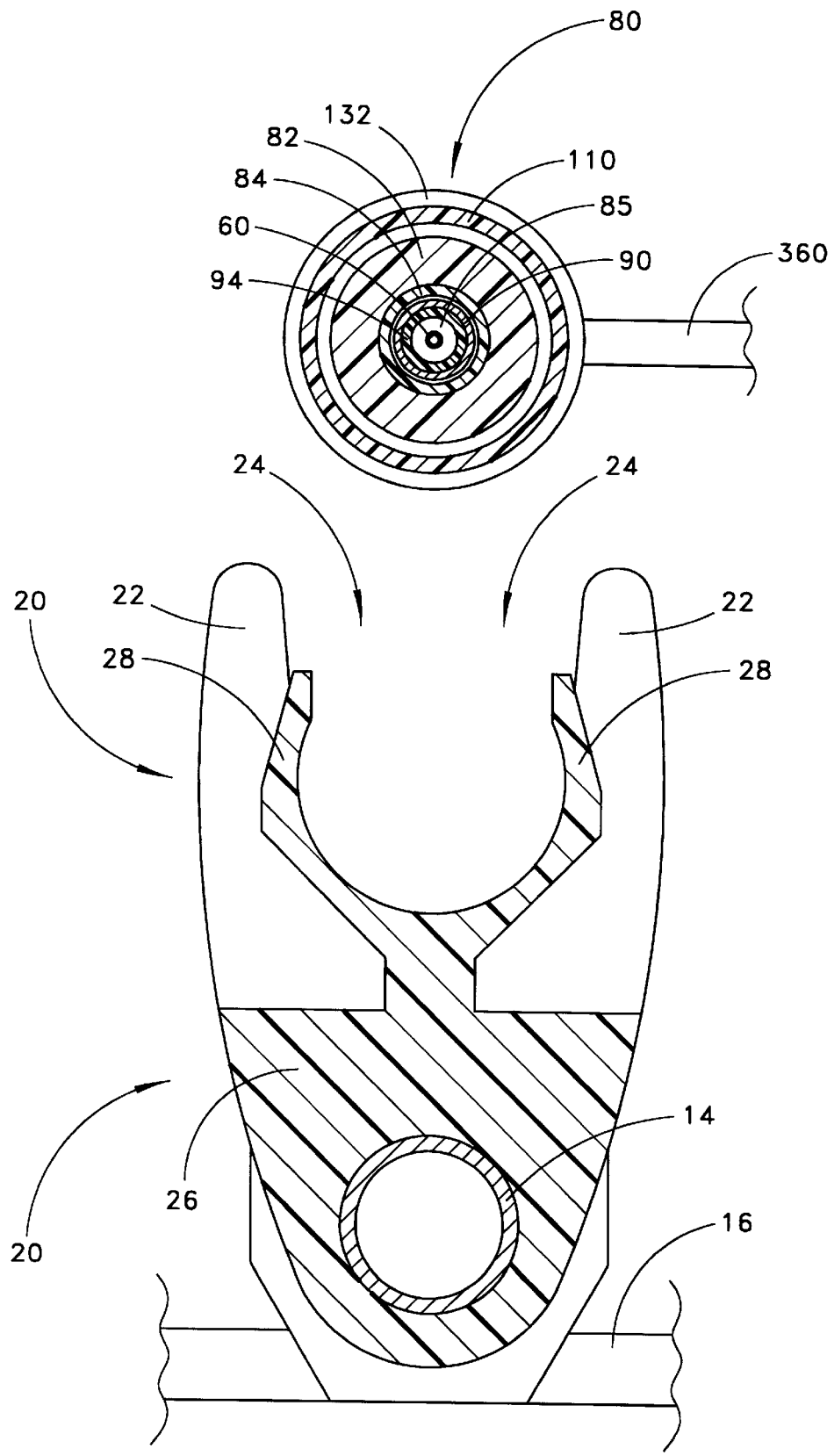
FIG. 14 is a schematic cross sectional view taken along line 14—14 in FIG. 13.

FIGS. 10–14 schematically illustrate how the exchangeable drive shaft cartridge 80 can be disconnected from the distal portion 20 of the handle 10. In particular, FIGS. 10–12 illustrate how the exchangeable drive shaft cartridge 80 is held in the distal portion 20 of the handle 10 while FIGS. 13 and 14 illustrate the exchangeable drive shaft cartridge disconnected from the distal portion 20 of the handle.

As noted above, the distal portion 20 of the handle 10 is designed to releasably hold the exchangeable drive shaft cartridge 80. In the illustrated embodiments, the distal portion 20 of the handle 10 includes a pair of opposing side walls 22 which define a longitudinally extending groove 24 (best seen in FIGS. 13 and 14). This groove 24 is sized to releasably hold a length of the exchangeable drive shaft cartridge 80 therein. Although the longitudinally extending groove 24 may be oriented in a variety of ways, in the preferred embodiment shown in the drawings, the groove 24 is upwardly open to make it easier to insert and remove the exchangeable drive shaft cartridge 80.

In use, an operator may wish to grasp the handle 10 around the distal portion 20. The longitudinally extending groove 24 desirably has a depth greater than the outer diameter of the tubular housing 110 in order to limit manual pressure on the tubular housing 110 when a user grasps the handle around the groove. Optimally, the walls 22 defining the groove 24 are high enough to extend above the tubular housing 110, substantially preventing any inadvertent deformation of the tubular housing 110 which may interfere with optimal operation of the longitudinally extendable tube 100 (e.g., by making it more difficult to move the outer telescoping tube 82 with respect to the tubular housing 110 and the inner telescoping tube 90).

The distal portion 20 of the handle preferably also includes at least one clamp 28 for retaining the exchangeable drive shaft cartridge 80 in the groove 24. In the embodiment of FIGS. 10–14, there are two such clamps 28 and these clamps are spaced from one another longitudinally along the distal portion of the handle. (In the embodiment of FIGS. 15 and 16, there is only one such clamp 34, but that clamp 34 is longer to ensure that the exchangeable drive shaft cartridge is securely held in the desired position.) In addition, these clamps 28 (or the clamp 34) may also serve to limit longitudinal movement of the exchangeable drive shaft cartridge 80 within the longitudinally extending groove 24. For example, the proximal of the two clamps 28 (or the proximal end of the clamp 34) preferably abuts the proximal collar 112 which carries the tabs 114 of the tubular housing 110 and the distal of the two clamps 28 (or the distal end of the clamp 34) preferably abuts a distal collar 132 of the tubular housing.

Figure 15:
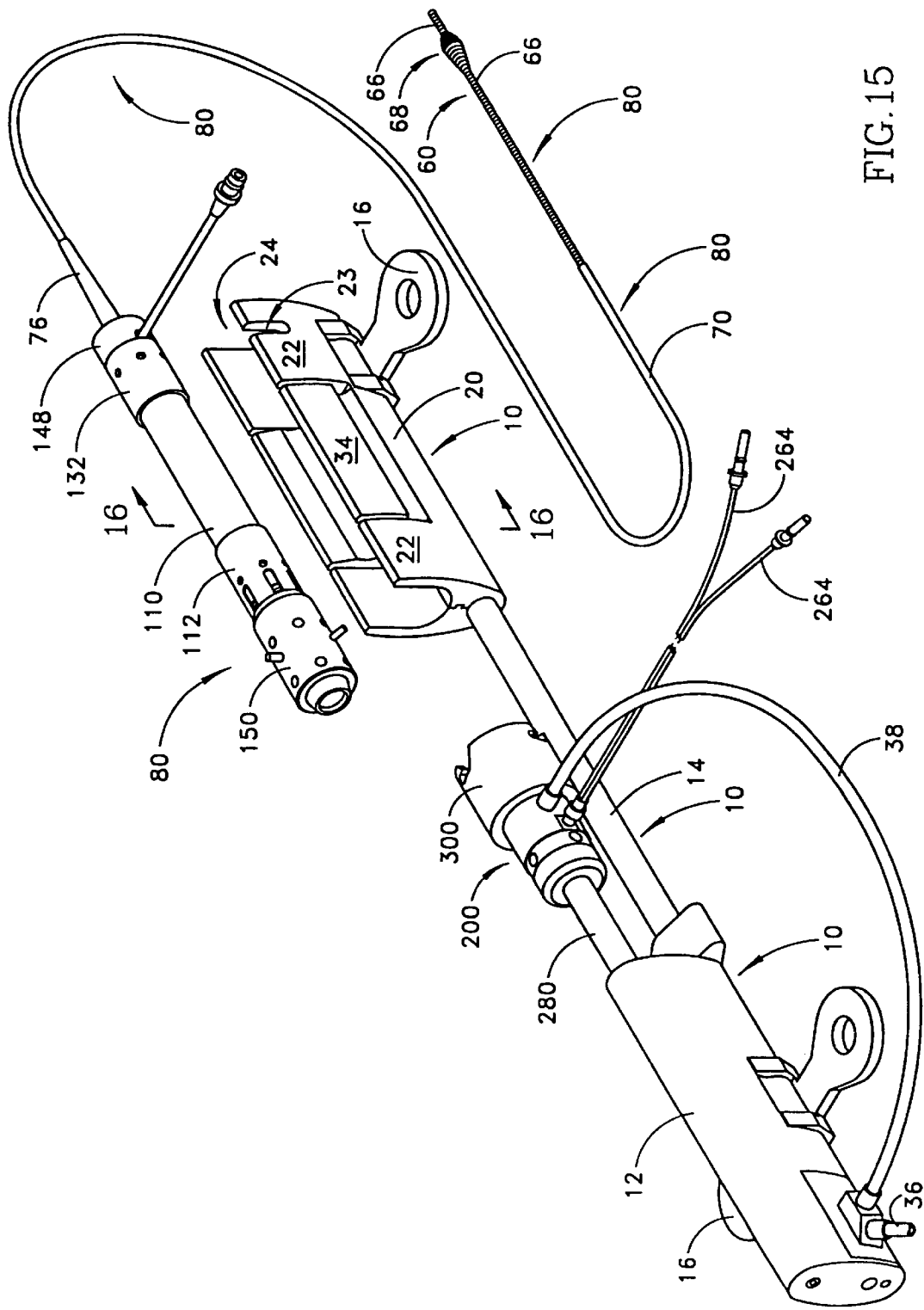
FIG. 15 is a perspective view similar to FIG. 13, showing the exchangeable drive shaft cartridge detached from a handle which has a somewhat different design of its distal portion.
Figure 16:
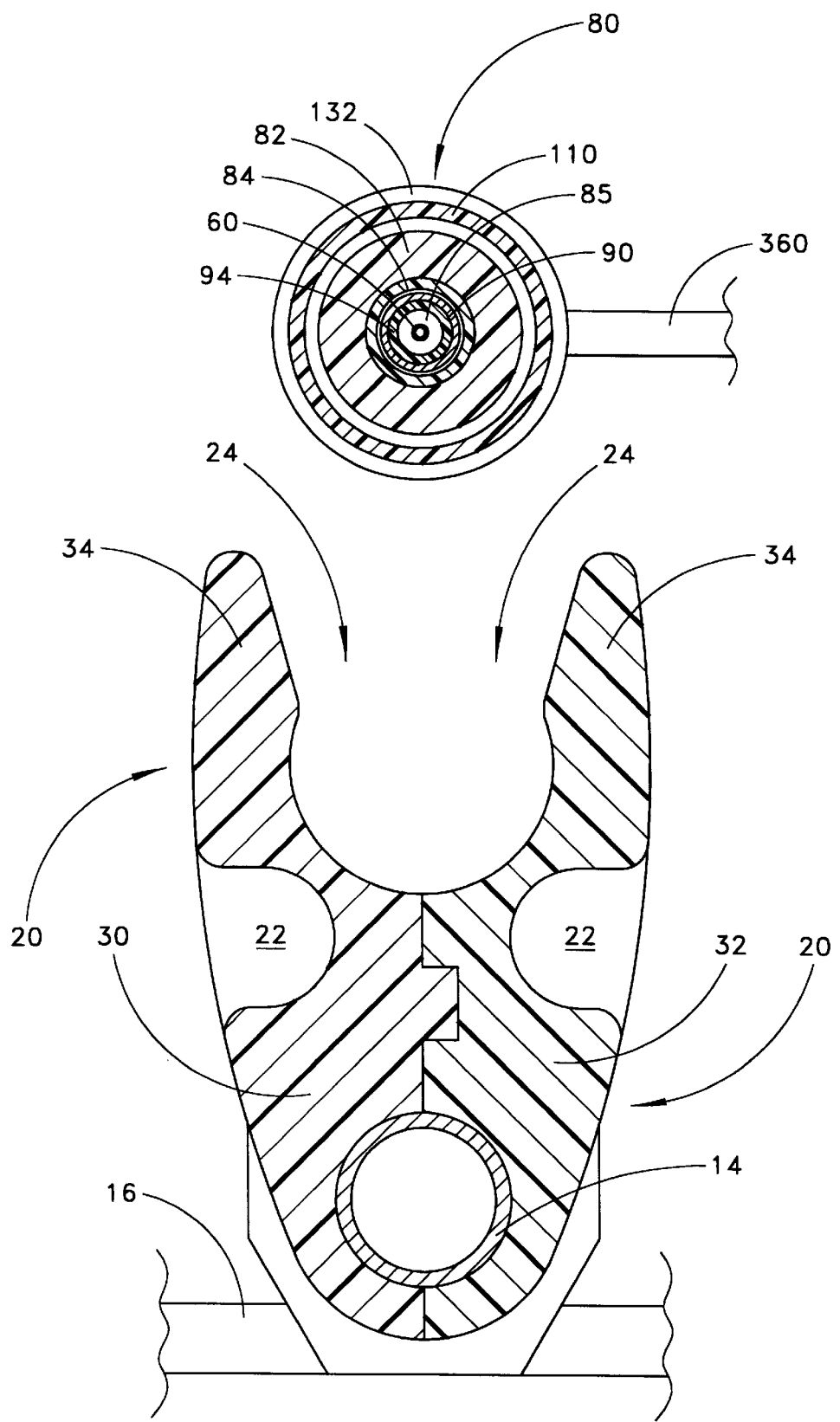
FIG. 16 is a schematic cross-sectional view taken along line 16—16 of FIG. 15.

If so desired, one or more elements of the distal portion 20 of the handle can be integrally formed to make manufacturing easier. In the embodiment illustrated in FIGS. 10–14, the walls 22 defining the groove 24, the clamps 28, and the base 26 of the distal portion 20 of the handle are all integrally formed as a single component. In the embodiment of FIGS. 15 and 16, the corresponding elements of the distal portion 20 of the handle are instead formed from two separate mating elements 30 and 32. In particular, the clamp 34 includes two opposing sides. One side of the clamp 34 is integrally formed with the wall 22 which is part of the mating element 30. The other side of the clamp 34 is integrally formed with the opposing wall 22 which is part of the other mating element 32. These two mating elements 30 and 32 can be attached to one another, such as by a suitable adhesive or by appropriately interlocking fittings.

One can remove the exchangeable drive shaft cartridge 80 from the distal portion 20 of the handle 10 simply by lifting the cartridge 80 vertically out of the upwardly open groove 24. Once the exchangeable drive shaft cartridge 80 is removed as shown in FIGS. 13 and 14, another exchangeable drive shaft cartridge (e.g., a cartridge with a larger diameter abrasive tissue removing implement) can be inserted in the groove 24 in the distal portion 20 of the handle. The distal portion 20 of the handle, or the entire handle 10, can be formed of a sterilizable material such as titanium so the distal portion of the handle, or the entire handle, can be reused.

Figure 17:
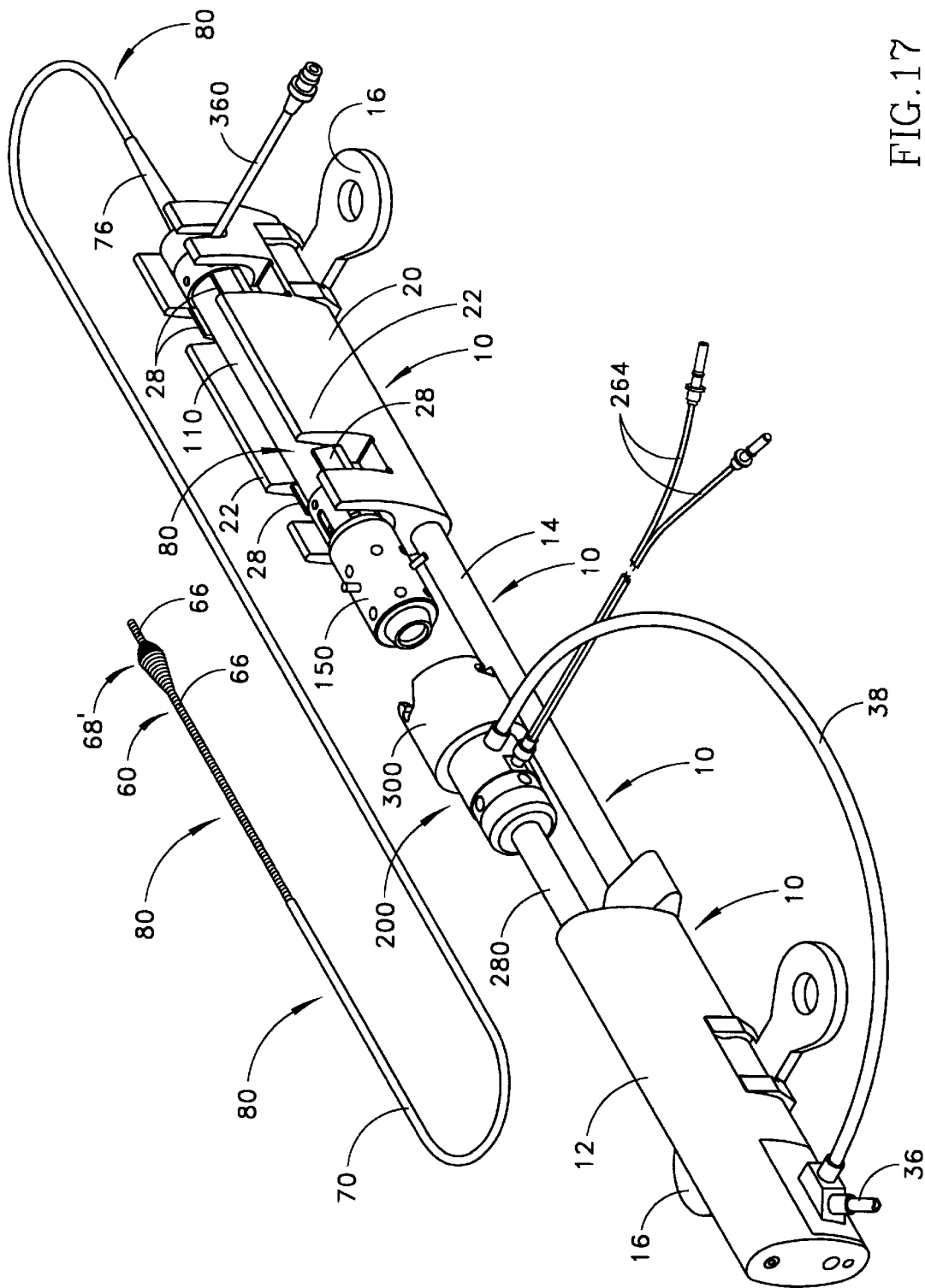
FIG. 17 is a perspective view similar to FIG. 10, but showing another exchangeable drive shaft cartridge attached to the distal portion of the handle.

FIG. 17 illustrates another exchangeable drive shaft cartridge 80 inserted in the groove 24 in the distal portion 20 of the handle. The cartridge 80 shown in FIG. 17 is identical to the cartridge shown in the preceding figures, except that the new cartridge 80 has a larger diameter tissue removal implement 68', as may be evident from comparing FIGS. 10 and 17. The process of inserting the exchangeable drive shaft cartridge 80 in the distal portion 20 of the handle 10 is essentially the reverse of the process in which it is disconnected from the handle. First, the operator should longitudinally align the exchangeable drive shaft cartridge 80 with the distal portion 20 of the handle such that both clamps 28 are touching the tubular housing 110 between the proximal collar 112 and distal collar 132. Once the exchangeable drive shaft cartridge 80 is properly positioned, it simply may be pushed downwardly into the upwardly open groove 24 until it snaps in place in the clamps 28.

One of the opposing walls 22 includes a slot 23 (best seen in FIGS. 13 and 15, for example) for receiving a flexible fluid supply tubing 360 therein. As described more fully below, this flexible fluid supply tubing 360 is attached to the exchangeable drive shaft cartridge 80 and supplies fluid to the drive shaft and guide wire lumens.

Figure 18:
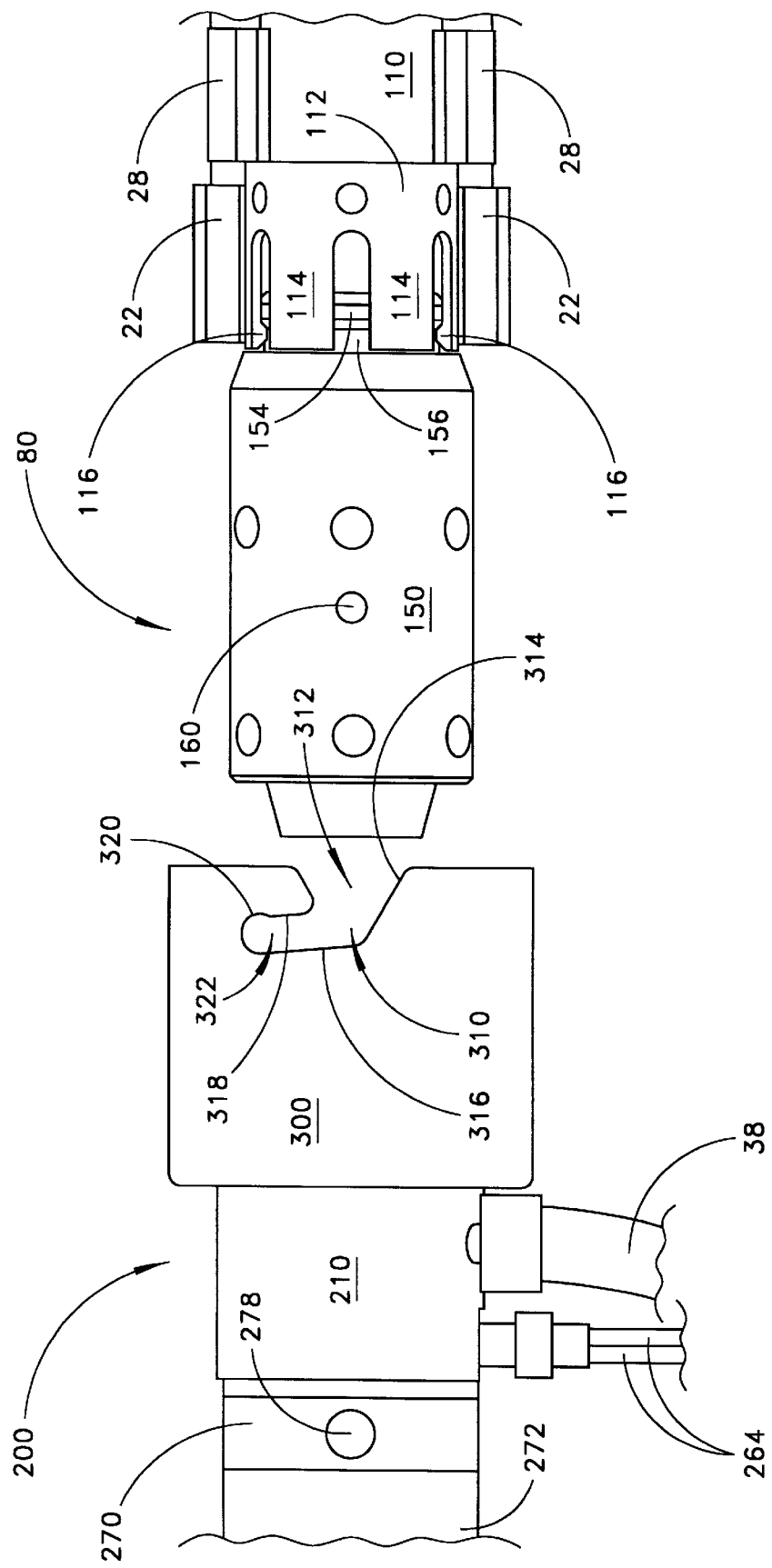
FIG. 18 is a top view of a broken-away portion of the device of FIG. 17 showing the drive shaft carriage spaced from the prime mover carriage.
Figure 19:
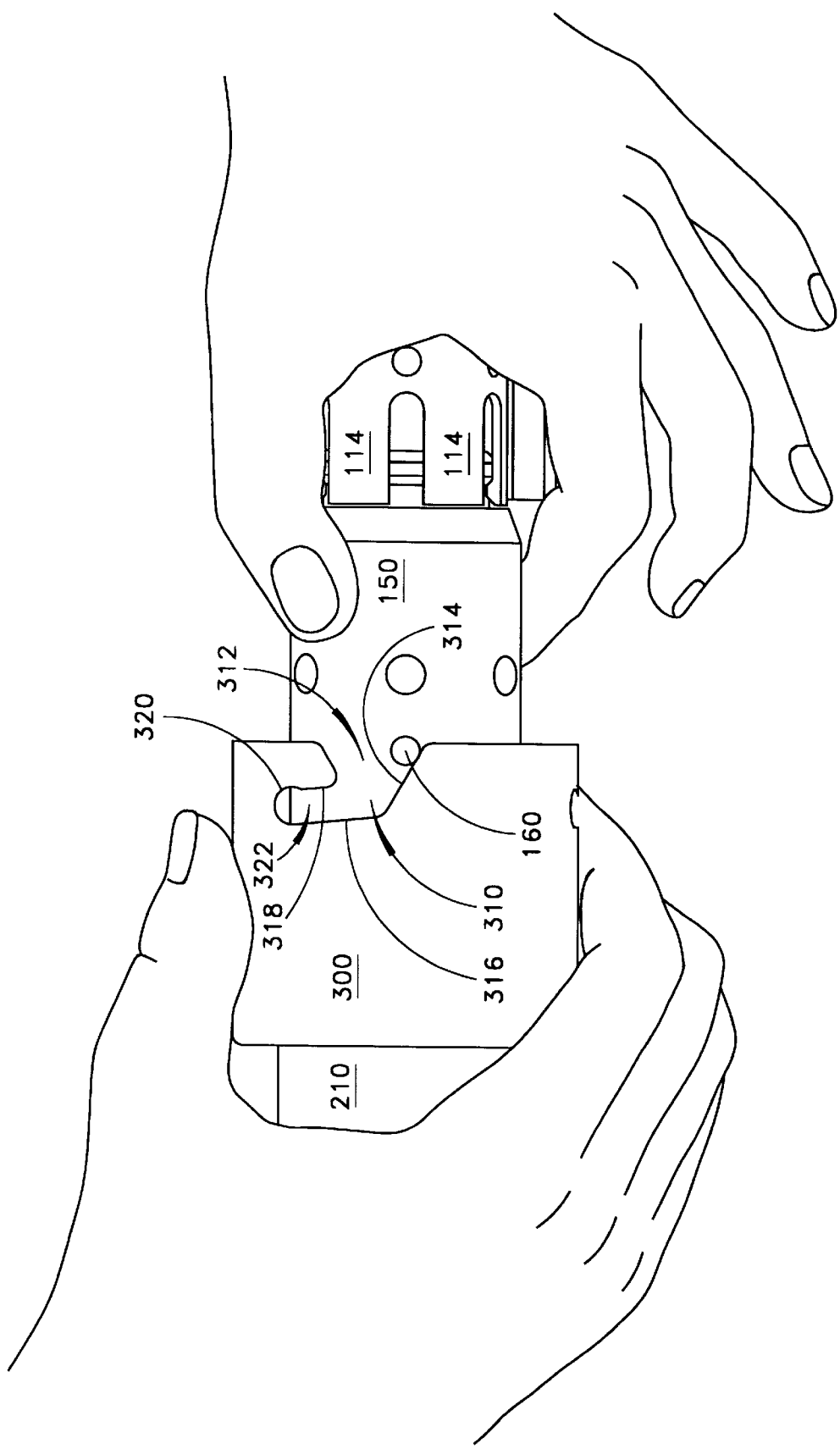
FIGS. 19 and 20 are top views illustrating the process of interconnecting the drive shaft carriage and the prime mover carriage.
Figure 20:
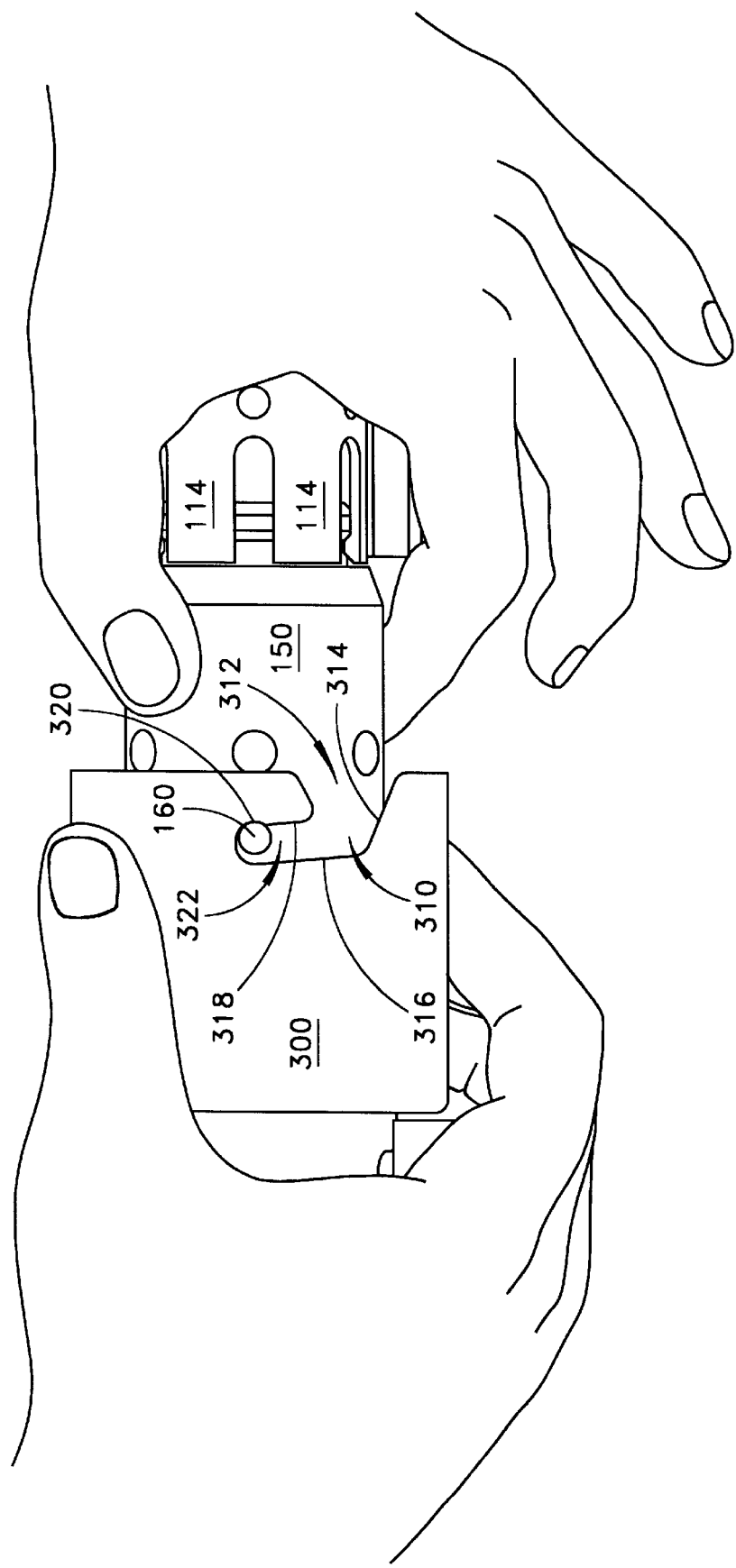

FIGS. 18–20 are top views schematically illustrating how one may interconnect the drive shaft carriage 150 and the prime mover carriage 200. First, as shown in FIG. 18, the inlets 312 of the slots 310 in the bayonet collar 300 should be longitudinally aligned with the pegs 160 of the drive shaft carriage 150. The inlets 312 of the slots 310 are desirably relatively wide to simplify such longitudinal alignment. Once the slots 310 and the pegs 160 are properly aligned, the prime mover carriage and the drive shaft carriage can be moved toward one another. As shown in FIG. 19, this may be accomplished simply by moving the prime mover carriage 200 distally until each of the pegs 160 is received in the inlet 312 of a slot 310 and preferably contacts the longer guiding wall 314 of the inlet 312. In the illustrated embodiment, the longer guiding wall 314 of each inlet 312 forms an obtuse angle with the posterior wall 316 of the leg 322 of the slot 310.

Once the pegs 160 are received in the inlets 312 of the slots 310, the bayonet collar 300 and the drive shaft carriage 150 are rotated with respect to each other until each peg 160 reaches the closed end of a leg 322 and is seated in a small recess 320 formed in the anterior wall 318 of the leg 322, as shown in FIG. 20. The leg 322 of each slot 310 extends generally circumferentially about the bayonet collar 300. Preferably, the leg 322 also extends such that its closed end is positioned slightly proximally with respect to its inlet end. As explained in more detail below in connection with FIGS. 29–31, this will serve to properly position the prime mover coupling 330 and the drive shaft socket 180 with respect to one another.

Figure 21:
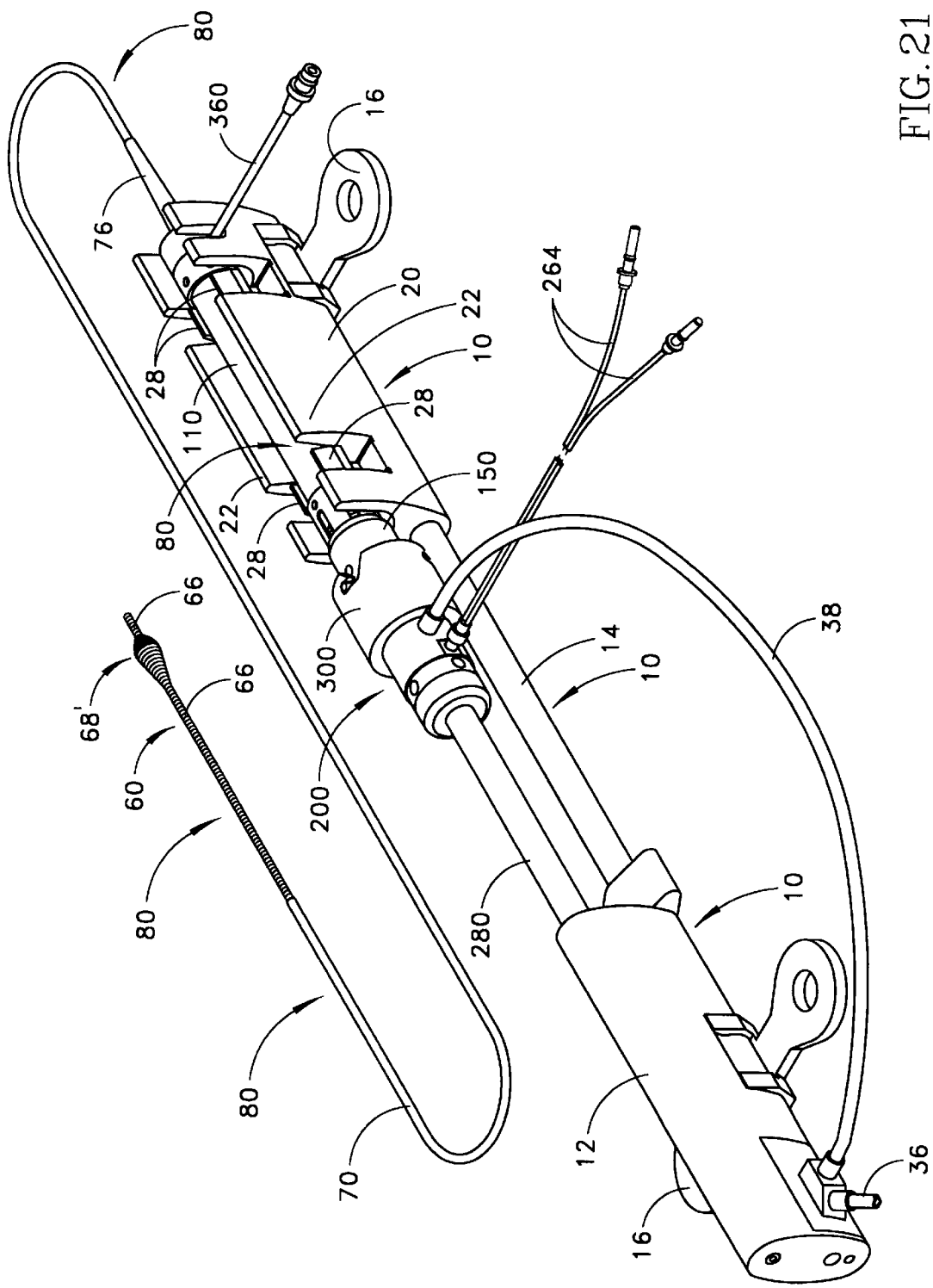
FIG. 21 is a perspective view similar to FIG. 17, but showing the drive shaft carriage and the prime mover carriage interconnected to move together as a unit.
Figure 22:
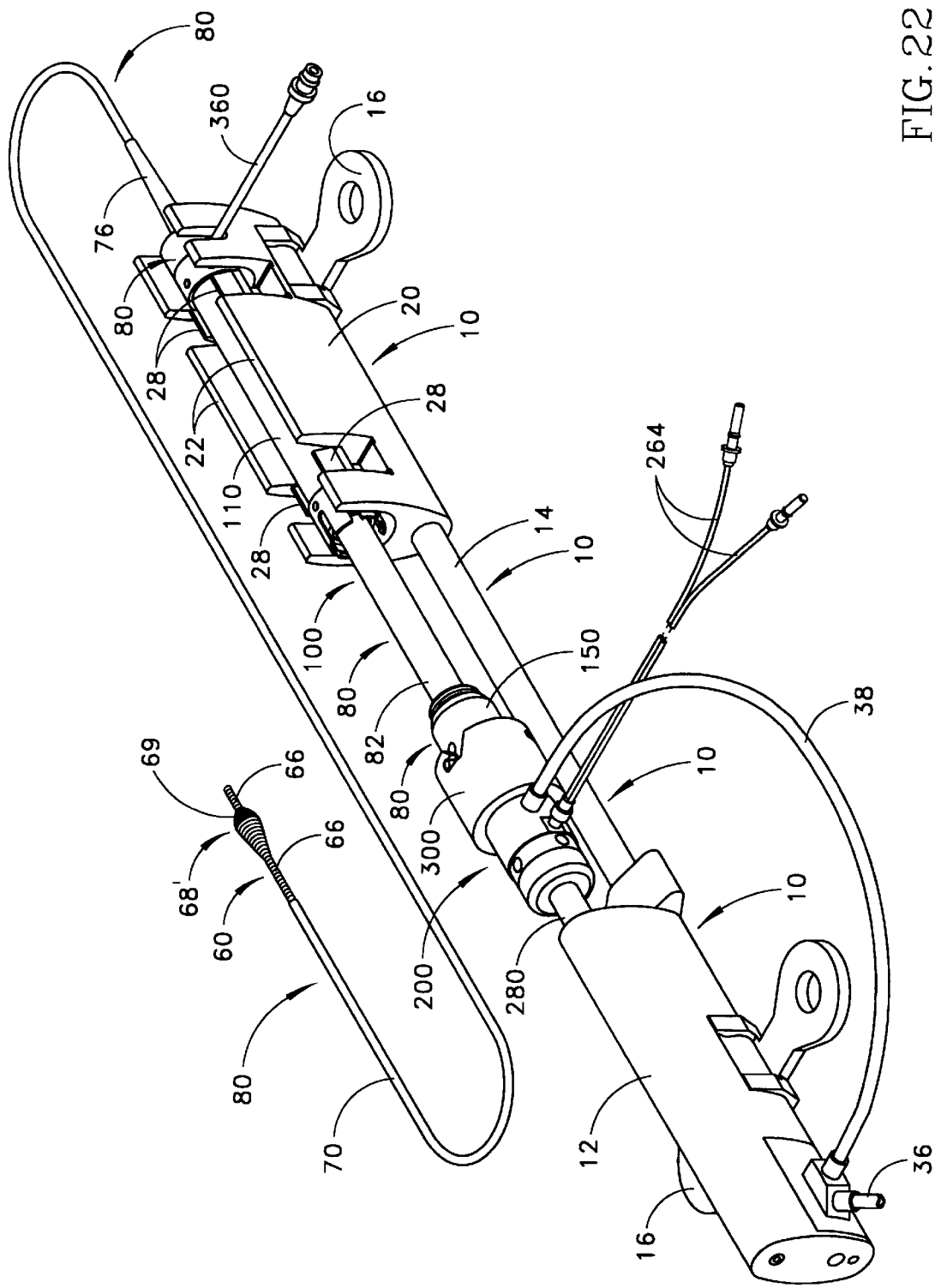
FIG. 22 is a perspective view similar to FIG. 21, but showing the carriages moved proximally so that the interlocking elements of the exchangeable drive shaft cartridge are spaced away from each other.

FIG. 21 illustrates the interconnected carriages 150 and 200 in their most distal position. In this position, the tubular housing 110 and the drive shaft carriage 150 are in their interlocked position. FIG. 22 illustrates the interconnected carriages 150 and 200 moved proximally, thereby disconnecting the drive shaft carriage 150 from the tubular housing 110 so the telescoping tubes 82 and 90 can slide with respect to one another. FIGS. 17–22 illustrate a process wherein the carriages 150 and 200 are interconnected before the drive shaft carriage 150 is disconnected from the tubular housing 110. It should be understood, however, that the order of these two steps can be reversed and the drive shaft carriage 150, together with the outer telescoping tube 82, may be moved proximally before the carriages 150 and 200 are interconnected.

As noted above, the handle 10 includes a proximal portion 12, a distal portion 20 and an intermediate portion 14 extending therebetween. In the illustrated embodiment, this intermediate portion 14 comprises an elongated rod or tube which connects the proximal 12 and distal 20 portions of the handle to one another. As discussed below in connection with FIG. 64, outer 280 and inner 290 proximal telescoping tubes are slidably received in the proximal portion 12 of the handle. Distal ends of these telescoping tubes 280 and 290 are connected to the prime mover carriage. The elongated rod of the intermediate portion 14 of the handle extends generally parallel to these telescoping tubes 280 and 290 and is spaced therefrom a distance sufficient to permit both the drive shaft carriage and the prime mover carriage to move parallel to the elongated rod of the handle. Thus, when the drive shaft carriage 150 and the prime mover carriage 200 are interconnected, they can move together as a unit both longitudinally and rotationally with respect to the handle 10. It should be noted that when the interconnected carriages 150 and 200 are moved longitudinally, this will move the drive shaft 60 and its tissue removal implement 68 along a vascular lumen of the patient's body.

Figure 23:
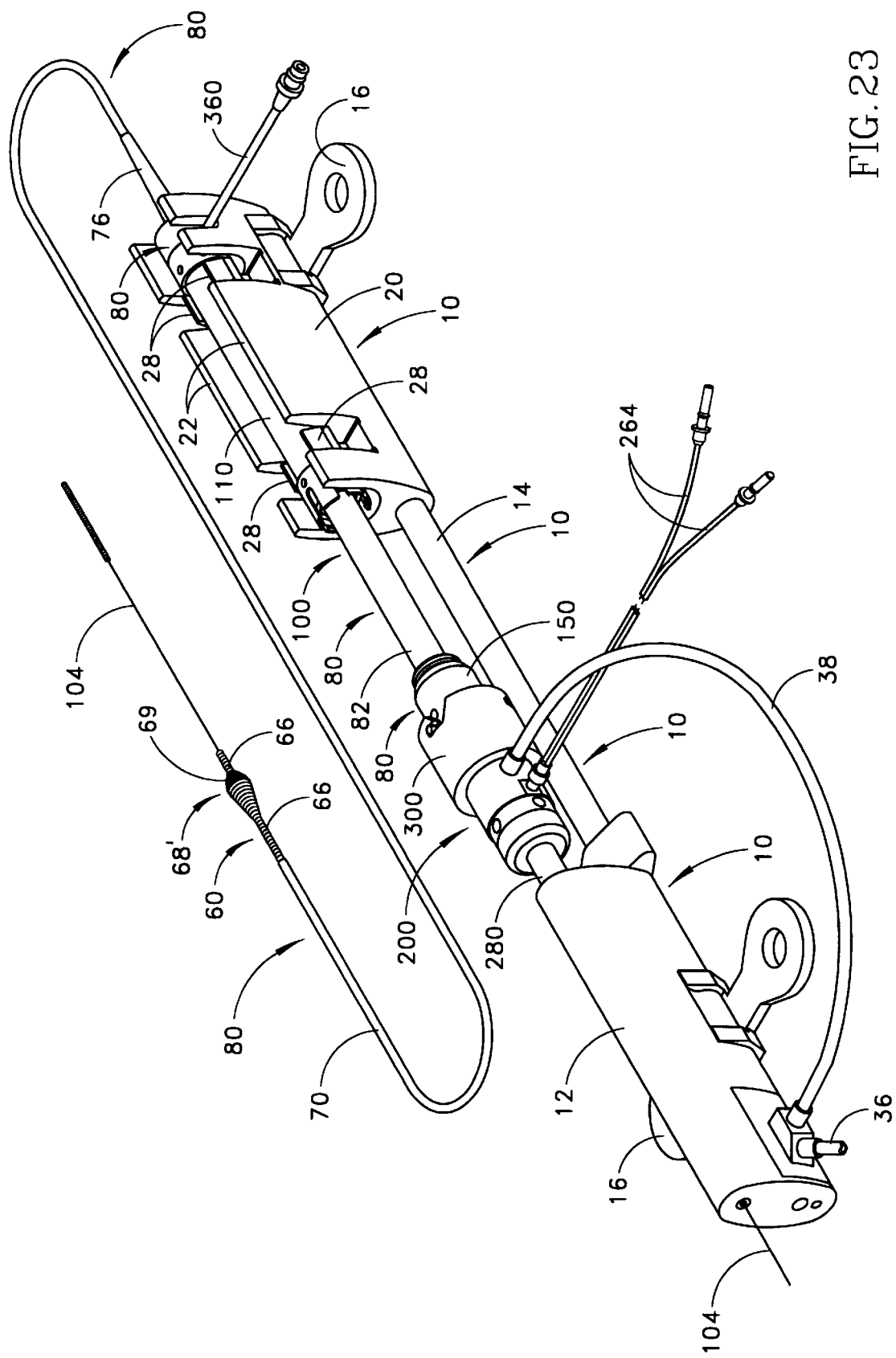
FIG. 23 is a perspective view similar to FIG. 22, but wherein the rotational atherectomy device has been advanced over a guide wire.

FIG. 23 illustrates the assembled rotational atherectomy device advanced over the guide wire 104. The device may be advanced over the guide wire at any time after the two carriages 150 and 200 have been interconnected. In clinical use, the guide wire is first advanced across a lesion in the patient's vessel and only then the assembled device is advanced over the guide wire.

Figure 24:
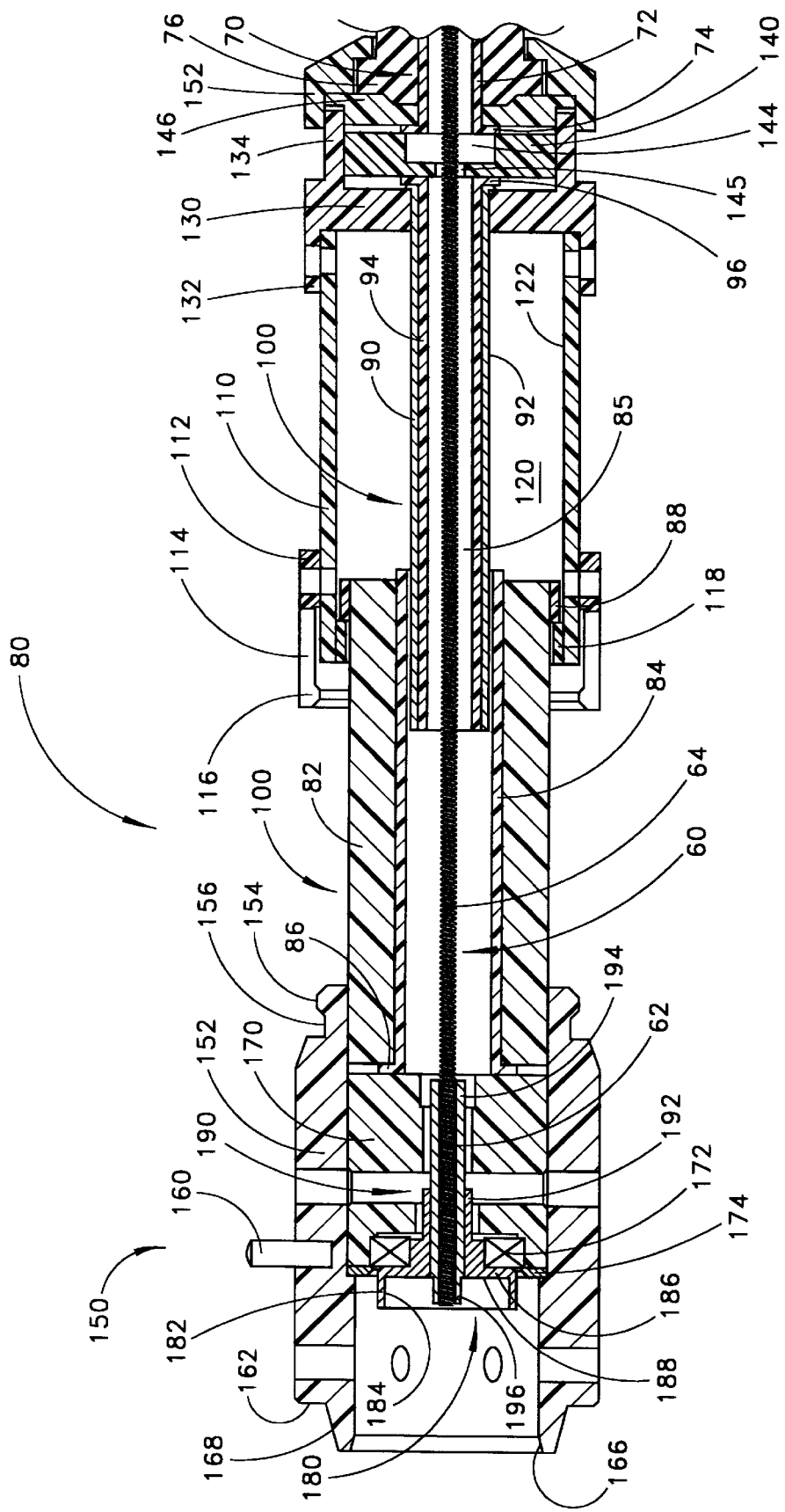
FIG. 24 is a broken-away longitudinal cross sectional view of the drive shaft cartridge showing the interlocking elements of the exchangeable drive shaft cartridge spaced from one another.
Figure 25:
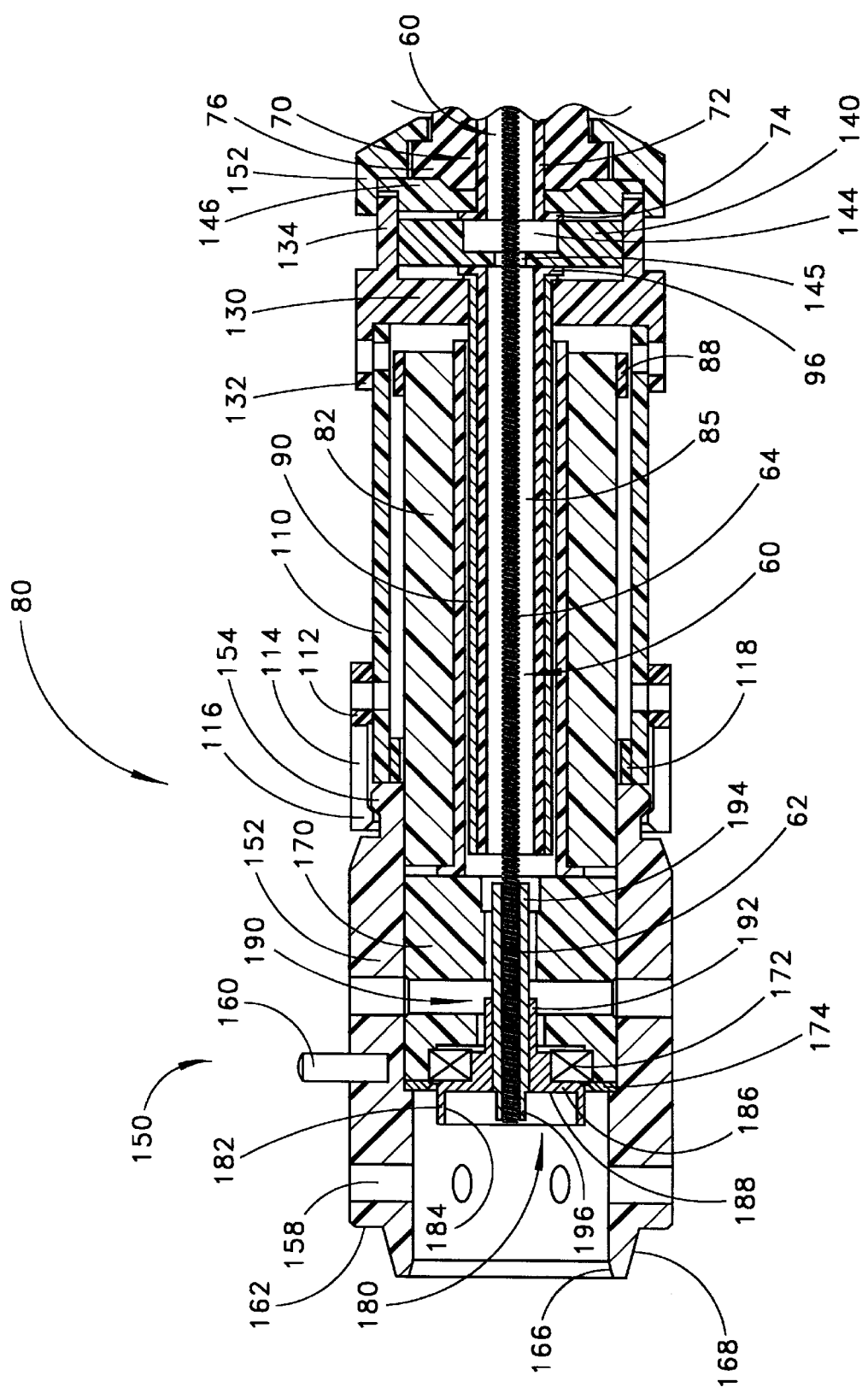
FIG. 25 is a longitudinal cross sectional view similar to FIG. 24 showing the interlocking elements of the exchangeable drive shaft cartridge in their interlocked position.
Figure 28:
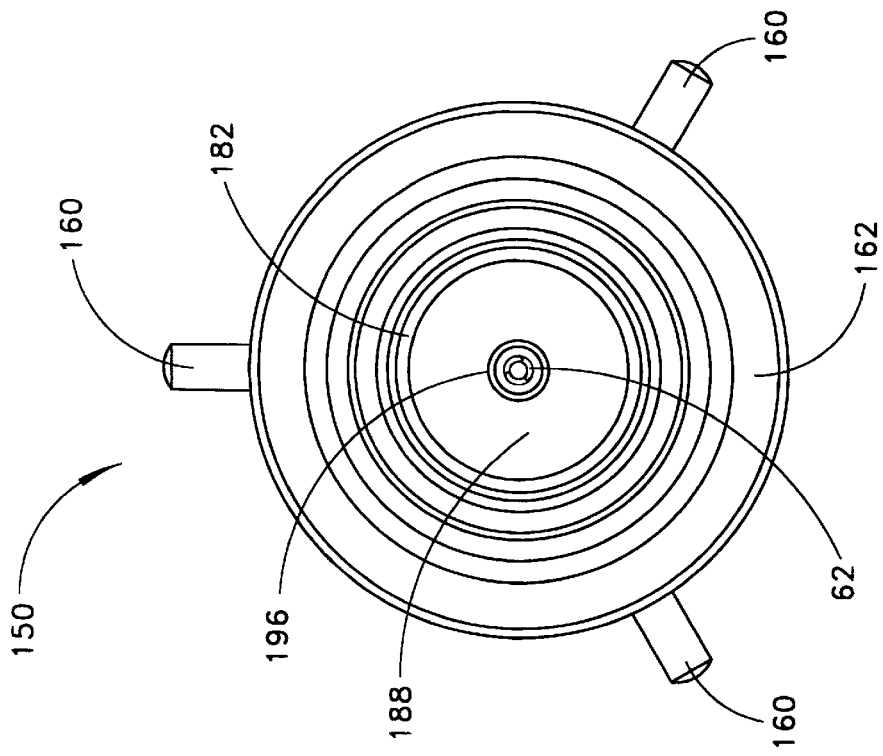
FIG. 28 is a schematic end view of the drive shaft carriage taken along line 28—28 in FIG. 26.

FIGS. 24 and 25 are broken-away longitudinal cross sectional views of one preferred embodiment of an exchangeable drive shaft cartridge 80 of the invention. FIG. 28 is a proximal end view of the same cartridge.

As described above, the exchangeable drive shaft cartridge 80 includes a drive shaft carriage 150, a longitudinally extendable tube 100 extending distally from the drive shaft carriage, an elongated catheter 70 having a proximal end portion 72 which is operatively connected to a distal end portion of the longitudinally extendable tube 100, and a rotatable flexible drive shaft 60. The drive shaft 60 is formed of a helically wound wire and the wire turns of the drive shaft define a guide wire lumen within which a guide wire may be received. The guide wire 104 is not shown in FIGS. 24, 25 and 28, but is shown in FIGS. 32–35, for example.

The flexible drive shaft 60 includes a proximal portion 62, an intermediate portion 64, and a distal portion 66. The distal portion 66 of the drive shaft is not shown in FIGS. 24, 25 and 28, but is described above in connection with FIG. 1. The proximal portion 62 of the drive shaft is attached to the drive shaft socket 180 for rotation therewith. The drive shaft socket 180 is carried by the drive shaft carriage 150 and is supported therein by a ball bearing 172. The intermediate portion 64 of the drive shaft is disposed primarily within the longitudinally extendable tube 100 and the catheter 70. Most of the length of the intermediate portion 64 of the drive shaft is disposed in the catheter 70. Only a proximal length of the intermediate portion 64 is shown in FIGS. 24 and 25 since most of the length of the catheter 70 is not shown in these drawings.

The longitudinally extendable tube 100 and the catheter 70 each have a lumen. These lumens together define a drive shaft lumen 85 within which a majority of the length of the drive shaft is received. Fluid supplied to the drive shaft lumen 85 passes between wire turns of the drive shaft 60 into the guide wire lumen.

FIG. 24 shows the longitudinally extendable tube 100 at its maximum length and FIG. 25 shows the longitudinally extendable tube 100 at its minimum length. In the preferred embodiment shown in these drawings, the longitudinally extendable tube 100 includes outer 82 and inner 90 telescoping tubes, the outer telescoping tube 82 being connected to the drive shaft carriage 150 and the inner telescoping tube 90 being connected to a distal end piece 130 of the tubular housing 110. The inner telescoping tube 90, or at least a distal length thereof, defines a distal end portion of the longitudinally extendable tube 100.

The outer telescoping tube 82 is slidably received in an elongated annular space 120 defined between the inner surface 122 of the tubular housing 110 and an outer surface 92 of the inner telescoping tube 90. The outer telescoping tube 82 is moveable within that annular space 120 both longitudinally and rotationally with respect to both the tubular housing 110 and the inner telescoping tube 90. Desirably, the inner surfaces of both the inner 90 and outer 82 telescoping tubes are provided with a low-friction lining 94 and 84, respectively. The lining 94 of the inner telescoping tube 90 helps minimize friction with the drive shaft 60 as it is rotated and moved proximally and distally around a guide wire. The lining 84 of the outer telescoping tube 82 helps minimize friction between the telescoping tubes as the outer tube is moved with respect to the inner telescoping tube.

These linings may be made from any suitable material, such as polytetrafluoroethylene tubing. In the illustrated embodiment, the linings 84 and 94 may be held in place using flanges (86 and 96, respectively) formed at their ends. If so desired, the separate linings may be omitted and the tubes 82 and 90 themselves may be made of a low friction material.

To prevent the disassembly of the longitudinally extendable tube 100, proximal movement of the outer telescoping tube 82 is limited by a pair of stops, one stop 88 being carried adjacent the distal end of the outer telescoping tube 82 and the other stop 118 being carried adjacent the proximal end of the tubular housing 110. To limit friction between the outer telescoping tube 82 and the tubular housing 110, these stops 88 and 118 may be formed of a low friction material such as polytetrafluoroethylene. If so desired, one or both of these stops 88 and 118 can be formed as an integral part of the outer telescoping tube 82 or the tubular housing 110. This is particularly advantageous if the outer telescoping tube 82 or the tubular housing 110 is made from a low friction material.

The drive shaft carriage 150 is carried adjacent the proximal end of the outer telescoping tube 82. The drive shaft carriage generally includes an outer shell 152 which is attached to the outer telescoping tube 82 and a carriage core 170 which carries the drive shaft socket 180. The carriage core 170 desirably includes a recess for receiving a bearing 172 which supports the drive shaft socket 180. The bearing optimally is a ball bearing which is held in place by a stop ring 174. The pegs 160 of the drive shaft carriage 150 are attached to and extend radially outwardly from the outer shell 152. The proximal end portion of the outer shell 152 includes an abutting surface 162 and two guiding surfaces 168 and 166. Both guiding surfaces are generally conical in shape, one of them being an outer guiding surface 168 and the other being an inner guiding surface 166.

The drive shaft socket 180 includes a tubular shaft 190, a disc 186 and a proximally extending engagement ring 182. The engagement ring 182 defines an interior engagement surface 184 of the socket 180. In a preferred embodiment, the interior engagement surface 184 of the socket 180 is generally cylindrical, but it may have a somewhat different shape, e.g. a generally frustoconical shape. The proximal surface of the disc 186 defines a proximally oriented face 188 of the drive shaft socket 180. In the illustrated embodiment, the tubular shaft 190 is comprised of an outer tubular shaft portion 192 and an inner tubular shaft portion 194. Desirably, the outer tubular shaft portion 192, the disc 186 and the engagement ring 182 are integrally formed as a single element while the inner tubular shaft portion 194 is formed as a separate element. The inner tubular shaft portion 194 is glued or otherwise attached to the rest of the drive shaft socket 180 for rotation therewith. If so desired, the entire drive shaft socket 180, including both portions of the tubular shaft, may be integrally formed as a single component.

Preferably, the inner tubular shaft portion 194 extends proximally of the face 188 of the disc 186 to define a central extension 196 of the socket. As shown in the drawings, this central extension 196 is tubular and includes a central lumen having the same diameter as the rest of the inner tubular shaft portion 194 so that the proximal portion 62 of the flexible drive shaft may extend proximally to the proximal end of the central extension 196 of the drive shaft socket 180. It should be understood that the central extension need not be tubular and it may be provided with a different outer shape, e.g. it may be conical in shape.

The carriage core 170 can be press fitted, glued or otherwise attached to the outer shell 152 of the drive shaft carriage 150. These components, as well as many other components shown as separate parts in the drawings may be integrally formed with one another.

As described in more detail below, fluid is supplied to the exchangeable drive shaft cartridge 80 distally of the drive shaft socket 180, and preferably adjacent the distal end of the longitudinally extendable tube 100. The distal end portion of the longitudinally extendable tube 100 is connected to the distal end piece 130 of the housing. A tubular proximal extension of the distal end piece 130 is connected to the tube comprising most of the length of the tubular housing 110 and defines the annular distal collar 132 of the tubular housing. A tubular distal extension 134 of the distal end piece 130 is adapted to receive a bulkhead 140 therein. The bulkhead 140 is disposed between and operatively connects the distal end portion of the longitudinally extendable tube 100 and the proximal end portion 72 of the catheter 70. The bulkhead 140 includes a fluid-receiving recess 144 positioned distally of a narrow opening 145 which defines a reduced diameter segment of the drive shaft lumen 85. As discussed more fully below (e.g., in connection with FIGS. 60–62), the bulkhead 140 also includes a passageway 142 through which fluid may enter the fluid-receiving recess 144 of the bulkhead 140.

The proximal end portion 72 of the catheter desirably has a flange 74 at its proximal end. This flange 74 may be held between the bulkhead 140 and a washer 146 to keep the catheter in place. In a preferred embodiment, the proximal end portion 72 of the catheter is supported by a strain relief 76 which abuts the washer 146. The bulkhead 140 and the washer 146 can be held in place by an end cap 152 which is attached to the tubular distal extension 134 of the distal end piece 130 of the tubular housing 110.

In the embodiment seen in FIGS. 24 and 25, the proximal end of the tubular housing 110 is provided with a plurality of proximally extending resilient tabs 114 which have inwardly-extending shoulders 116 adjacent their proximal ends. These tabs may all be integrally formed with the annular proximal collar 112 attached to the proximal end of the tubular housing 110. The outer shell 152 of the drive shaft carriage 150 is provided with a radially outwardly extending flange 154 and a groove 156 positioned proximally of the flange 154 for receiving the shoulders 116 of the resilient tabs 114 of the tubular housing 110.

In FIG. 24, the longitudinally extendable tube 100 is at its maximum length, wherein the outer telescoping tube 82 is moved proximally with respect to both the tubular housing 110 and the inner telescoping tube 90 until the stops 88 and 118 engage one another. In FIG. 25, however, the longitudinally extendable tube 100 is at its minimum length, wherein a majority of the length of the outer telescoping tube 82 has been received within the tubular housing 110. In this position, the shoulders 116 of the resilient tabs 114 are received in the groove 156 behind the flange 154, thereby releasably locking the drive shaft carriage 150 to the tubular housing 110. Since the shoulders 116 of the tabs 114 are free to circumferentially slide in the groove 156, the outer telescoping tube 82 is free to rotate with respect to both the tubular housing 110 and the inner telescoping tube 90 when the drive shaft carriage 150 is releasably locked to the tubular housing 110 of the drive shaft cartridge 80.

Figure 26:
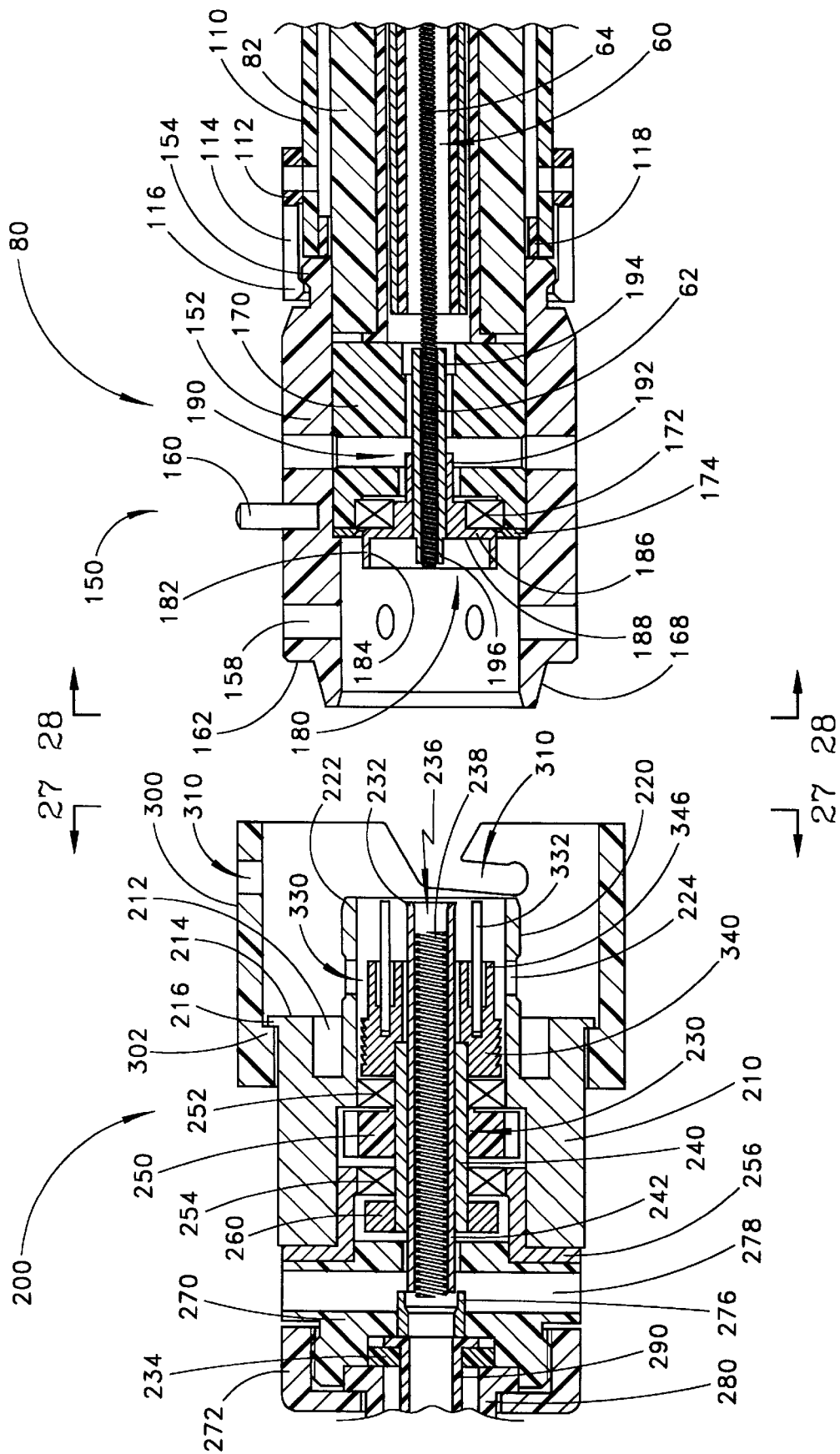
FIG. 26 is a broken-away, longitudinal cross sectional view showing the drive shaft carriage spaced away from the prime mover carriage.
Figure 27:
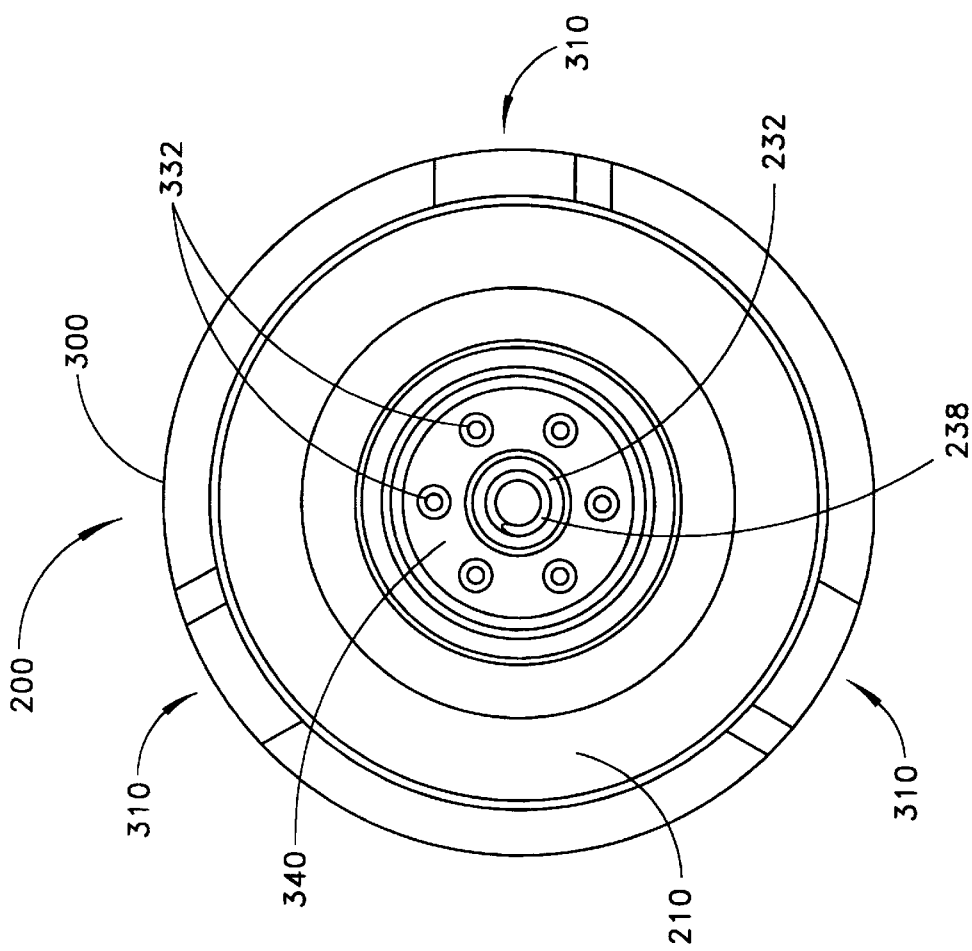
FIG. 27 is a schematic end view of the prime mover carriage taken along line 27—27 in FIG. 26.

The prime mover carriage 200 is shown in FIGS. 26 and 27. The prime mover carriage 200 includes a prime mover housing 210 which carries the bayonet collar 300 and the prime mover together with the prime mover coupling 330. The prime mover can be any device which can rotate the prime mover coupling 330 at sufficiently high speed. Preferably, though, the prime mover is a gas driven prime mover which generally comprises a turbine wheel 250 mounted on a prime mover shaft 230 for rotation therewith. The turbine wheel 250 is received in a turbine recess in the prime mover housing 210 and is driven by means of a compressed gas, e.g. air or nitrogen. As seen in FIG. 1, the preferred embodiment of the invention includes a flexible gas supply tube 36 which is attached to the distal portion 12 of the handle 10. This flexible gas supply tube 36 supplies compressed gas to a pneumatic guide wire clamp (not shown), which is retained in the distal portion 12 of the handle. The turbine wheel 250 is driven by compressed gas supplied through the flexible U-shaped linking tube 38, which is in fluid communication with the flexible gas supply tube 36. Gas driven turbines and pneumatic guide wire clamps are well known in the art (see, e.g., Auth et al. U.S. Pat. No. 5,314,407, the teachings of which are incorporated herein by reference) and need not be discussed in detail here.

The prime mover shaft 230 can be integrally formed as a single elongate tube. In the embodiment shown in FIG. 26, though, the prime mover shaft 230 includes a shorter outer tubular portion 240 and a longer inner tubular portion 242. The turbine wheel 250 is mounted on the outer tubular portion 240 of the prime mover shaft. The inner tubular portion 242 of the prime mover shaft is secured (e.g., glued) within the outer tubular portion 240. The longer inner tubular portion 242 extends both distally and proximally of the shorter outer tubular portion 240. The longer inner tubular portion 242 defines a guide wire lumen 236 of the prime mover shaft. In the embodiment shown in the drawings, a helically wound coil 238 is disposed within the guide wire lumen 236 of the prime mover shaft. The coil 238 is rotatable together with the prime mover and is desirably oriented such that it will urge fluid proximally when the prime mover is rotated. The distal end 232 of the inner tubular portion 242 of the prime mover shaft is flared outwardly so that a proximal length of the central extension 196 of the drive shaft socket 180 can slide more easily into the guide wire lumen 236 of the prime mover shaft 230.

The prime mover shaft 230 is desirably supported within the prime mover housing 210 by at least one bearing. Preferably, the prime mover shaft 230 is supported by two bearings, one of which is positioned distally and the other of which is positioned proximally of the turbine wheel 250 of the prime mover. Both the distal bearing 252 and the proximal bearing 254 are mounted on the outer tubular portion 240 of the prime mover shaft. A coupling base 340 of the rotatable, radially expandable prime mover coupling 330 is secured to the prime mover shaft 230 distally of the distal bearing 252. In the illustrated embodiment, the coupling base 340 is attached to the outer tubular portion 240 of the prime mover shaft 230. In the embodiment shown in FIG. 26, the prime mover coupling 330 includes at least two flexible pins 332 which are anchored adjacent their proximal ends to the coupling base 340. As seen in FIG. 27, there are six pins 332 and they are spaced equiangularly about the axis of the coupling base 340.

A rotor 260 of an optical tachometer is mounted on the prime mover shaft proximally of the proximal bearing 254. In the illustrated embodiment, the rotor 260 is mounted on the outer tubular portion 240 of the prime mover shaft 230. The outer surface of the rotor 260 may include a pair of diametrically opposed concave reflectors (262 in FIG. 60). As detailed in U.S. Pat. No. 5,314,407, a rotor having diametrically opposed reflective areas can be used in conjunction with a pair of fiber optic cables (264 in FIG. 1, for example) to monitor the rotational speed of the prime mover.

The bearings 252 and 254 can be attached to the prime mover housing 210 to support the prime mover shaft 230. In the embodiment shown in FIG. 26, the distal bearing 252 is attached directly to the prime mover housing 210 while the proximal bearing 254 is attached to a proximal bearing support 256 which is, in turn, attached to the proximal end portion of the prime mover housing 210.

A proximal bulkhead 270 of the prime mover carriage 200 is secured to the prime mover housing 210. This can be done either by gluing the proximal bulkhead 270 to the proximal bearing support 256 or by passing screws through holes in the proximal bearing support and securing the screws directly to the prime mover housing 210. Two moveable proximal telescoping tubes 280 and 290 are secured to and extend proximally from the proximal bulkhead 270. The tubes may be secured to the proximal bulkhead 270 by a proximal cap 272 and a ring 234. As described in more detail below in connection with FIG. 64, for example, both of the proximal telescoping tubes are slidably received in the proximal portion 12 of the handle. The proximal bulkhead 270 also carries a short collar 276. The distal end of the short collar 276 is in fluid communication with the proximal end of the guide wire lumen 236 of the prime mover shaft 230 while the proximal end of the short collar 276 is in fluid communication with the proximal inner telescoping tube 290. Desirably, a small gap is provided between the short collar 276 and the proximal end of the inner tubular portion 242 of the prime mover shaft so the guide wire lumen 236 of the prime mover shaft may also be in fluid communication with a fluid drainage outlet 278 in the proximal bulkhead 270.

The prime mover housing 210 includes a distally-facing abutting surface 214 which is adapted to abut the abutting surface 162 of the outer shell 152 of the drive shaft carriage. A proximally extending annular recess 212 may be positioned radially inwardly of this abutting surface 214 to receive the proximal end portion of the outer shell 152 of the drive shaft carriage 150. A flange 216 may extend radially outwardly from the distal portion of the prime mover housing 210 to engage an interior shoulder 302 adjacent the proximal end of the bayonet collar 300.

The prime mover housing 210 also includes a guiding sleeve 220 which extends distally beyond the abutting surface 214 of the prime mover housing 210 to surround and protect the prime mover coupling 330. This guiding sleeve 220 is sized to be slidably received within the outer shell 152 of the drive shaft carriage and helps to align the prime mover coupling 330 with the drive shaft socket 180. To facilitate easy entry of the guiding sleeve 220 into the outer shell 152 of the drive shaft carriage, the distal end 222 of the guiding sleeve may be beveled.

FIGS. 18–20, discussed above, are top views schematically illustrating how one may interconnect the drive shaft carriage 150 and the prime mover carriage 200. As explained previously, this is accomplished by aligning the pegs 160 with the inlets 312 of the slots 310 of the bayonet collar and moving the two carriages 150 and 200 toward one another. Once the pegs 160 are received in the inlets 312 of the slots 310, the bayonet collar and the drive shaft carriage can be rotated with respect to one another until each of the pegs is seated in a recess 320 formed in the anterior wall 318 of the leg 322 of a slot 310.

FIGS. 26 and 29–31 illustrate essentially the same process of interconnecting the carriages 150 and 200, but in a longitudinal cross sectional view which shows the positions of the prime mover coupling 330 and the drive shaft socket 180. These drawings show how the drive shaft carriage 150 and the prime mover carriage 200 can be moved longitudinally from a non-operational position wherein the prime mover coupling 330 is spaced from the drive shaft socket 180 (FIG. 26) to an operational position wherein a length of the prime mover coupling 330 is received within the drive shaft socket 180 (e.g., FIG. 31). In the operational position shown in FIG. 31, the drive shaft carriage 150 and the prime mover carriage 200 are interconnected to move together as a unit to move the drive shaft 60 and its tissue removal implement (68 in FIG. 1, for example) along a vascular lumen of a patient's body (not shown).

Figure 29:
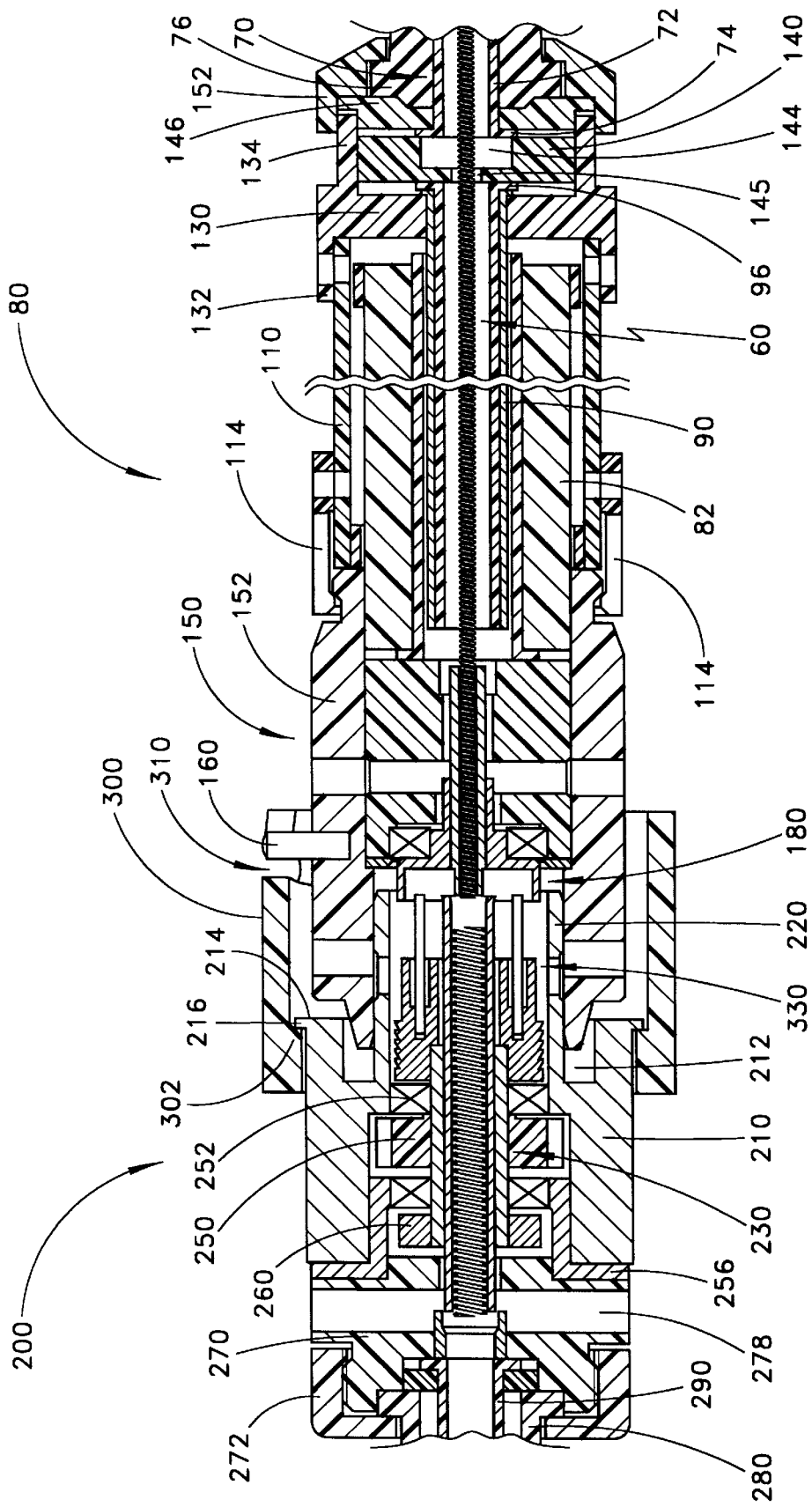
FIGS. 29–31 are longitudinal cross sections illustrating the process of interconnecting the drive shaft carriage and the prime mover carriage.
Figure 30:
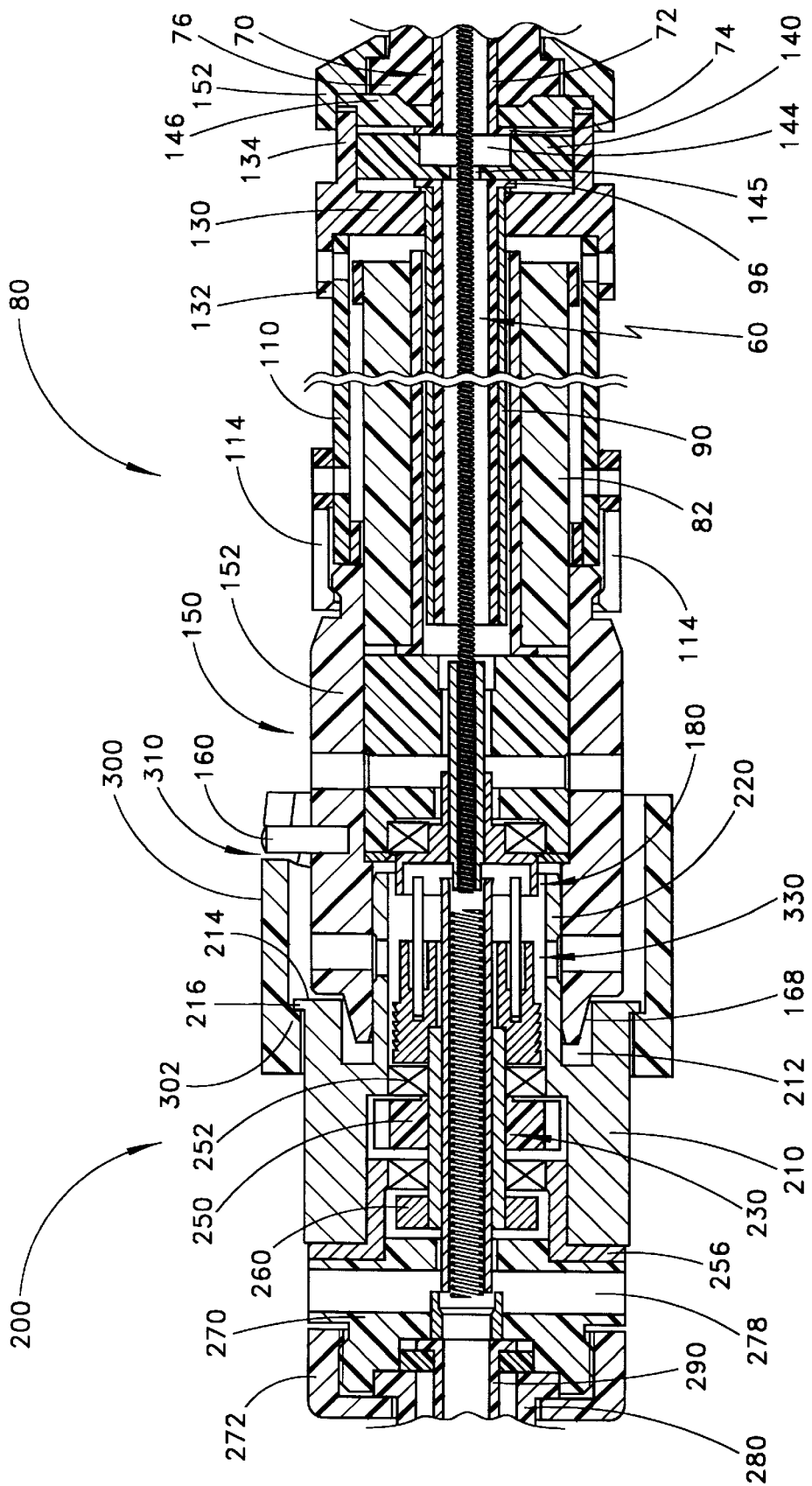
Figure 31:
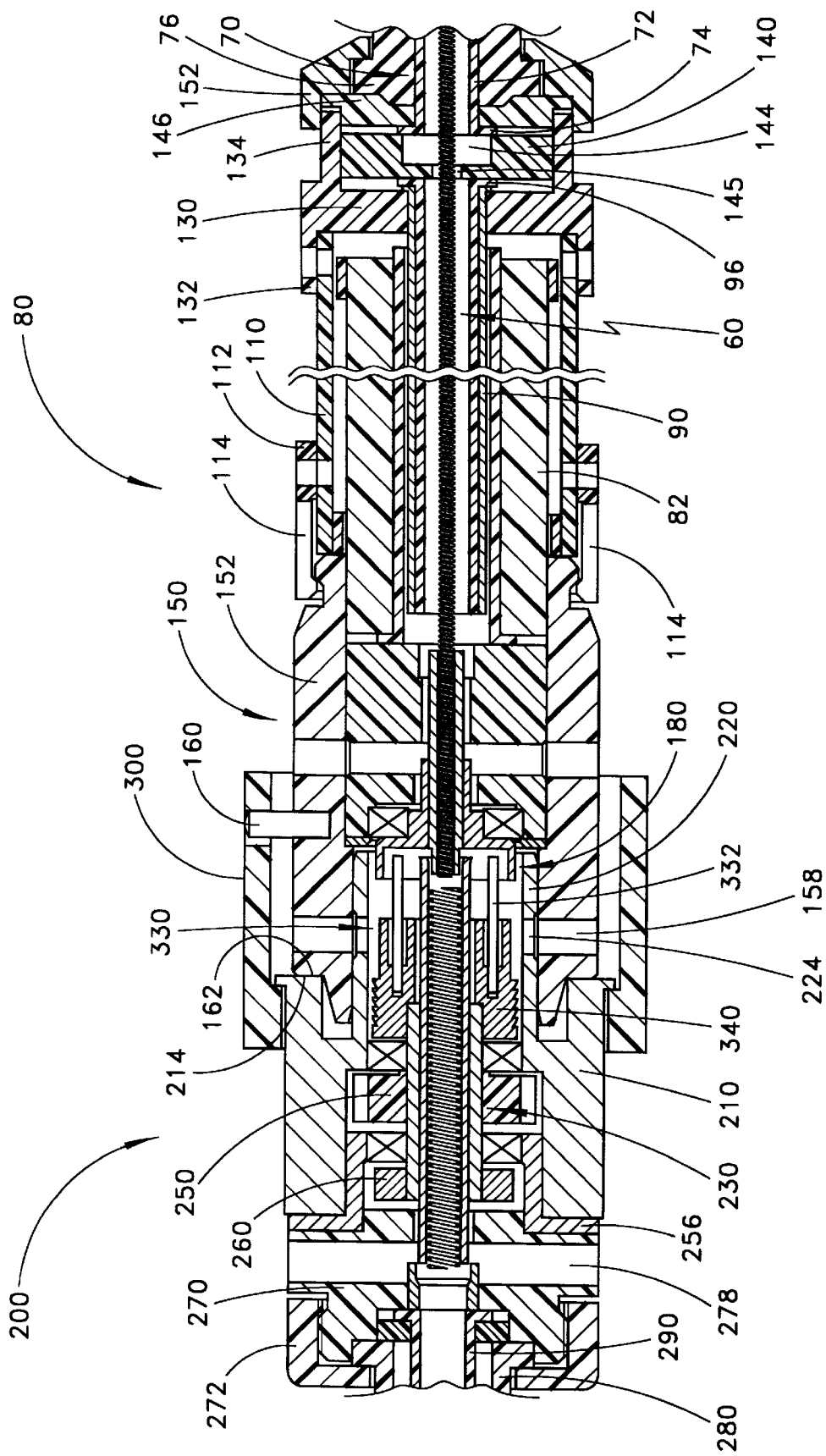

In moving from the position shown in FIG. 26 to the position shown in FIG. 29, the drive shaft carriage 150 and the prime mover carriage 200 are moved longitudinally toward one another. In so doing, the guiding sleeve 220 of the prime mover housing 210 is slidably received within a proximal length of the outer shell 152 of the drive shaft carriage 150. As noted above, the distal end 222 of the guiding sleeve 220 is beveled and the proximal end portion of the outer shell 152 includes a conical inner guiding surface 166. This beveled end 222 and the inner guiding surface 166 facilitate easy entry of the guiding sleeve 220 into the outer shell 152 of the drive shaft carriage. The guiding sleeve 220 should be sized to be fairly closely received within the outer shell 152 of the drive shaft carriage. As shown in FIGS. 29–31, the outer surface of the guiding sleeve 220 can thus slide against the inner surface of the outer shell 152 to align the prime mover coupling 330 with the drive shaft socket 180.

Turning to FIG. 29, the pegs 160 of the drive shaft carriage have just been received in the inlets of the slots 310 in the bayonet collar 300. (In the cross sectional view of FIGS. 29–31, only a single peg 160 and a single slot 310 are visible, but there are three pegs 160 and three slots 310 in the illustrated embodiment.) In this position, a majority of the length of the guiding sleeve 220 is received within the outer shell 152 of the drive shaft carriage 150 and the proximal end portion of the outer shell 152 is starting to be received in the annular recess 212 in the prime mover housing 210. The free distal ends of the pins of the prime mover coupling 330 have also started to be received within the drive shaft socket 180.

In FIG. 30, the bayonet collar 300 has been rotated about the prime mover housing 210 (a central element of the prime mover carriage 200) to slide the pegs 160 of the drive shaft carriage along the anterior wall (318 in FIGS. 18–21) of the slot 310. In a preferred embodiment, the closed end of the leg 322 of each slot is positioned proximally of the inlet end of the leg. As a result, the pegs 160 of the drive shaft carriage 150 will slide along the anterior walls of the slots 310 as the bayonet collar 300 is rotated, urging the pins 160 proximally with respect to the bayonet collar 300.

As the pins 160 of the drive shaft carriage move proximally with respect to the bayonet collar 300, the interior shoulder 302 of the bayonet collar will pull against the flange 216 of the prime mover housing 210. As a result, the pegs 160 and the bayonet collar 300 move the drive shaft carriage 150 and the prime mover carriage 200 closer to one another. As shown in FIG. 30, this will cause the proximal end portion of the outer shell 152 of the drive shaft carriage 150 to be more fully received in the annular recess 212 of the prime mover housing 210. Desirably, the proximal end portion of the outer shell 152 includes a conical outer guiding surface 168 which may help more precisely align the carriages 150 and 200 with respect to one another. FIG. 30 also shows the central extension of the drive shaft socket 180 starting to be received in the guide wire lumen of the prime mover shaft 230. The flared distal end of the prime mover shaft 230 will help guide the central extension of the drive shaft socket 180 into place even if these two parts are slightly misaligned.

FIG. 31 illustrates the drive shaft carriage 150 and the prime mover carriage 200 interconnected in an operational position. In FIG. 31, the bayonet collar 300 has been rotated until each of the pegs 160 has been seated in a small recess 320 in the anterior wall 318 at the closed end of a slot 310. (The slot 310 and its elements are better seen in FIGS. 18–21, for example.) In this position, the abutting surface 162 of the outer shell 152 of the drive shaft carriage 150 is pressed against the abutting surface 214 of the prime mover housing 210. In a preferred embodiment, the pegs 160 are formed of a resilient material, such as a resilient plastic or a metal. When the pegs 160 of the drive shaft carriage 150 slide along the anterior walls 318 of the slots 310, the free end of each peg 160 may deflect slightly proximally with respect to the other end, which is attached to the outer shell 152 of the drive shaft carriage. As a result, the pegs 160 act as leaf springs, urging the bayonet collar 300 distally and pressing the abutting surfaces 162 and 214 against one another.

In FIG. 31, the central extension of the drive shaft socket 180 is more fully received within the guide wire lumen of the prime mover shaft 230. This ensures that the guide wire lumen of the drive shaft 60 is in fluid communication with the guide wire lumen of the prime mover shaft 230 while minimizing leakage at this junction. In addition, the fluid drainage outlets 224 in the guiding sleeve 220 are in fluid communication with the proximal fluid drainage outlets 158 in the outer shell 152 of the drive shaft carriage. Preferably, the fluid drainage outlets 224 of the guiding sleeve 220 open into a shallow circumferential groove 226 (better seen in FIGS. 36–39, for example) in the guiding sleeve 220. This shallow circumferential groove 226 maintains fluid communication between the fluid drainage outlets 224 and 158 so long as the fluid drainage outlets 224 of the guiding sleeve 220 are longitudinally aligned with the proximal fluid drainage outlets 158 of the outer shell 152. The shallow circumferential groove 226 eliminates the need for the fluid drainage outlets 224 of the guiding sleeve 220 to be axially aligned with the proximal fluid drainage outlets 158 of the outer shell 152 to ensure proper fluid drainage from the guiding sleeve 220.

As can be seen in FIG. 31, the free ends of the flexible pins 332 of the prime mover coupling 330 have been received within the drive shaft socket 180. The pins 332 of the prime mover coupling 330 do not contact the interior engagement surface of the drive shaft socket 180. Desirably, the pins 332 do not contact any part of the interior surface of the drive shaft socket 180. More importantly, the prime mover coupling 330 should not effectively engage an interior surface of the drive shaft socket 180 when the prime mover coupling 330 is not rotating.

Figure 32:
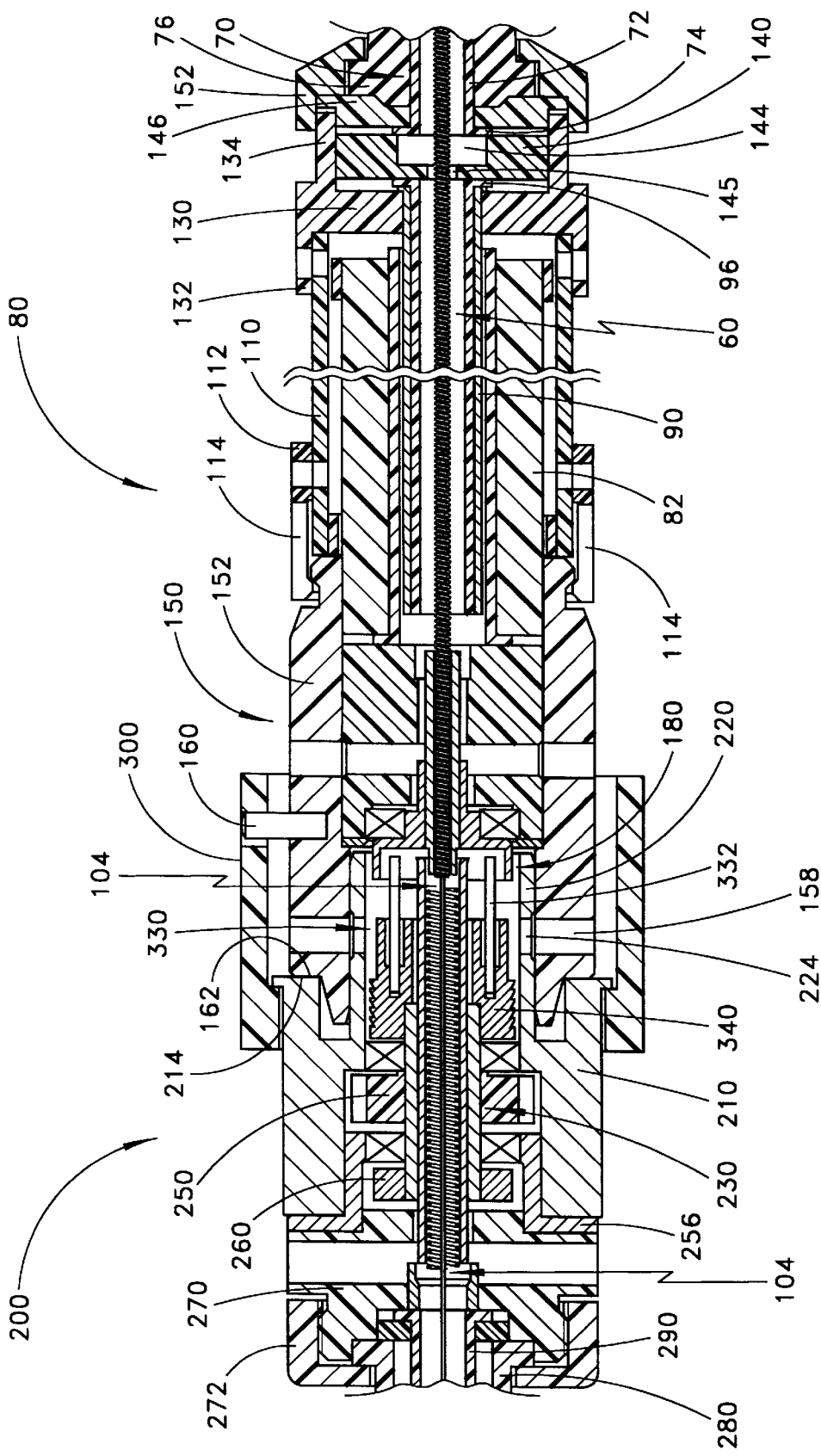
FIG. 32 is similar to FIG. 31, but wherein the rotational atherectomy device has been advanced over a guide wire.

FIG. 32 is similar to FIG. 31, but the rotational atherectomy device has been advanced over a guide wire 104. In particular, the guide wire 104 extends through the guide wire lumen of the drive shaft 60, the guide wire lumen of the prime mover shaft 230, the lumen of the short collar 276, and the lumen of the proximal inner telescoping tube 290.

Figure 33:
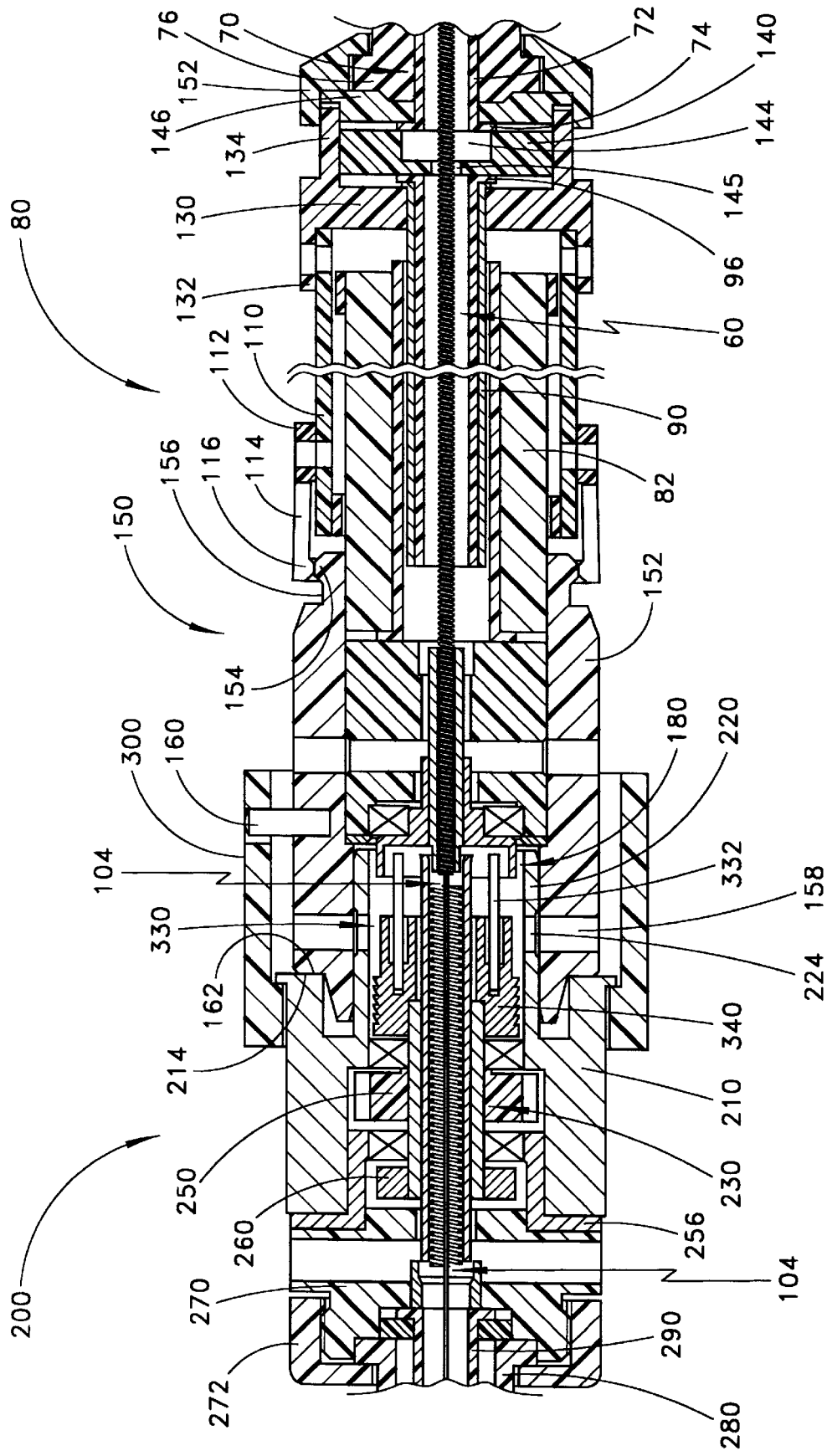
FIG. 33 is a longitudinal cross sectional view similar to FIG. 32 showing the interconnected drive shaft and prime mover carriages being moved proximally to a position where the interlocking elements of the drive shaft cartridge become disconnected.

FIG. 33 is a longitudinal cross sectional view similar to FIG. 32, but showing the interconnected drive shaft carriage 150 and prime mover carriage 200 being moved proximally to a position where the drive shaft carriage 150 is disconnected from the tubular housing 110 of the exchangeable drive shaft cartridge 80. In particular, the interconnected carriages 150 and 200 have been moved proximally so that the proximal ends of the resilient tabs 114 have deflected radially outwardly and the shoulders 116 of the tabs are sliding over the top of the flange 154 carried by the outer shell 152 of the drive shaft carriage.

Figure 34:
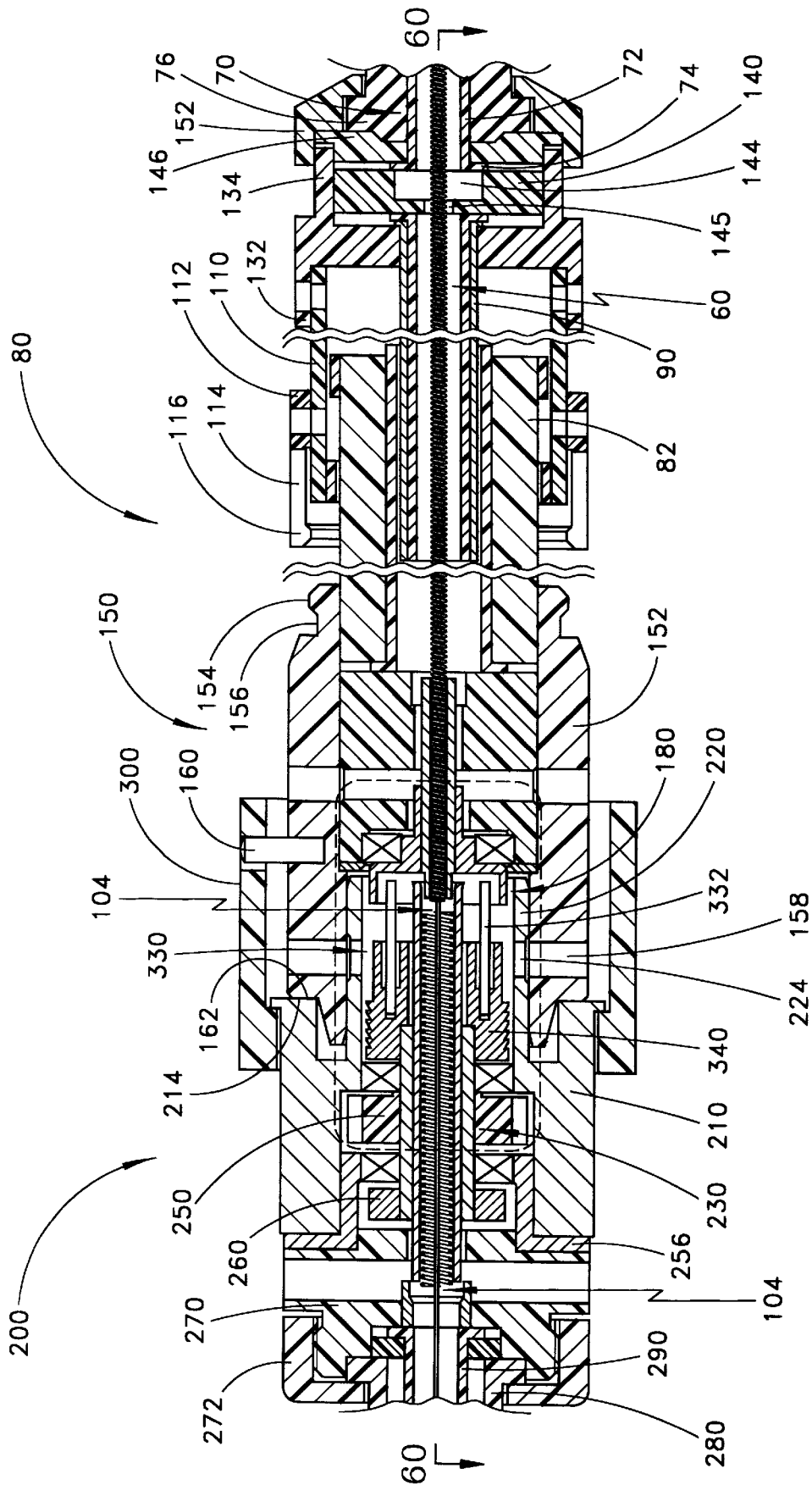
FIG. 34 is a longitudinal cross sectional view similar to FIG. 33 showing the interlocking elements of the exchangeable drive shaft cartridge spaced away from one another.
Figure 35:
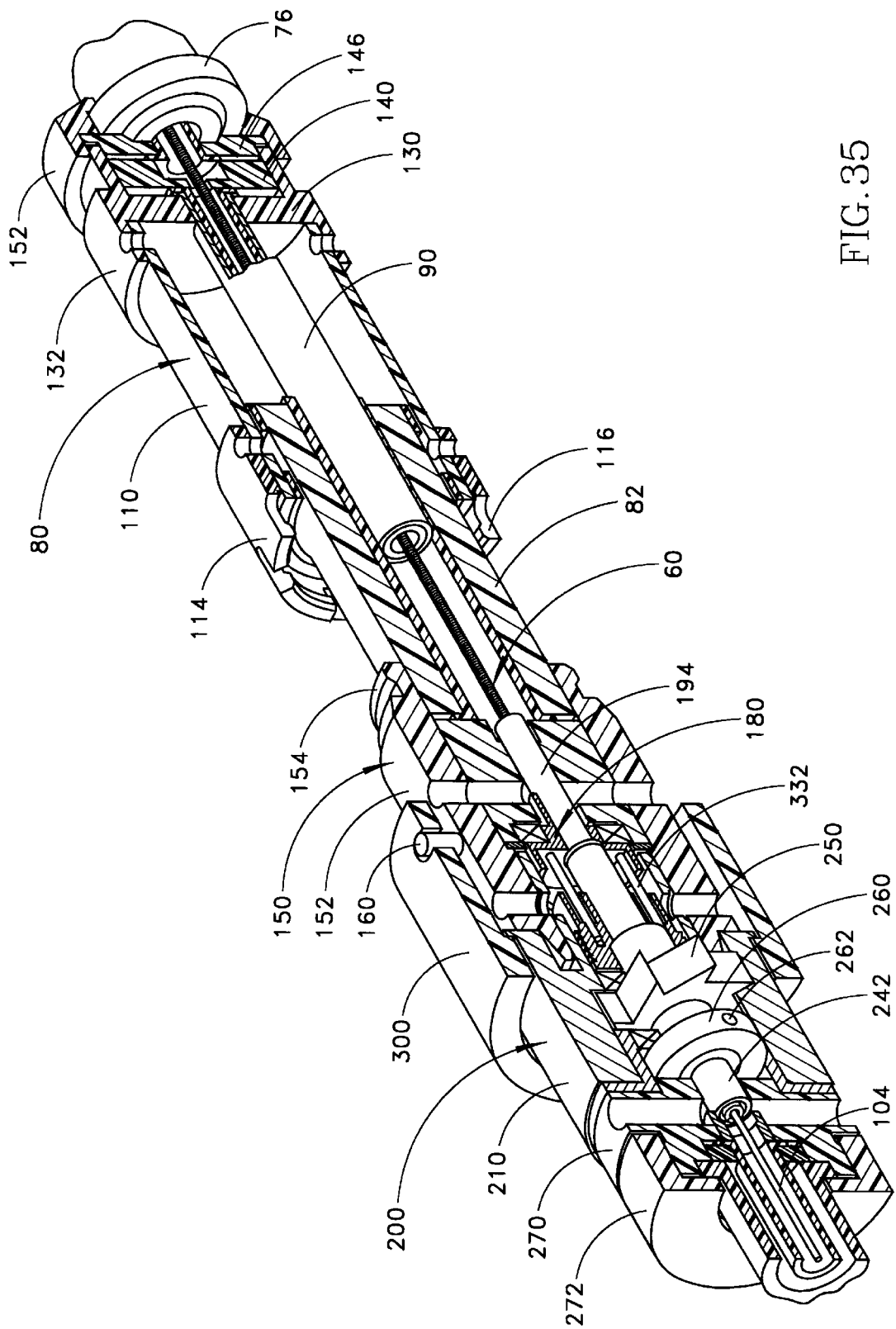
FIG. 35 is a longitudinal cross section similar to FIG. 34, but illustrating the device in a perspective view.

FIG. 34 is a longitudinal cross sectional view similar to FIG. 33 showing the drive shaft carriage 150 disconnected from the tubular housing 110 of the exchangeable drive shaft cartridge 80 and moved proximally away from the tubular housing 110. FIG. 35 is similar to FIG. 34, but shows the device in a perspective cross sectional view. This perspective view is advantageous in that it affords a better view of many of the components, particularly the turbine wheel 250 and the rotor 260 of the optical tachometer.

Figure 36:
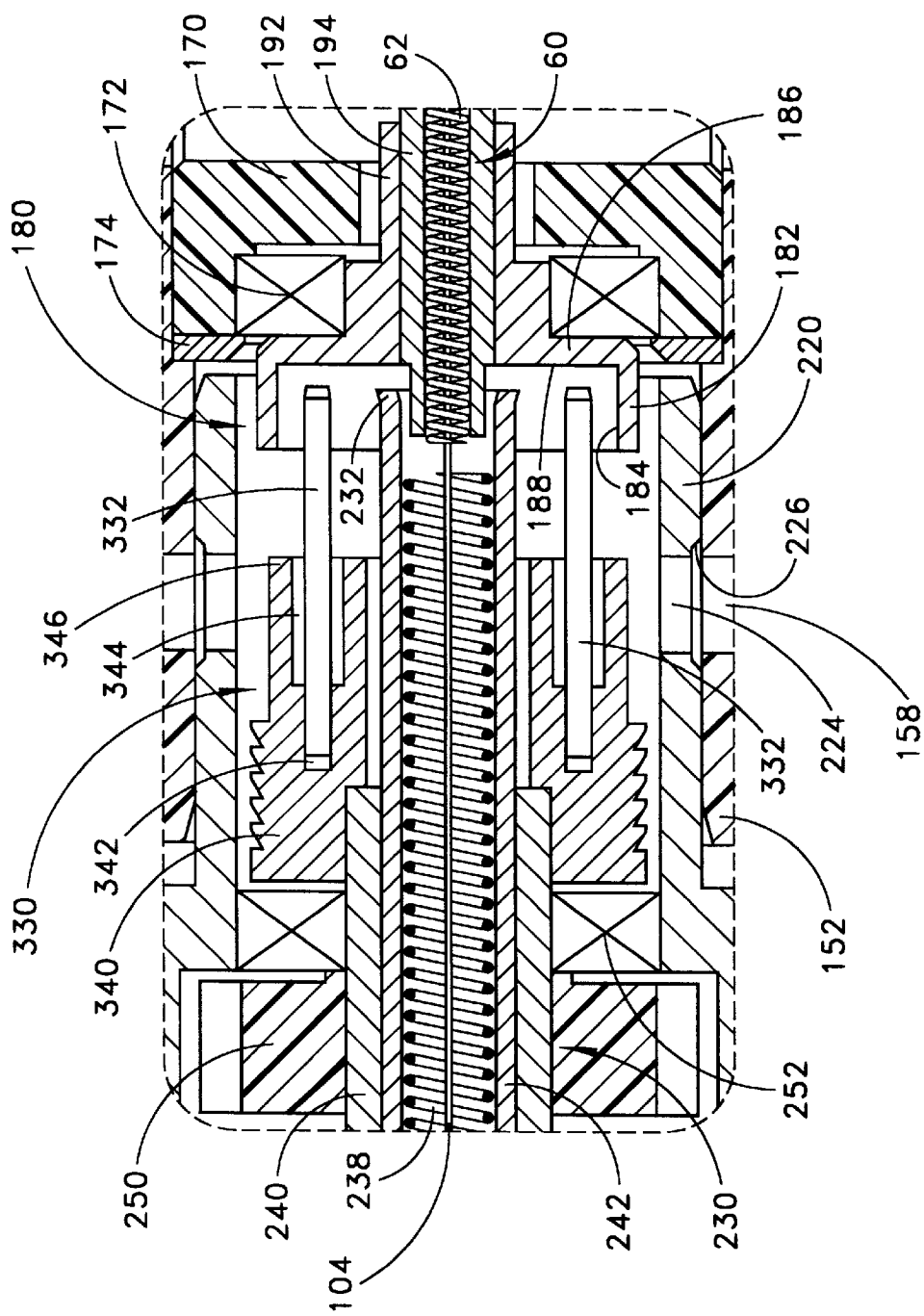
FIG. 36 is an enlarged view of the section outlined in FIG. 34 illustrating that the flexible pins of the prime mover coupling do not contact an interior surface of the drive shaft socket when the prime mover is not rotating.
Figure 37:
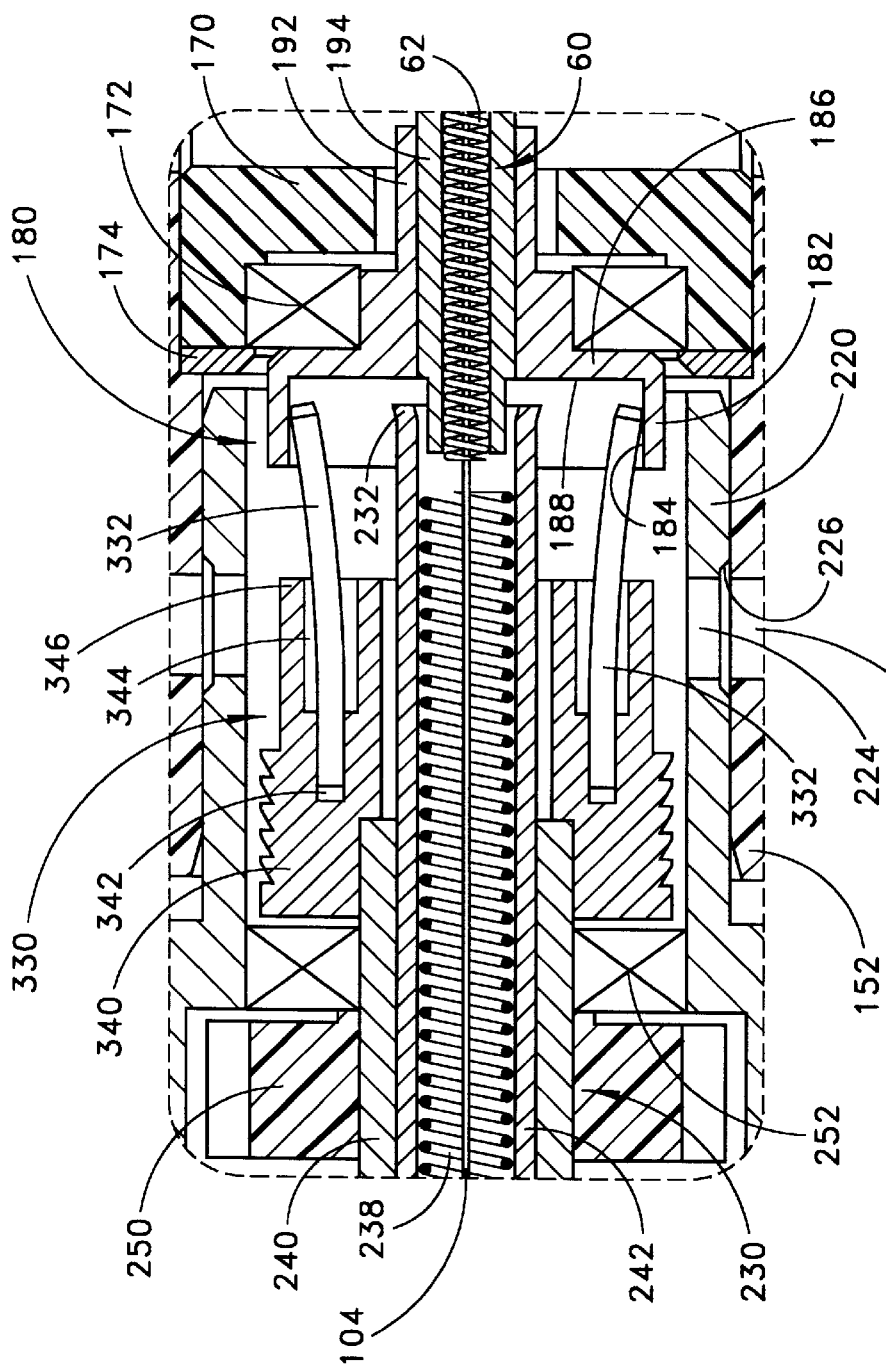
FIGS. 37–39 illustrate how the flexible pins of the prime mover coupling deflect into frictional engagement with the interior surface of the drive shaft socket upon increasingly rapid rotation of the prime mover.
Figure 38:
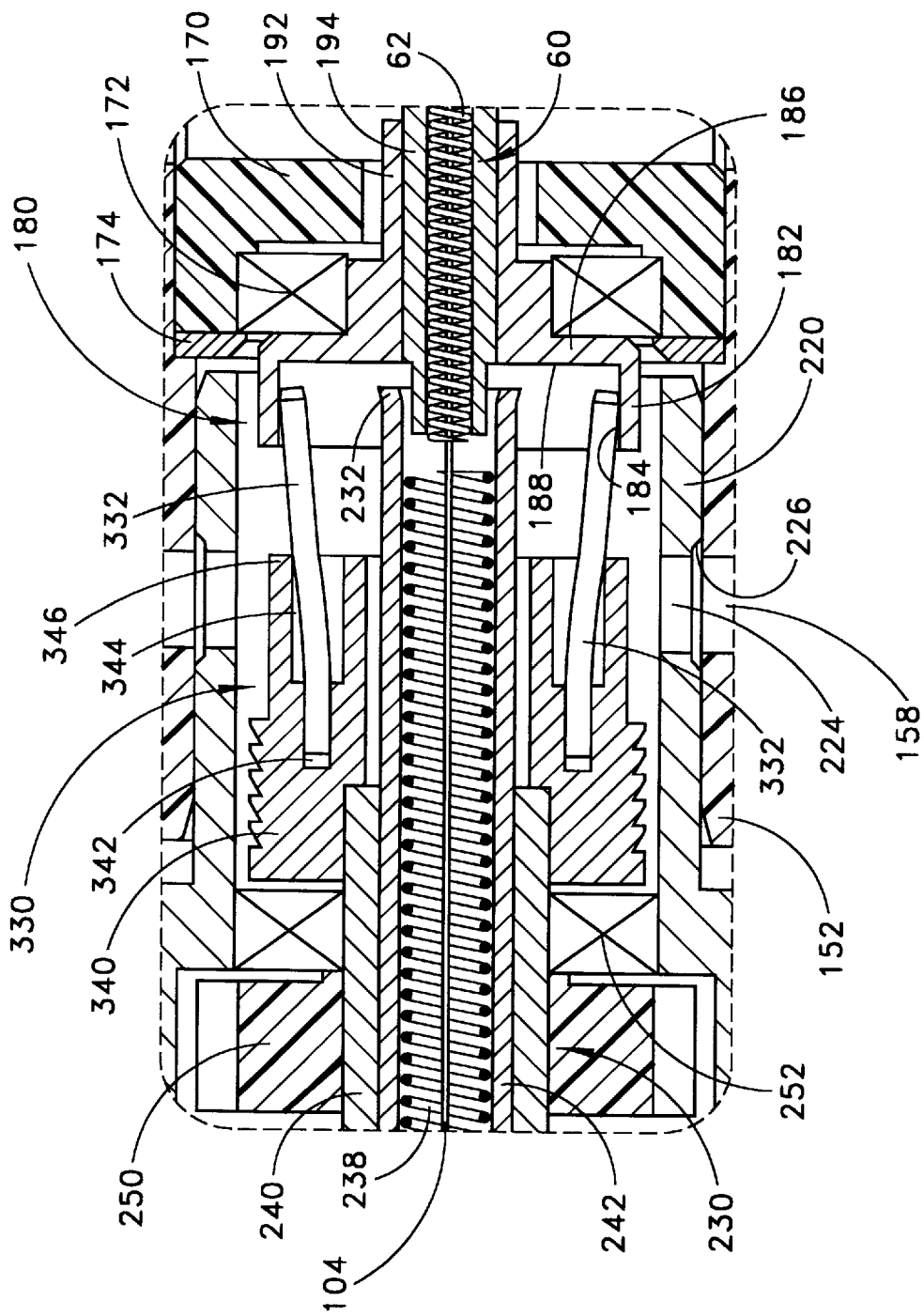
Figure 39:
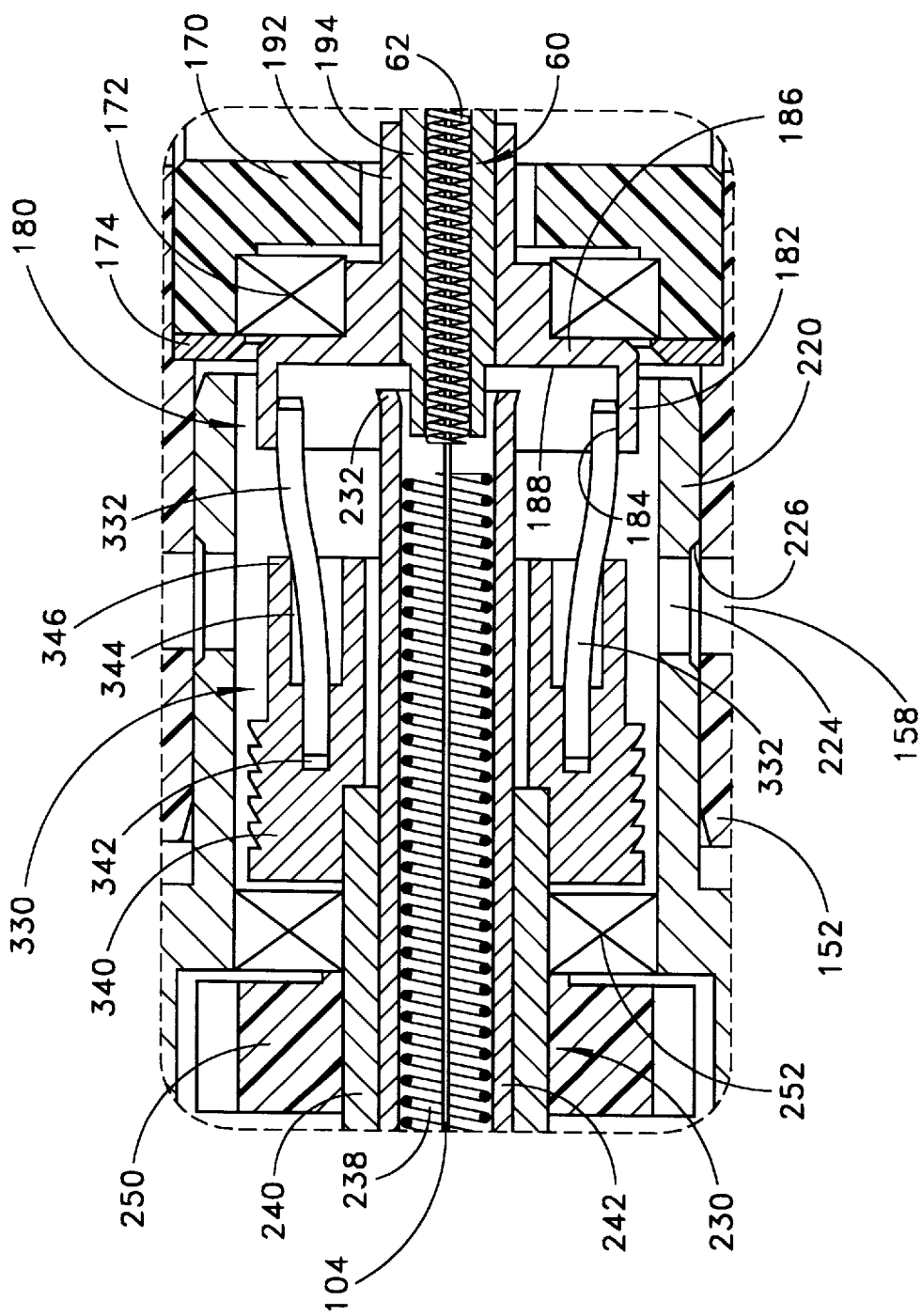

FIGS. 36–39 schematically illustrate operation of one embodiment of a prime mover coupling 330 of the invention. FIG. 36 is an enlarged view of the outlined section of FIG. 34 when the prime mover and the prime mover coupling 330 are not rotating while FIGS. 37–39 schematically show what happens upon increasingly rapid rotation of the prime mover and the prime mover coupling 330.

The prime mover coupling 330 of FIGS. 36–39 generally comprises a coupling base 340 and at least two flexible pins 332. Desirably, there are at least six flexible pins and the pins are spaced equiangularly about an axis of the coupling base. Preferably, these pins 332 are formed of a superelastic material, e.g., nitinol, an alloy of nickel and titanium which is well known and widely used in the medical device industry. Each flexible pin 332 is anchored to the coupling base 340 adjacent one end and has a free end which is free to deflect radially outwardly to effectively engage the drive shaft socket 180 when the prime mover is rotated. In the embodiment of FIGS. 26–29, the coupling base 340 includes a plurality of proximally extending bores 342. Each bore 342 receives the anchored end portion of a flexible pin 332 and the pins may be press-fitted in place.

An intermediate portion of each flexible pin 332 is received in a counterbore 344 in the coupling base 340. The inner diameter of each counterbore 344 is greater than the outer diameter of the pin received therein. As explained more fully below, the wall 346 of each counterbore 344 serves as an abutment to limit outward deflection of an intermediate point along the length of the flexible pin 332.

The coupling base 340 can be formed of any suitable material; stainless steel has been found to work well. If so desired, the flexible pins 332 may be integrally formed with the coupling base 340. In this case, the coupling base should also be formed of a superelastic material, e.g., nitinol. In the illustrated embodiment, the coupling base 340 is attached to the distal end portion of the outer tubular portion 240 of the prime mover shaft 230. If so desired, though, the coupling base 340 can be integrally formed with the prime mover shaft 230. To further reduce the number of components, the prime mover shaft 230, the coupling base 340 and the flexible pins 332 all can be integrally formed as a single component.

In the embodiment shown in FIGS. 36–39, each flexible pin 332 is anchored adjacent a proximal end to the coupling base 340 and has a distal end which is free to deflect radially outwardly to engage the interior engagement surface 184 of the engagement ring 182 of the drive shaft socket 180 when the prime mover is rotated. It should be understood, though, that the flexible pins 332 can be oriented differently so that their distal ends are anchored to the coupling base 340 and the proximal ends of the pins can be free to deflect into engagement with the interior surface of the drive shaft socket 180. Such an embodiment is less desirable, though, because it would require a much longer engagement ring 182.

The precise dimensions of the components of the prime mover coupling 330 and the drive shaft socket 180 can be varied as necessary to achieve the desired performance characteristics, e.g., the rotational speed at which the flexible pins 332 of the prime mover coupling 330 effectively engage the drive shaft socket 180 and the torque which is conveyed from the prime mover coupling 330 to the drive shaft socket 180. One embodiment has been found useful for use in connection with a rotational atherectomy device which is intended to be operated in a broad range of operational speeds, e.g., from about 20,000 to about 200,000 revolutions per minute (rpm). In this exemplary embodiment, the flexible pins 332 are formed of round nitinol wire having a diameter of about 0.77 mm (about 0.03 inches). The pins 332 are about 13 mm long, with about 2.5 mm being press fitted in the bore 342 in the coupling base 340, about 4.5 mm being received in the counterbore 344 in the coupling base, and about 6 mm extending distally beyond the distal end of the counterbore 344. The distal ends of the flexible pins 332 are beveled, as shown. There are six such pins spaced equiangularly about the axis of the coupling base and the distance between the axes of diametrically opposed pins is about 3.9 mm. The counterbores 344 in the coupling base each have a diameter of about 0.9 mm. The inner tubular portion 242 of the prime mover shaft 230 has an inner diameter of about 1.07 mm.

The drive shaft socket 180 of this embodiment has an engagement ring 182 which extends proximally from the proximally oriented face 188 of the socket about 3.0 mm and has an inner diameter of about 4.8 mm. The engagement ring 182 has a smooth interior engagement surface 184. The central extension 196 of the drive shaft socket 180 has an outer diameter of about 0.9 mm and extends proximally of the proximally oriented face 188 of the socket about 2.5 mm.

When the prime mover carriage 200 and drive shaft carriage 150 are assembled in their operational position illustrated in FIG. 36, the distal end of the coupling base 340 is spaced about 3.5 mm from the proximal end of the engagement ring 182 so that about 2.5 mm at the distal end of each pin is received within the drive shaft socket 180. The clearance between the flexible pins 332 and the interior engagement surface 184 of the engagement ring 182 is about 0.065 mm. About 0.5 mm of the central extension 196 of the drive shaft socket 180 is received within the inner tubular portion 242 of the prime mover shaft. Since the inner diameter of the inner tubular portion 242 of the prime mover shaft is slightly larger than the outer diameter of the central extension 196 of the drive shaft socket 180, there should be a small clearance between these two parts.

When the prime mover is rotated, the free ends of the flexible pins 332 will deflect radially outwardly. FIG. 37 illustrates the beveled distal ends of the flexible pins 332 coming into contact with the interior engagement surface 184 of the engagement ring 182. In the specific embodiment detailed immediately above, one would expect to see such deflection at lower rotational speeds of the prime mover, e.g., about 18,000 to about 22,000 rpm.

FIG. 38 illustrates the pins 332 deflected further, with an intermediate point along the length of each flexible pin 332 contacting the distal end of the wall of the counterbore 344. In the specific embodiment detailed above, one would expect the flexible pins 332 to deflect into contact with the walls of the counterbores 344 at rotational speeds of about 100,000 rpm. The wall 346 of each counterbore 344 serves as an abutment to limit outward deflection of the intermediate point of the flexible pin 332. Support provided by this abutment helps to achieve appropriate frictional engagement between the pins 332 and the drive shaft socket 180 throughout a relatively wide range of rotational speeds of the prime mover.

FIG. 39 illustrates how the flexible pins 332 deflect when the prime mover is rotated at higher speeds. At these speeds, a significant length of a distal end portion of each pin 332 contacts the interior engagement surface 184 of the engagement ring 182, thereby providing maximum frictional contact between the pins and the interior surface of the drive shaft socket 180. This assures that upon sufficiently rapid rotation of the prime mover, the pins 332 of the prime mover coupling 330 will effectively engage the interior surface of the drive shaft socket 180 so the drive shaft socket 180 and the drive shaft 60 will rotate together with the prime mover coupling 330 and the prime mover. In the specific embodiment detailed above, one would expect to see the pins 332 to deflect as shown in FIG. 39 at rotational speeds in excess of about 180,000 rpm. It should be understood, though, that very reliable frictional engagement between the pins 332 of the prime mover coupling 330 and the drive shaft socket 180 takes place at much lower rotational speeds.

In the specific embodiment detailed above reliable frictional engagement between the pins of the prime mover coupling and the drive shaft socket usually is achieved at rotational speeds in the range of 35,000 to 40,000 rpm. By changing dimensions of the elements of the prime mover coupling and the drive shaft socket, one can readily vary the range of operational speeds throughout which one can achieve very reliable frictional engagement between the pins 332 and the socket 180. For example, using flexible pins 332 of a smaller diameter and/or a longer length will decrease the rotational speeds necessary to achieve very reliable frictional engagement between the pins and the drive shaft socket. The same result also can be achieved by reducing the clearance between the flexible pins 332 and the engagement ring 182 of the drive shaft socket.

When the prime mover is no longer rotated, the flexible pins 332 of the prime mover coupling 330 will tend to resiliently regain their original, non-deflected state, as shown in FIG. 36, thereby disconnecting the prime mover coupling 330 from the drive shaft socket 180. This disconnects the drive shaft 60 from the prime mover so the exchangeable drive shaft cartridge 80 can be replaced by another exchangeable drive shaft cartridge having a tissue removal implement of a different size or a different design.

Deflection of the pins 332 radially outwardly upon rotation of the prime mover can be viewed as radial expansion of the prime mover coupling 330. When the prime mover stops rotating and the flexible pins 332 regain their original shape, the prime mover coupling 330 regains a radially reduced dimension, thereby disconnecting the drive shaft socket 180 and the drive shaft 60 from the prime mover.

Figure 40:
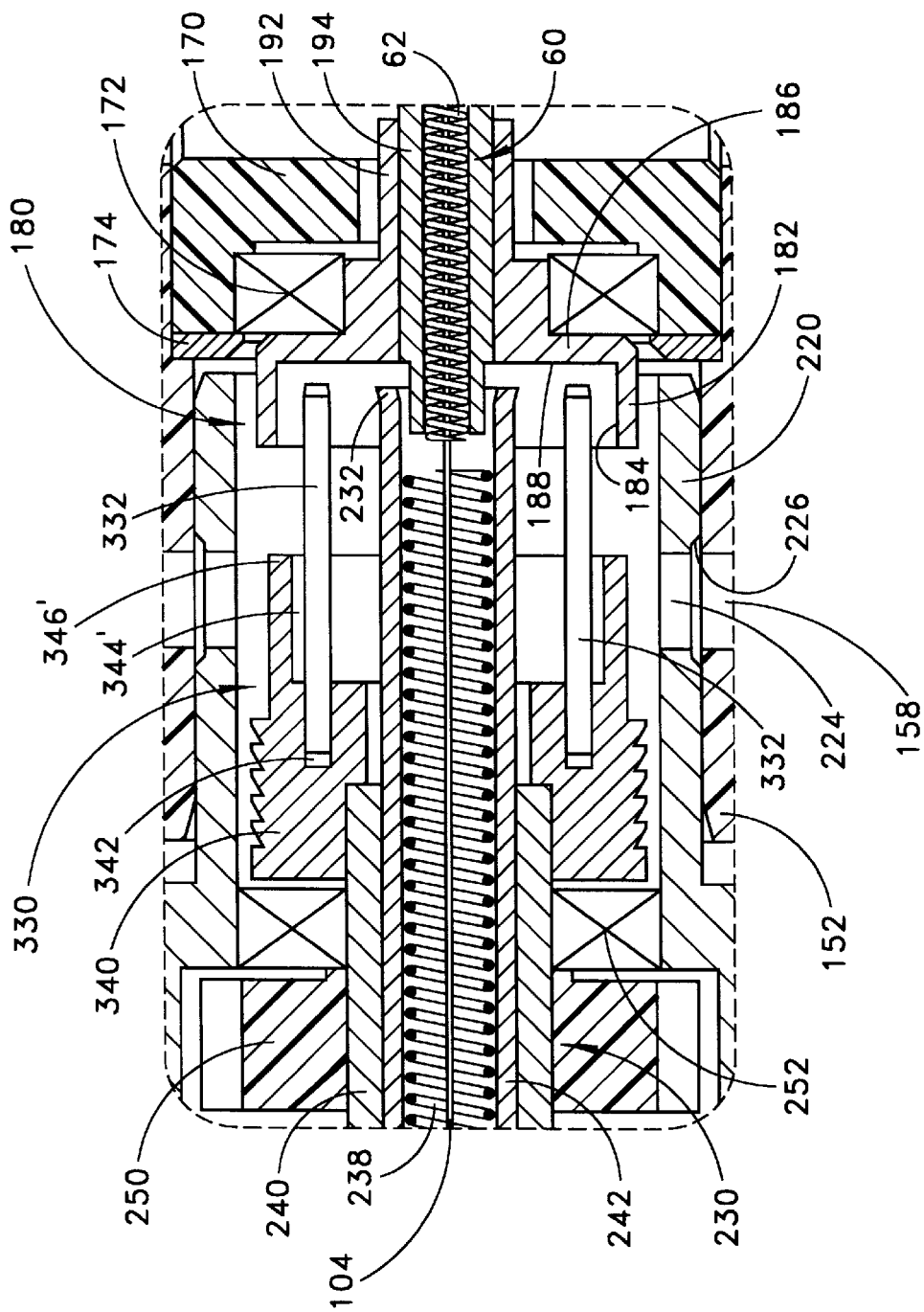
FIG. 40 is a view similar to FIG. 36, but illustrating an alternative embodiment of a base of the prime mover coupling.
Figure 41:
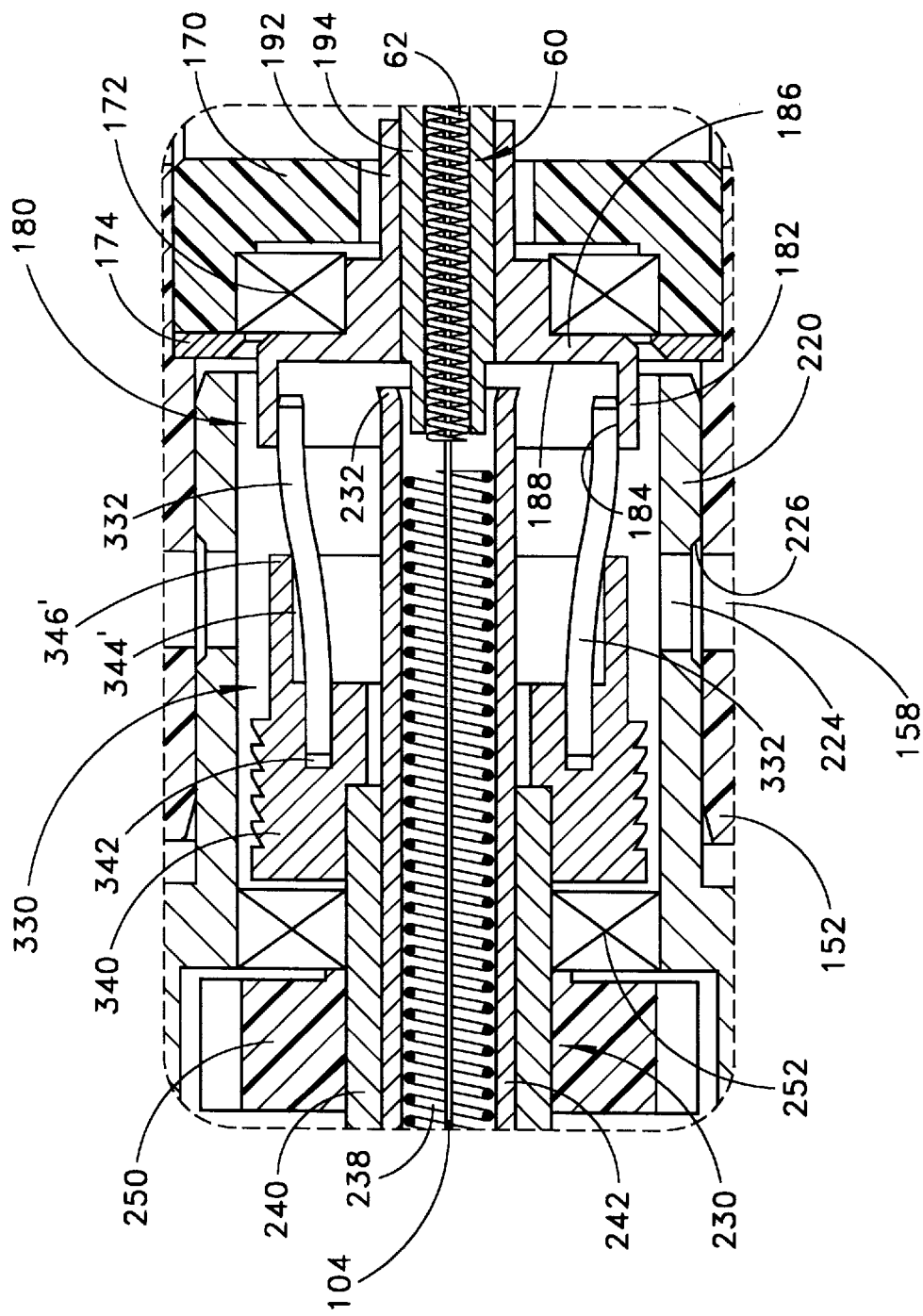
FIG. 41 illustrates how the flexible pins of the prime mover coupling of FIG. 40 deflect into frictional engagement with the interior surface of the drive shaft socket upon rapid rotation of the prime mover.

FIGS. 40 and 41 illustrate an alternative embodiment of the coupling base 340 shown in FIGS. 36–39. In FIGS. 36–39, each pin is received in a separate counterbore 344. In this embodiment, the wall 346 of each counterbore 344 serves as a separate abutment which limits outward deflection of an intermediate point along the length of the pin received therein. In FIGS. 40 and 41, however, these individual counterbores are all replaced with a single annular recess 344' having a single annular wall 346', which extends longitudinally distally from the coupling base 340 and is spaced radially outwardly from each of the flexible pins 332 when the coupling base is not rotated.

Figure 42:
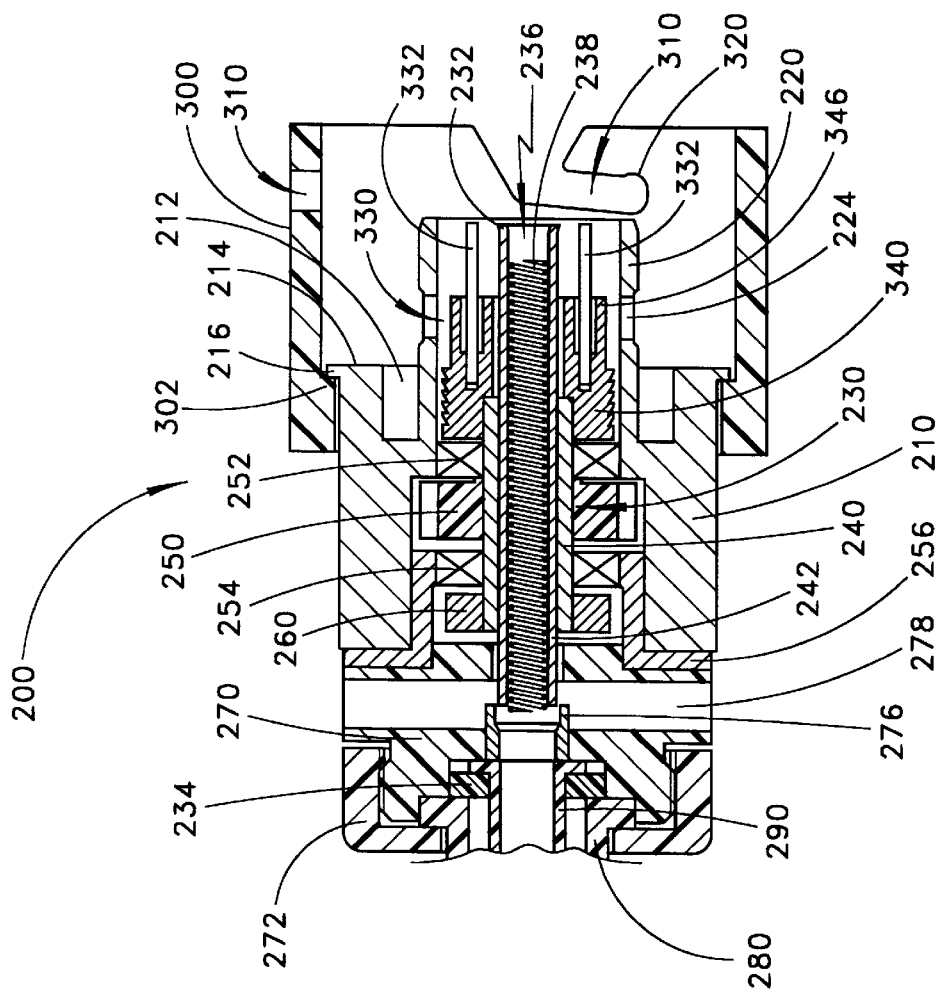
FIG. 42 is an isolational view of the prime mover carriage shown in FIG. 26.
Figure 43:
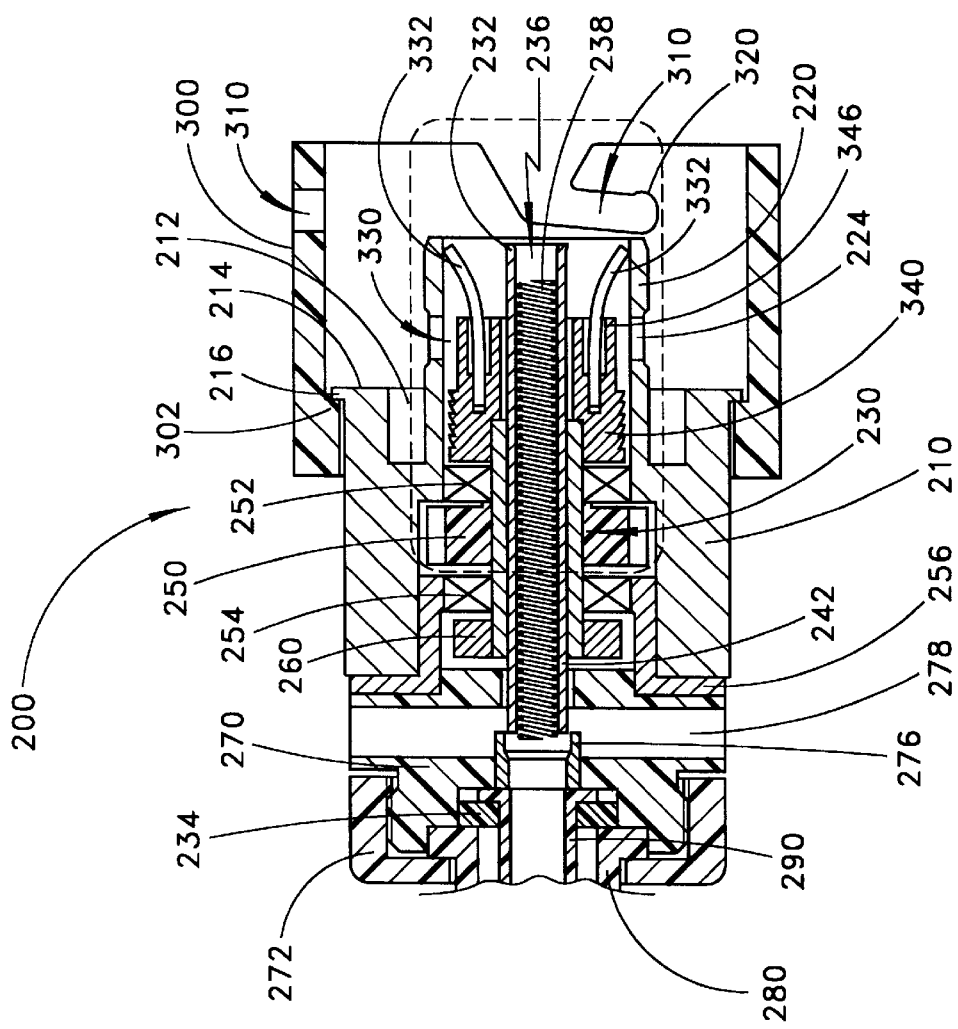
FIG. 43 is a longitudinal cross sectional view similar to FIG. 42, but illustrating how the flexible pins of the prime mover coupling can rub against an interior surface of the prime mover carriage upon rapid rotation of the prime mover when the prime mover carriage is not interconnected with the drive shaft carriage.
Figure 44:
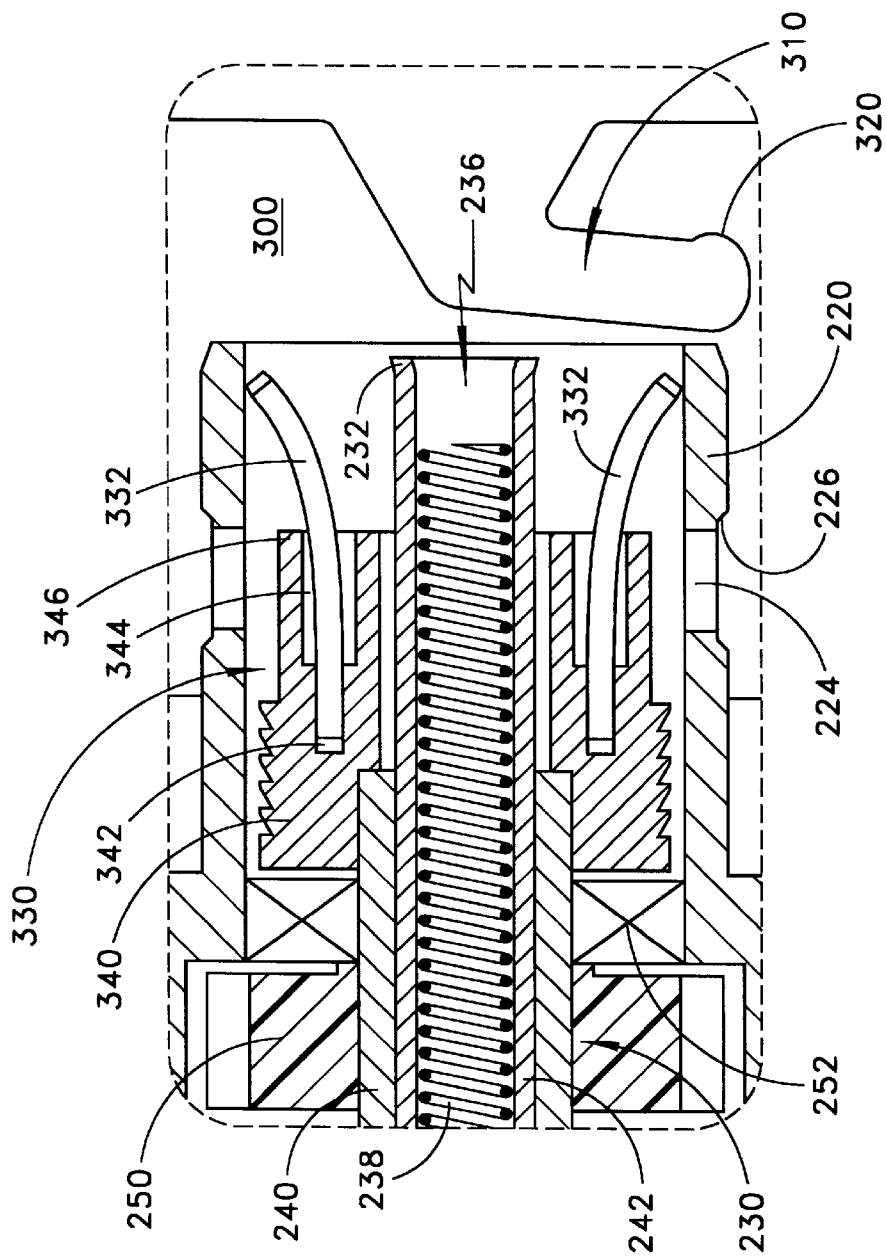
FIG. 44 is an enlarged view of the section outlined in FIG. 43.
Figure 45:
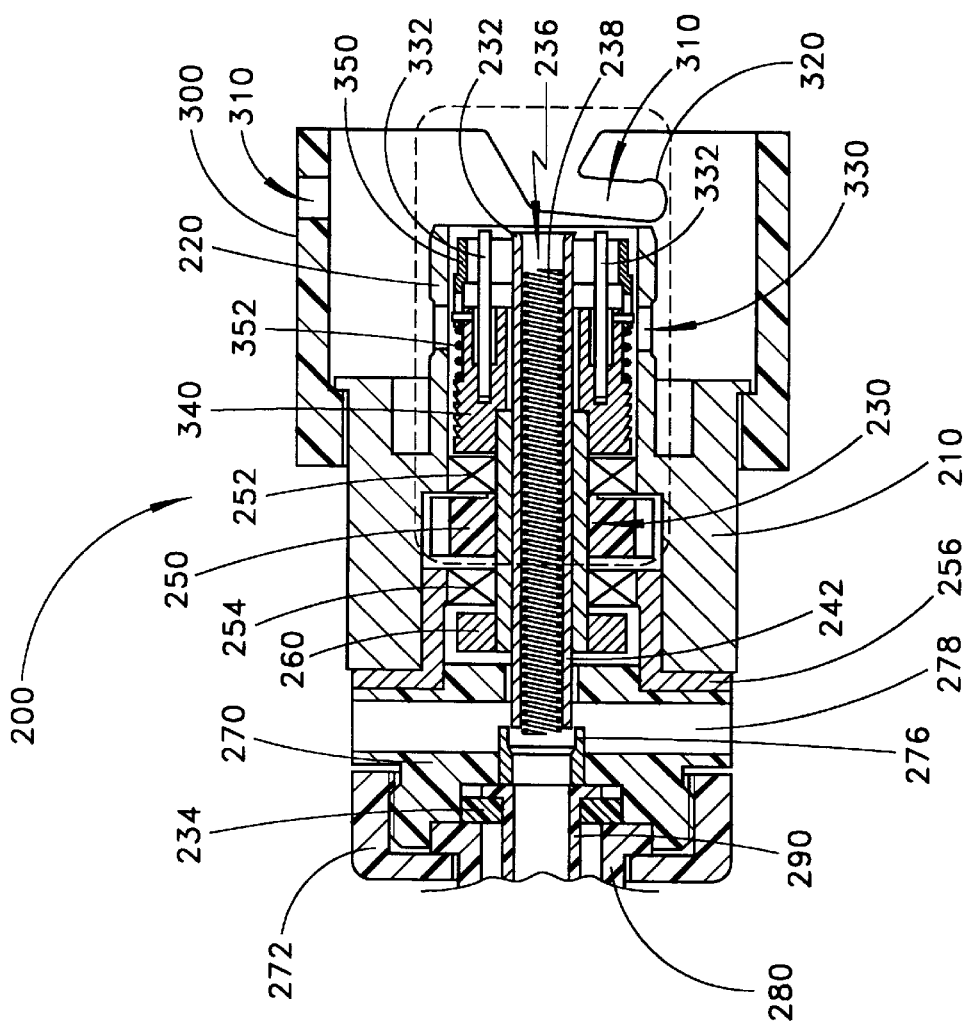
FIG. 45 is a longitudinal cross sectional view of a modified embodiment of a prime mover carriage which shows the carriage including a coupling shield carried by the prime mover coupling.
Figure 46:
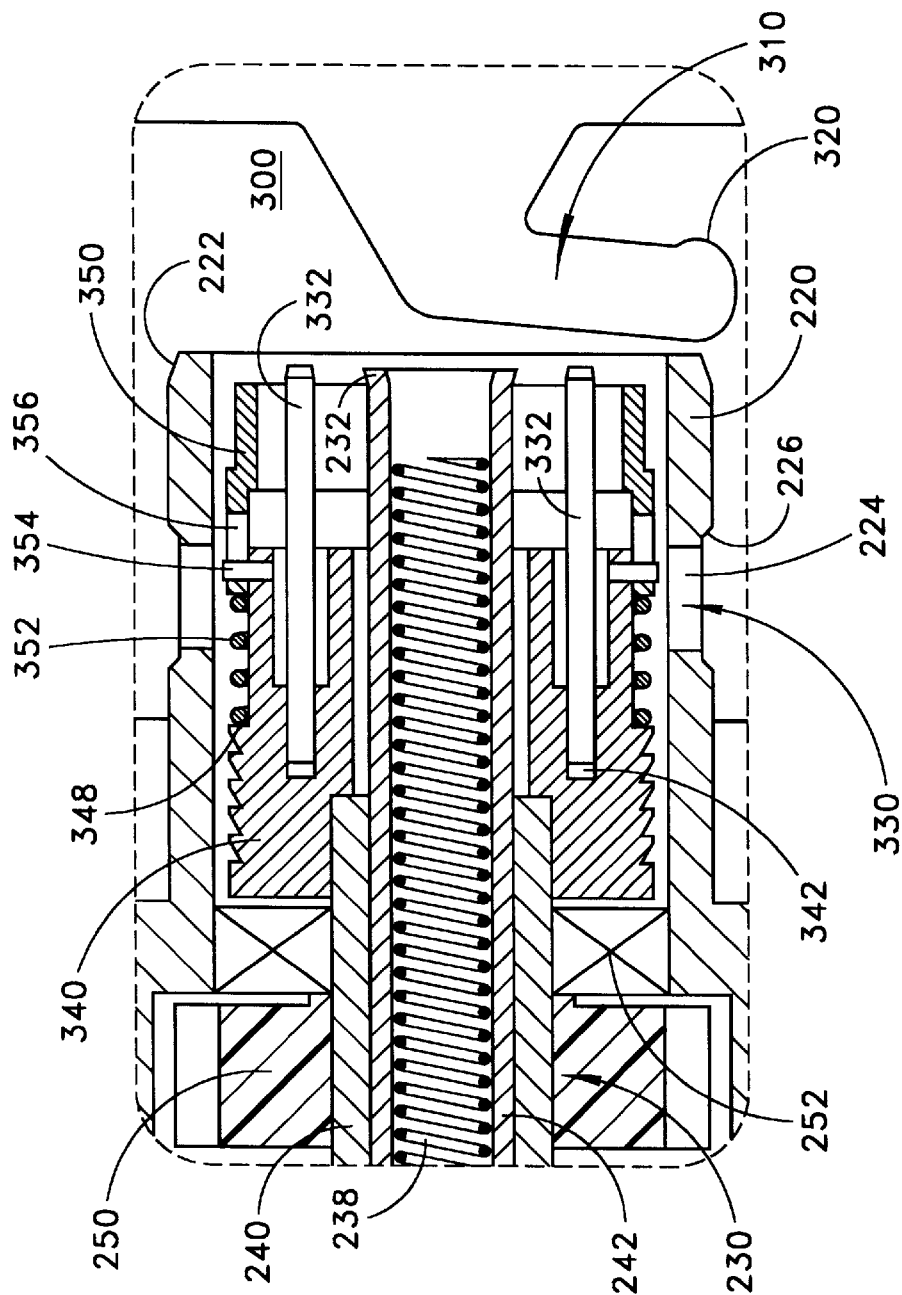
FIG. 46 is an enlarged view of the section outlined in FIG. 45.

FIG. 42 is an isolational view of the prime mover carriage 200 shown in FIG. 26. FIGS. 43 and 44 illustrate how the flexible pins 332 of the prime mover coupling 330 can rub against an interior surface of the guiding sleeve 220 of the prime mover carriage 200 upon rapid rotation of the prime mover when the prime mover carriage 200 is not interconnected with the drive shaft carriage 150. Potentially, this could damage either the pins 332 or the guiding sleeve 220.

FIGS. 45–50 illustrate a preferred embodiment wherein the prime mover carriage 200 further comprises a coupling shield which restricts radial expansion of the prime mover coupling upon rapid rotation of the prime mover when the prime mover coupling 330 is not properly received within the drive shaft socket 180. This coupling shield comprises an annular collar 350 which can surround a length of the flexible pins 332.

The annular collar 350 is carried by the coupling base 340 of the prime mover coupling and should be free to slide longitudinally along the coupling base. The coupling shield is desirably biased distally into a protective position around the flexible pins 332, such as by means of a compression spring 352 carried by the coupling base 340 between a rim 348 of the coupling base and a proximal face of the annular collar 350. The coupling base 340 and the annular collar 350 shown in the drawings are fitted together in a tongue-in-groove relationship to guide the collar 350 generally longitudinally along the coupling base 340 and limit rotation of the collar 350 with respect to the base 340. In the illustrated embodiment, the coupling base 340 includes a pair of short alignment pegs 354 which extend radially outwardly from the coupling base and are slidably received in longitudinal slots 356 in the annular collar 350. It should be noted, however, that there should be no deleterious consequences if the annular collar 350 is permitted to rotate with respect to the coupling base 340. Furthermore, permitting the collar 350 to rotate with respect to the coupling base 340 may reduce the cost of the prime mover coupling and simplify its assembly.

Figure 47:
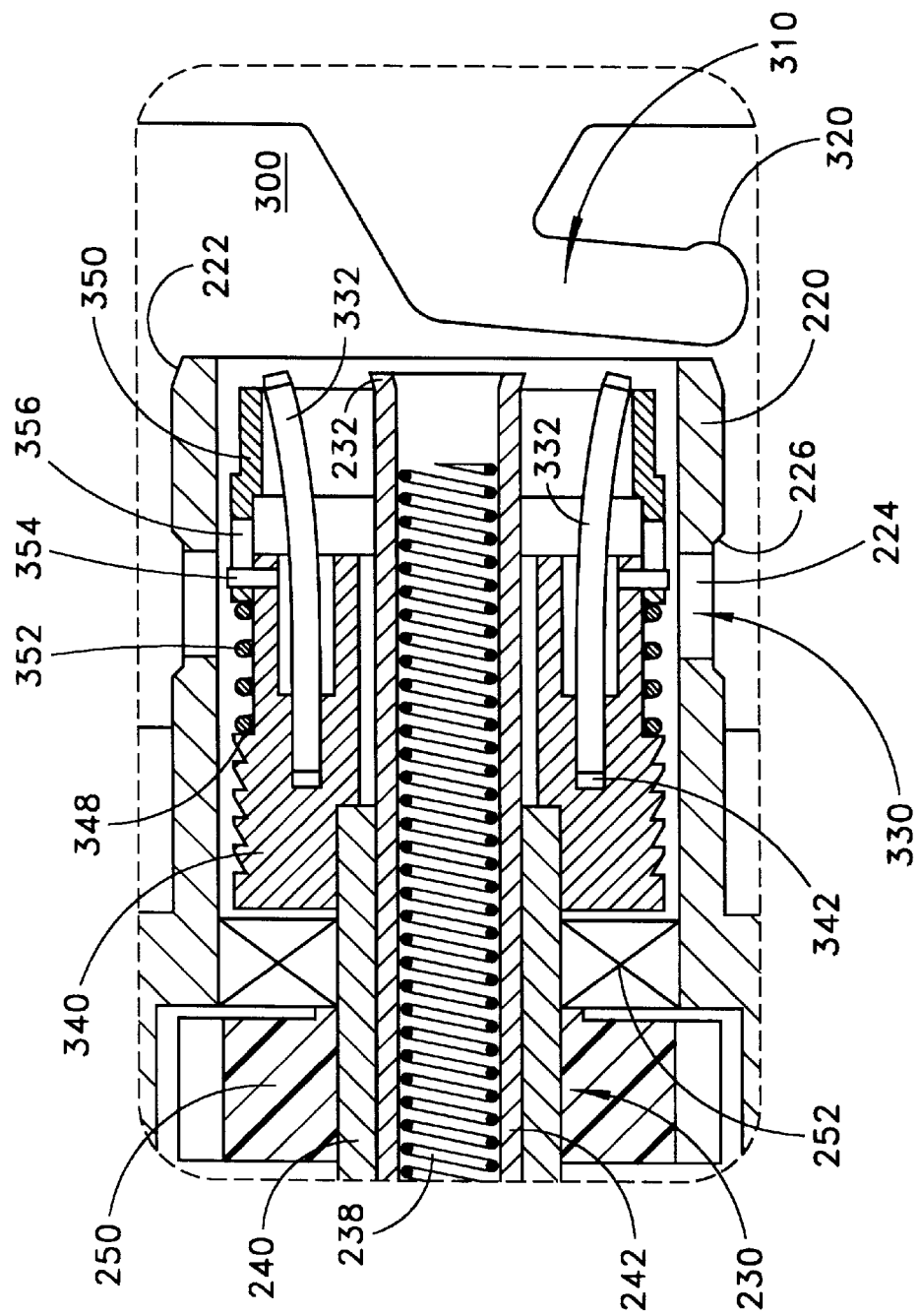
FIG. 47 is a longitudinal cross sectional view similar to FIG. 46, but illustrating how the coupling shield restricts outward deflection of the distal ends of the flexible pins of the prime mover coupling upon rapid rotation of the prime mover when the prime mover carriage is not interconnected with the drive shaft carriage.

The coupling shield will restrict outward deflection of the free distal ends of the flexible pins 332 even if an operator accidentally activates the prime mover when the prime mover coupling 330 is not properly received within the drive shaft socket 180. Upon rapid rotation of the prime mover, the deflecting pins 332 will abut the annular collar 350, as shown in FIG. 47, instead of rubbing against the interior of the guiding sleeve 320. Since the annular collar 350 is rotated together with the coupling base 340 and the pins 332, it will not be damaged by the pins.

Figure 48:
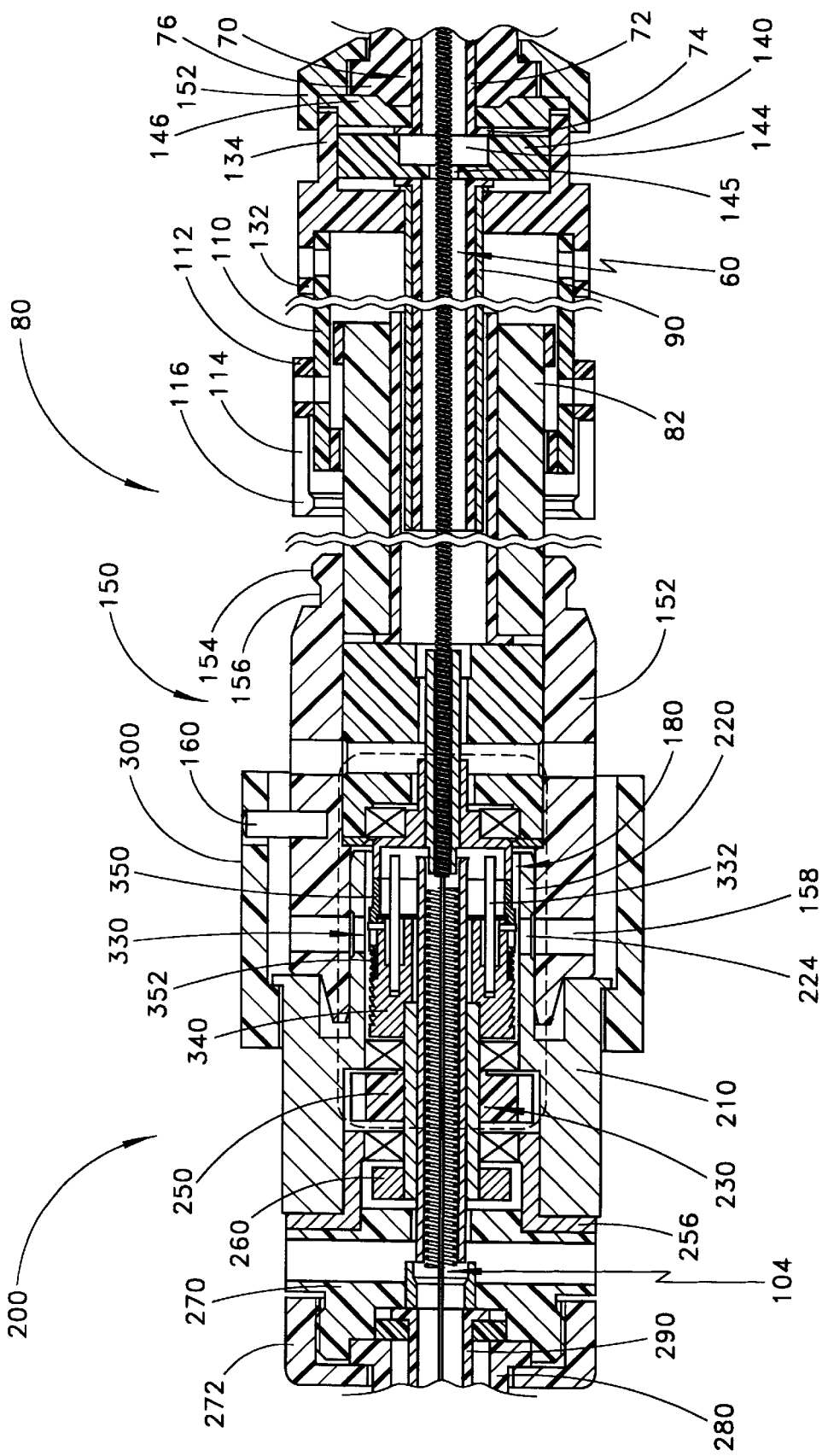
FIG. 48 is a longitudinal cross sectional view showing the modified prime mover carriage of FIG. 45 interconnected with a drive shaft carriage and illustrating how the coupling shield can be moved away from the distal ends of the pins to permit the pins to be received in the drive shaft socket.
Figure 49:
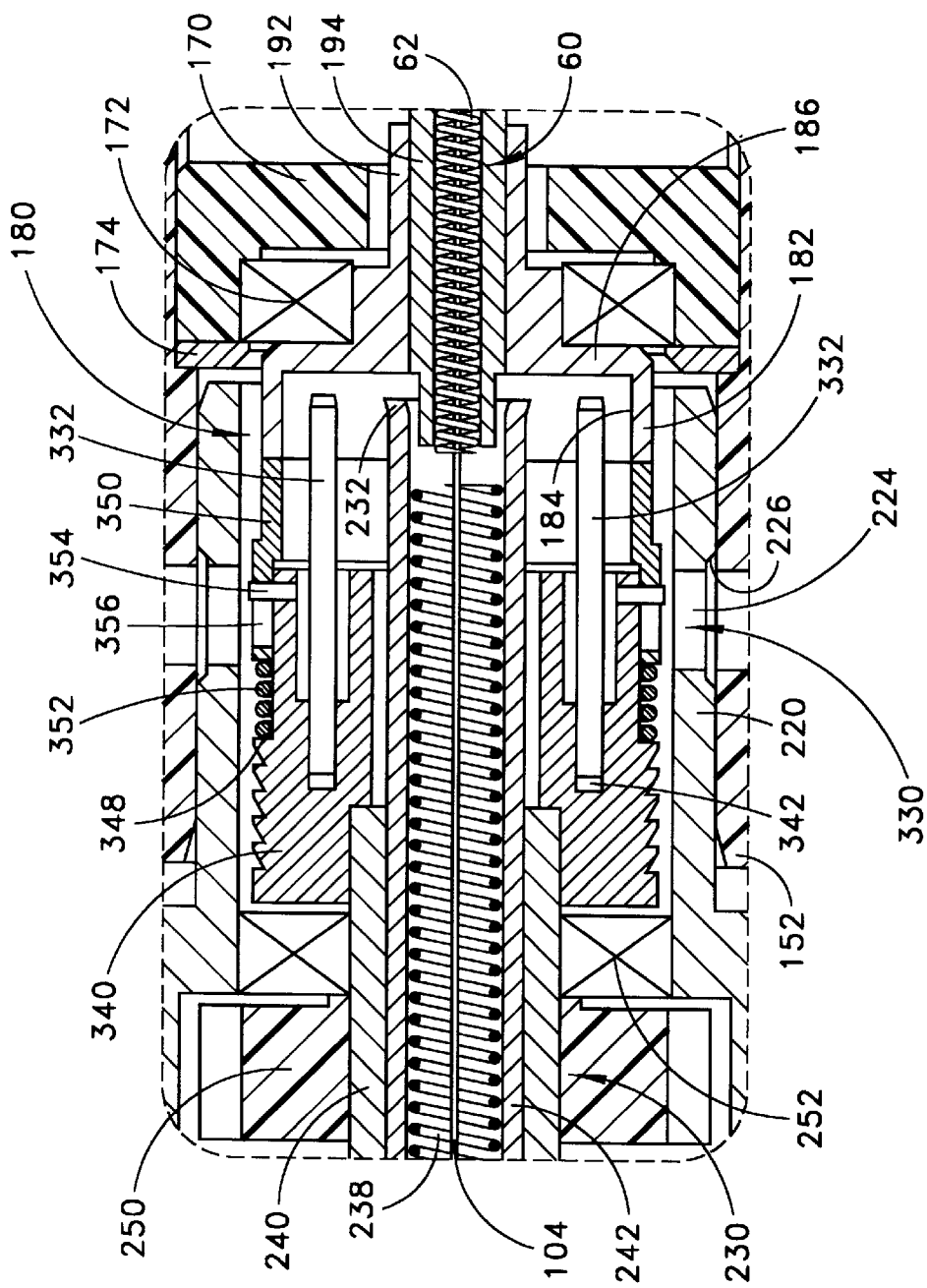
FIG. 49 is an enlarged view of the section outlined in FIG. 48.
Figure 50:
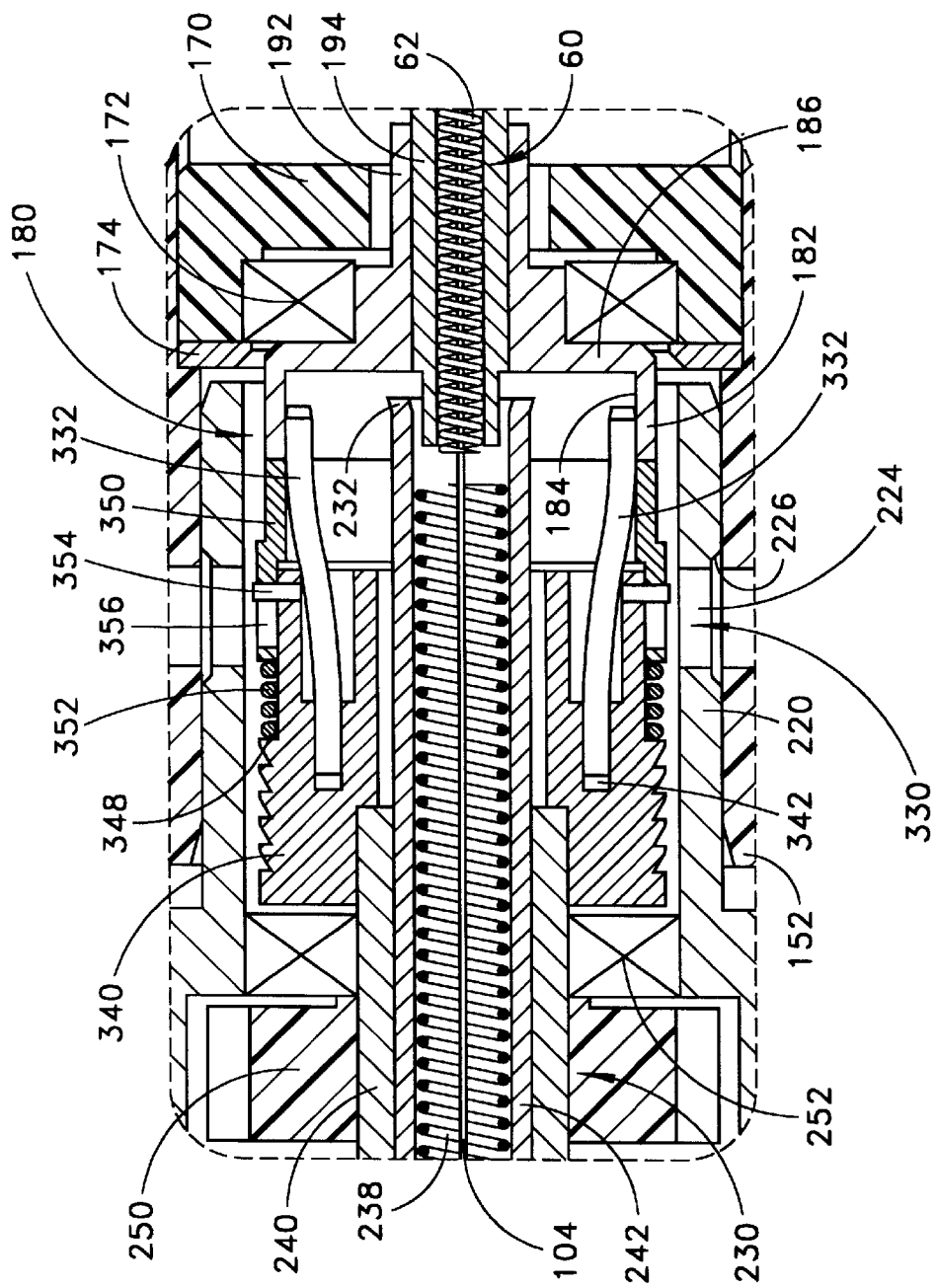
FIG. 50 is a longitudinal cross sectional view similar to FIG. 49, but illustrating how the flexible pins of the prime mover coupling engage the drive shaft socket upon rapid rotation of the prime mover.

FIGS. 48–50 illustrate how the distal end portions of the flexible pins 332 can be properly received within the drive shaft socket 180 when the drive shaft carriage 150 and the prime mover carriage 200 are connected to one another. The annular collar 350 presents a generally annular distal face which is sized to abut the drive shaft socket 180. When the prime mover coupling 330 is moved toward the drive shaft socket 180, the drive shaft socket 180 will move the annular collar 350 proximally away from the distal ends of the flexible pins 332 to permit the distal end portions of the pins 332 to be properly received within the socket 180. When the prime mover is rotated, the flexible pins 332 can deflect radially outwardly into frictional engagement with the interior surface of the drive shaft socket 180, as shown in FIG. 50.

Figure 51:
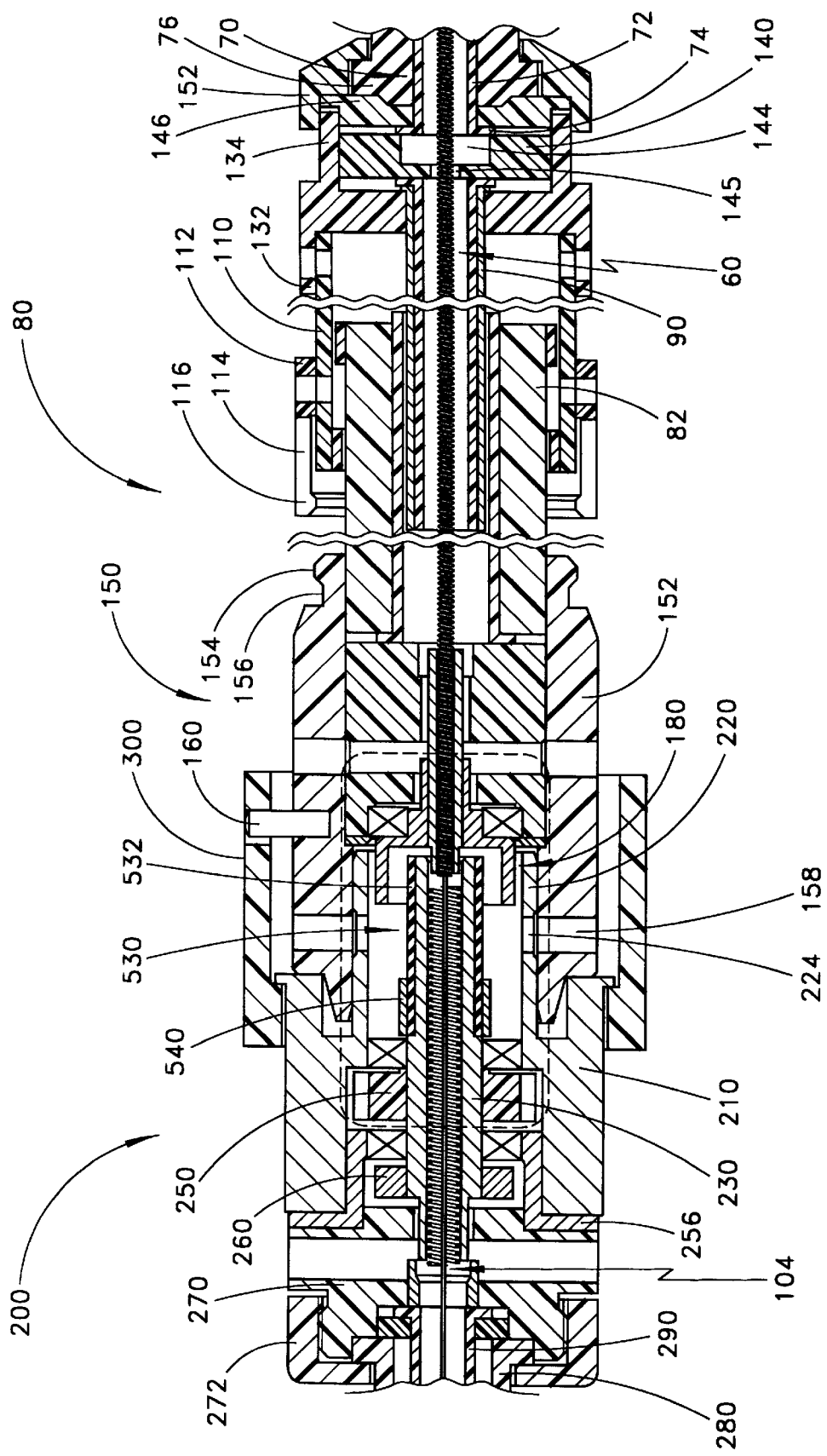
FIG. 51 is a longitudinal cross sectional view similar to FIG. 34, but illustrating a radially expandable prime mover coupling which employs an elastomeric, radially expandable tube.
Figure 52:
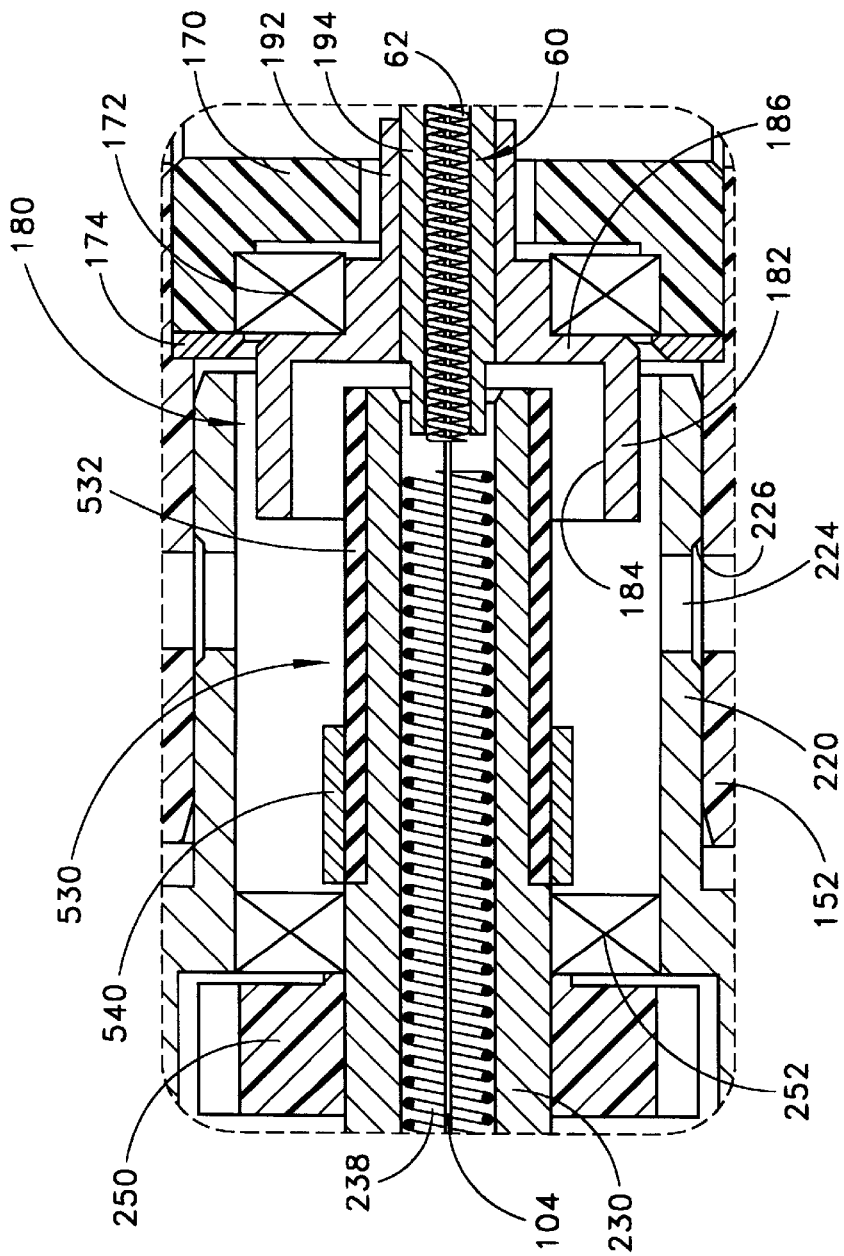
FIG. 52 is an enlarged view of the section outlined in FIG. 51.
Figure 53:
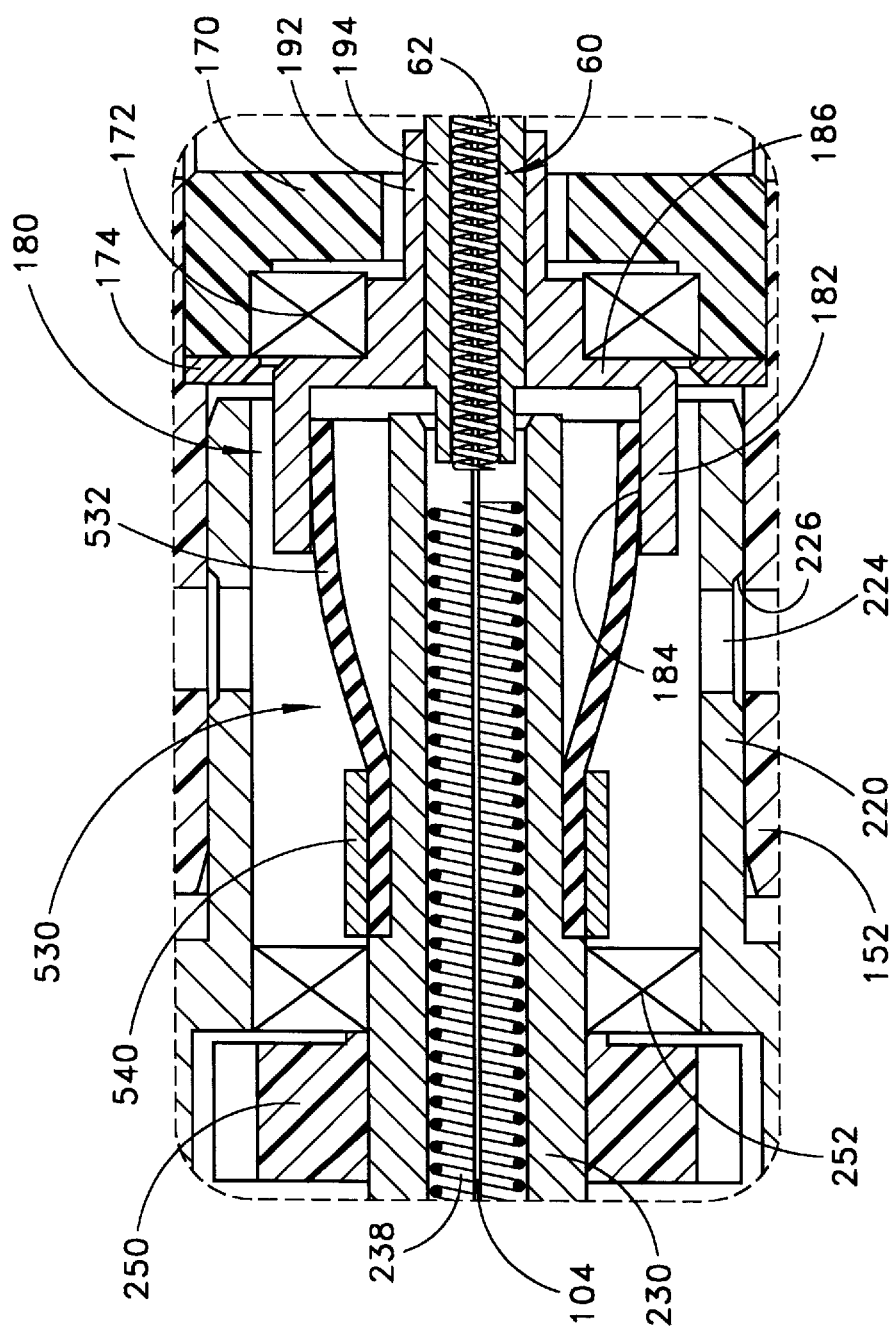
FIG. 53 is a longitudinal cross sectional view similar to FIG. 52, but illustrating how the free end of the radially expandable tube of the prime mover coupling engages the drive shaft socket upon rapid rotation of the prime mover.

FIGS. 51–53 illustrate an alternative embodiment of a prime mover coupling 530 in accordance with the present invention. Elements in FIGS. 51–53 bear the same reference numbers as the numbers used for like elements of the embodiment shown in FIGS. 34, 36 and 39, for example. In this alternative embodiment, the prime mover coupling comprises an elastomeric, radially expandable tube 532. The distal end portion of the expandable tube 532 is connected to the prime mover shaft 230 and the proximal end of the tube 532 is free to expand radially outwardly to engage the interior engagement surface 184 of the drive shaft socket 180 when the prime mover is rotated. In FIGS. 51–53, the expandable tube 532 is held in place about the prime mover shaft 230 by a fixation ring 540, but the tube 532 can instead be glued or vulcanized to the shaft 230. The tube can be formed of any suitable elastomeric material; rubber and silicone compounds are believed to be suitable. It is also worth noting that the prime mover shaft 230 shown in these drawings is integrally formed as a single component rather than being formed of inner and outer tubular portions as illustrated in the previous drawings.

Figure 54:
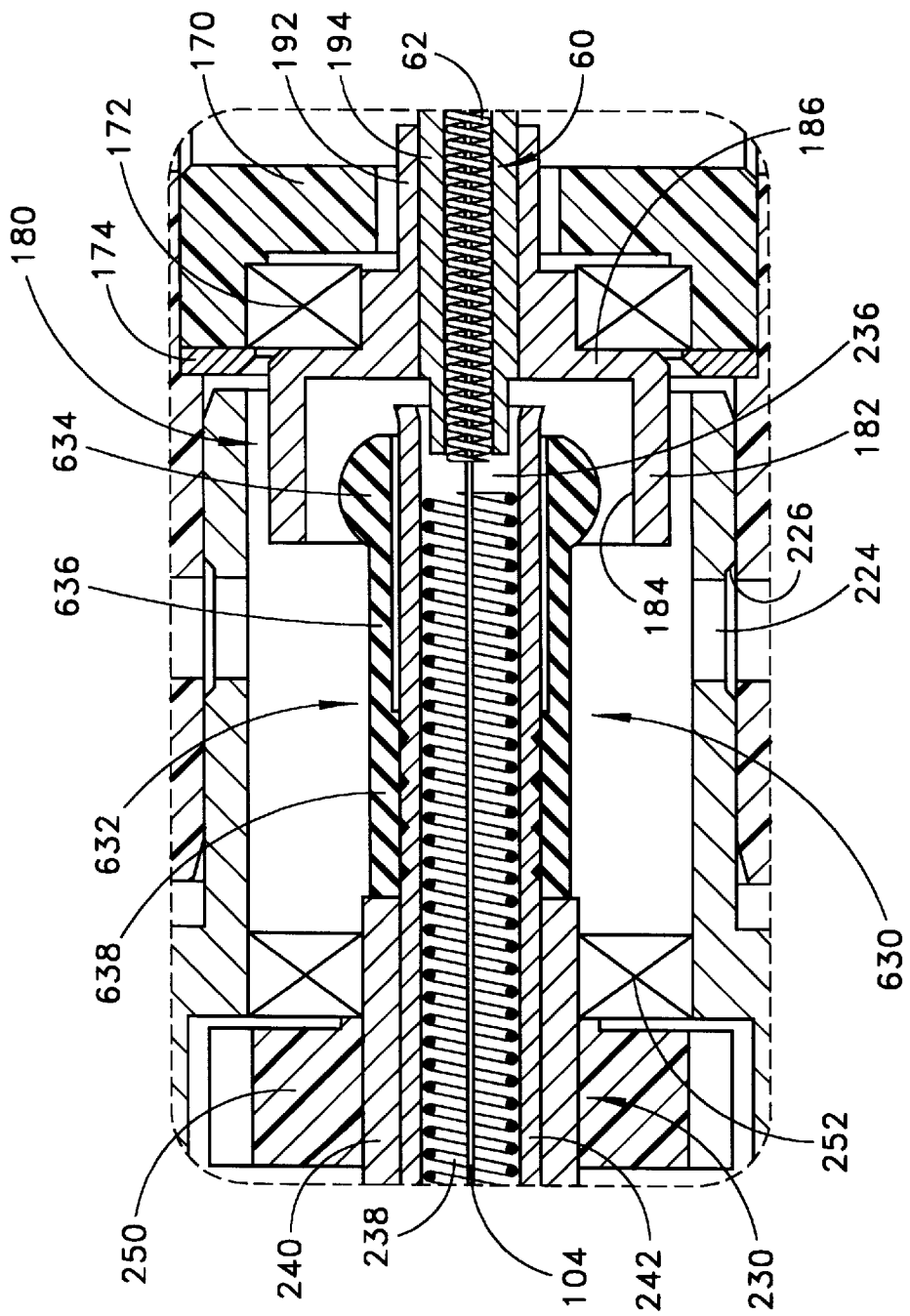
FIG. 54 is a longitudinal cross sectional view similar to FIG. 52, but illustrating a modified embodiment of the radially expandable tube.
Figure 55:
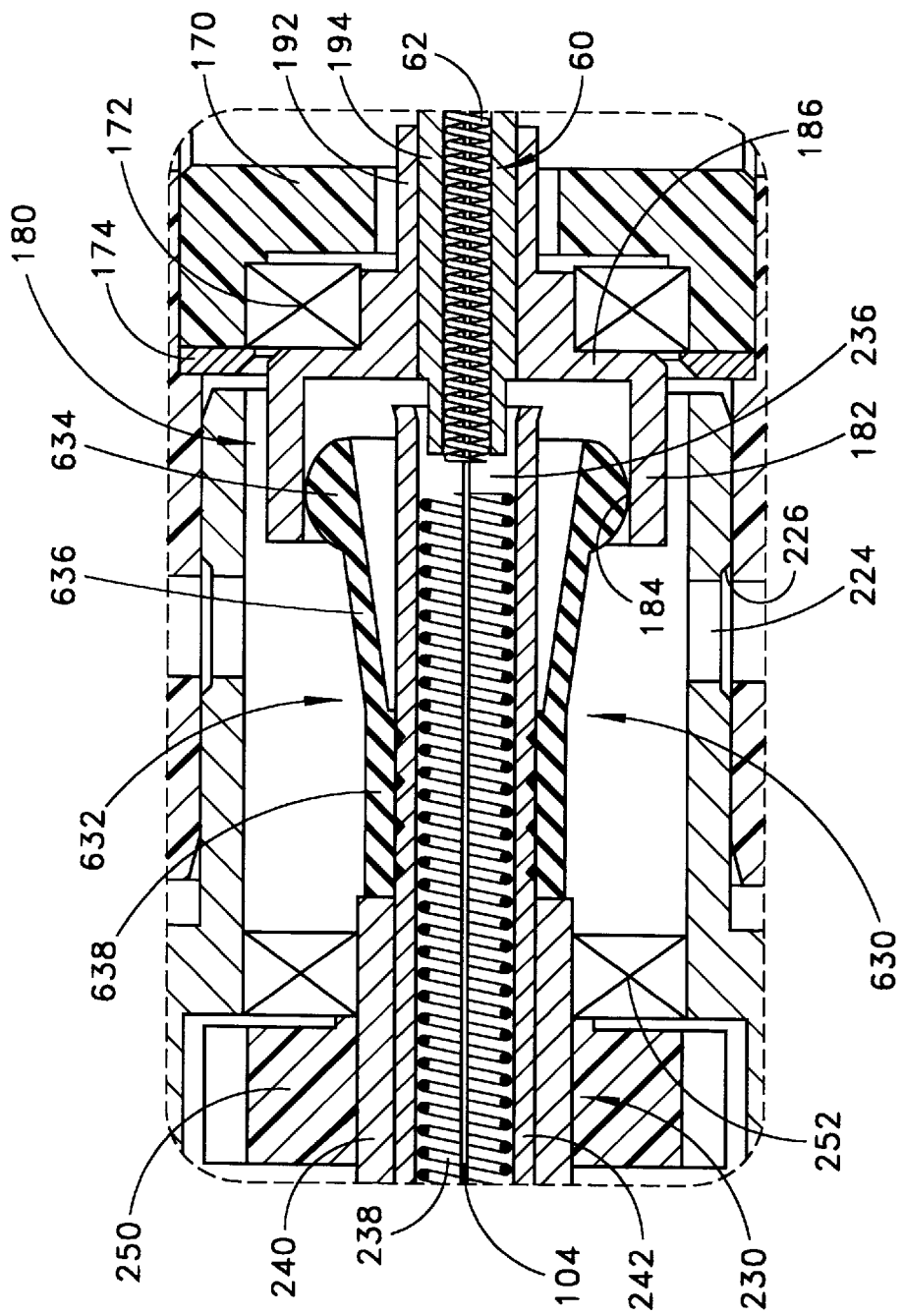
FIG. 55 is a longitudinal cross sectional view similar to FIG. 54, but illustrating how the free end of the radially expandable tube of the prime mover coupling engages the drive shaft socket upon rapid rotation of the prime mover.

FIGS. 54 and 55 illustrate a modification of the embodiment of FIGS. 51–53. In this embodiment, the prime mover coupling 630 includes a different radially expandable tube 632. The radially expandable tube 532 in FIGS. 51–53 is substantially uniform along its length, but the distal portion 634 of the tube 632 in FIGS. 54 and 55 is thicker than its intermediate portion 636. The intermediate portion 636 of the tube 632 extends between the thicker distal portion 634 and the proximal portion 638, which is attached to the inner tubular portion 242 of the prime mover shaft. Both the distal 634 and intermediate 636 portions of the expandable tube 632 are free to expand radially outwardly. If the material forming the expandable tube 632 is uniform along the length of the tube, the distal portion 634 will have a greater mass per unit length than the intermediate portion 636. The same objective can be achieved by varying the density of the material of the tube along its length without changing the dimensions of the tube.

In FIGS. 54 and 55, the proximal portion 638 of the expandable tube 632 is attached to the inner tubular portion 242 of the prime mover shaft by an adhesive. The proximal portion 638 of the tube 632 may have a smaller inner diameter than the rest of the tube 632 so there is some clearance between the inner tubular portion 242 of the prime mover shaft and the intermediate 636 and distal 634 portions of the tube.

Figure 56:
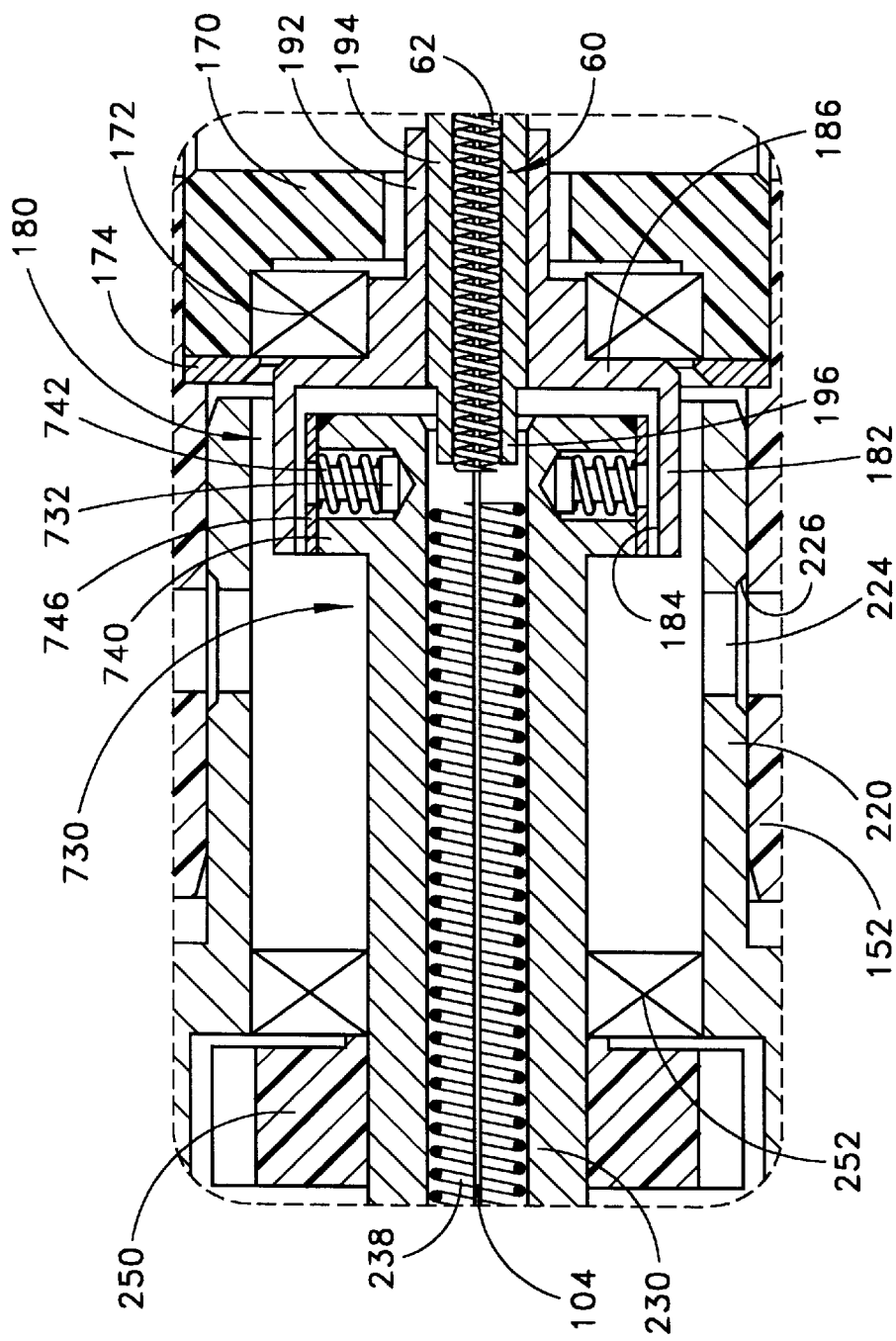
FIG. 56 is a longitudinal cross sectional view similar to FIG. 54, but illustrating a radially expandable prime mover coupling which employs flyweights instead of an elastomeric, radially expandable tube.
Figure 57:
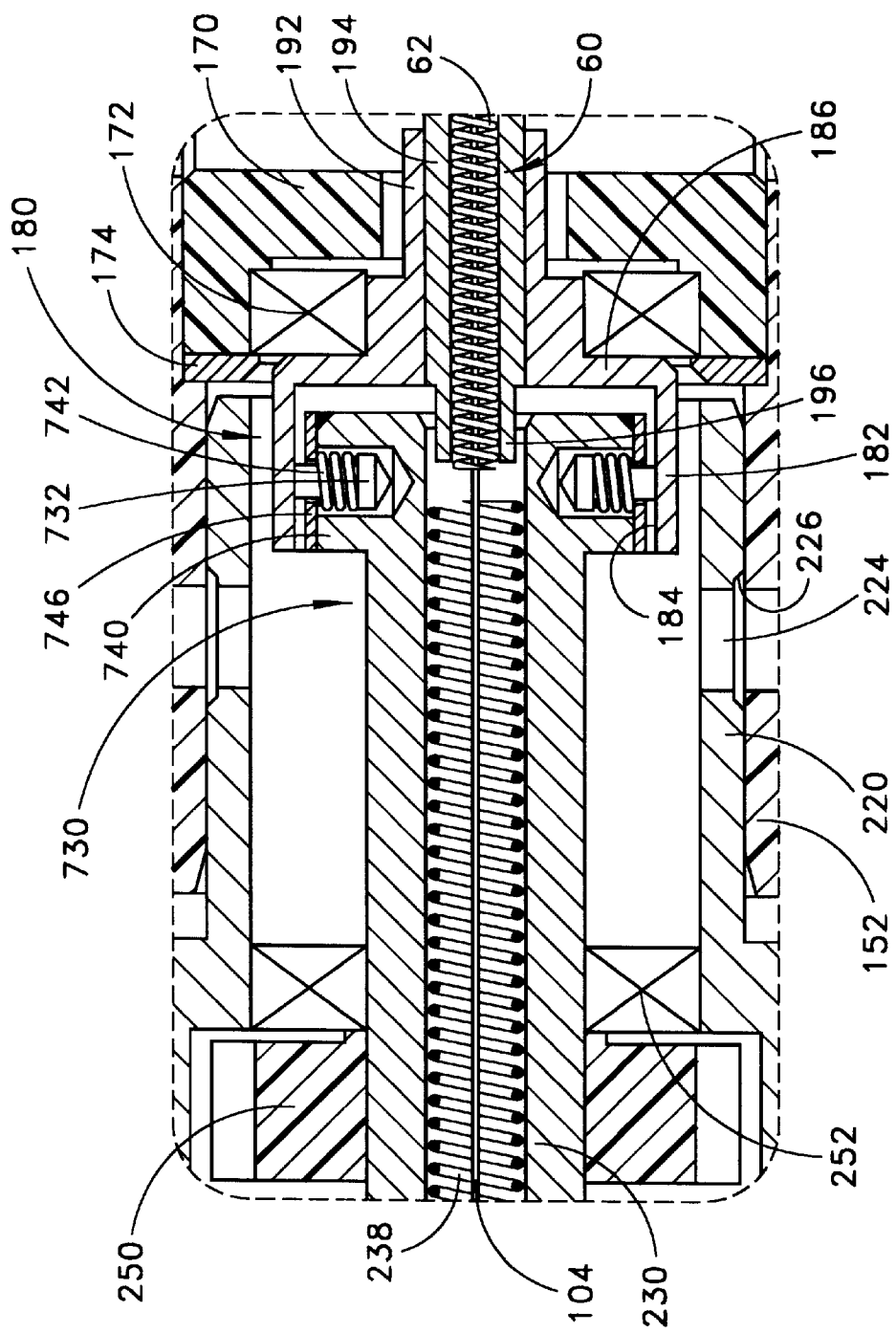
FIG. 57 is a longitudinal cross sectional view similar to FIG. 56, but illustrating how the flyweights of the prime mover coupling engage the drive shaft socket upon rapid rotation of the prime mover.

FIGS. 56 and 57 show yet another alternative embodiment of a prime mover coupling in accordance with the invention. This prime mover coupling 730 includes a coupling base 740 and at least two flyweights 732 carried by the coupling base. Each flyweight 732 should be free to move radially outwardly to engage the interior engagement surface 184 of the engagement ring 182 of the drive shaft socket 180 when the prime mover is rotated. In the illustrated embodiment, each flyweight is slidably received in a radially extending bore in the coupling base. The coupling base 740 also includes a circumferential stop 746 for limiting outward movement of the flyweights. This stop 746 has holes aligned with the bores in the coupling base 740 to permit an outer portion of the flyweights 732 to pass therethrough. The flyweights 732 may be biased inwardly with respect to the circumferential stop 746 by compression springs 742 or the like. In the embodiment shown in FIGS. 56 and 57, the coupling base 740 of the prime mover coupling and the prime mover shaft 230 are integrally formed as a single component.

Figure 58:
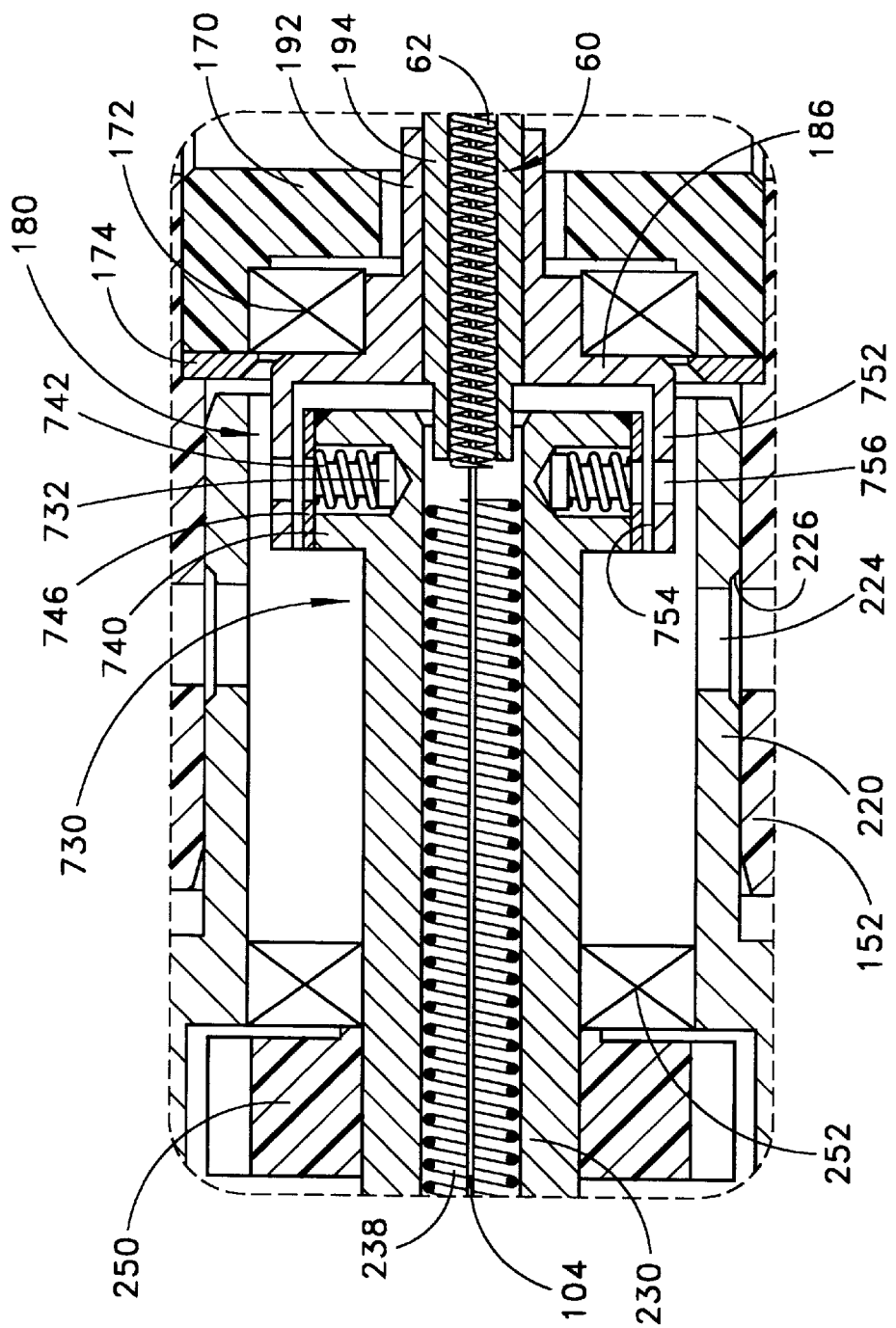
FIG. 58 is a longitudinal cross sectional view similar to FIG. 56, but illustrating a modified embodiment of the drive shaft socket which includes recesses for engaging the flyweights.
Figure 59:
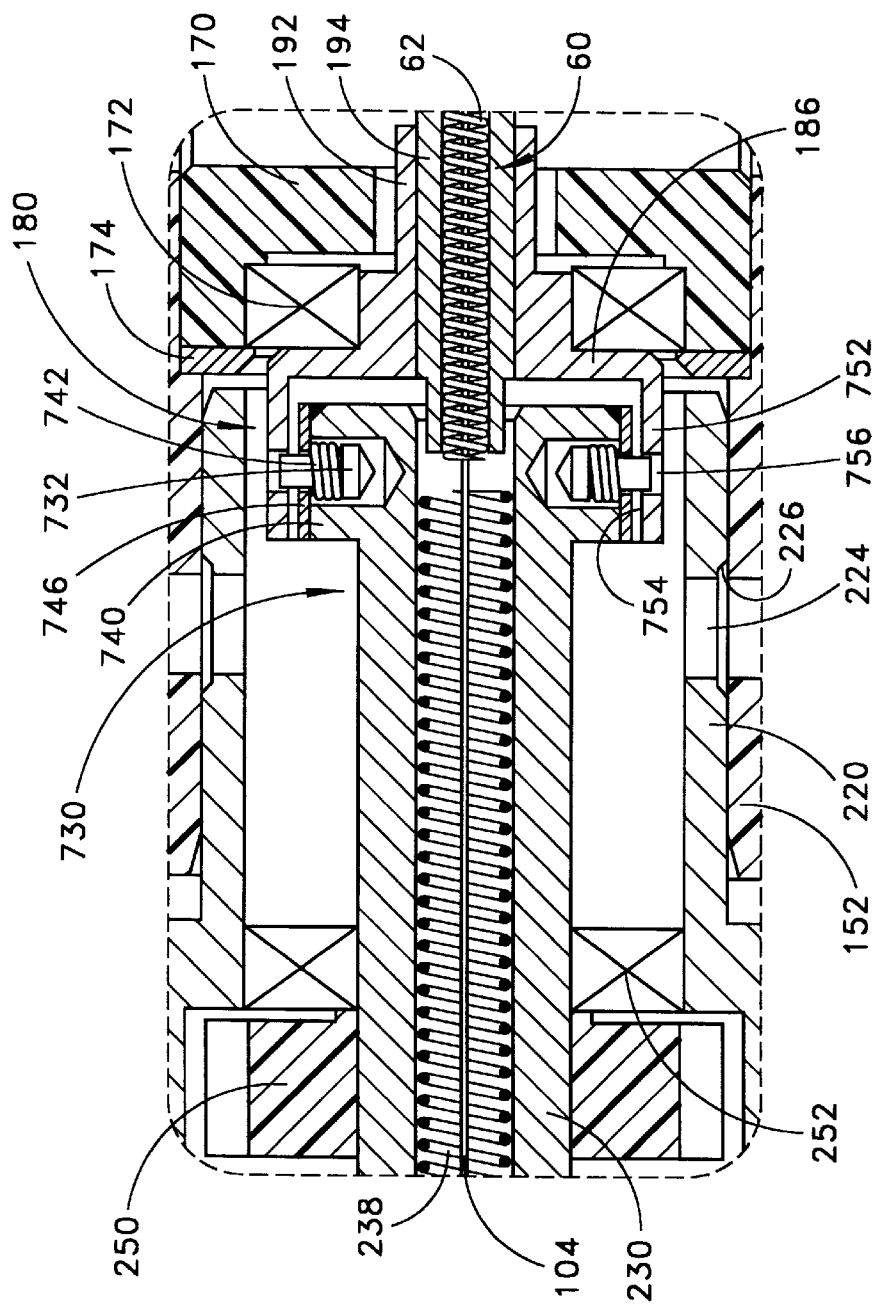
FIG. 59 is a longitudinal cross sectional view similar to FIG. 58, but illustrating how the flyweights of the prime mover coupling engage the recesses of the drive shaft socket upon rapid rotation of the prime mover.

FIGS. 58 and 59 show a modified version of a drive shaft socket which is useful in connection with a prime mover coupling 730 employing flyweights 732. In particular, the interior engagement surface 754 of the engagement ring 752 of the drive shaft socket 180 includes recesses 756 for engaging the flyweights 752. As illustrated, these recesses may simply extend radially through the engagement ring 752.

Figure 60:
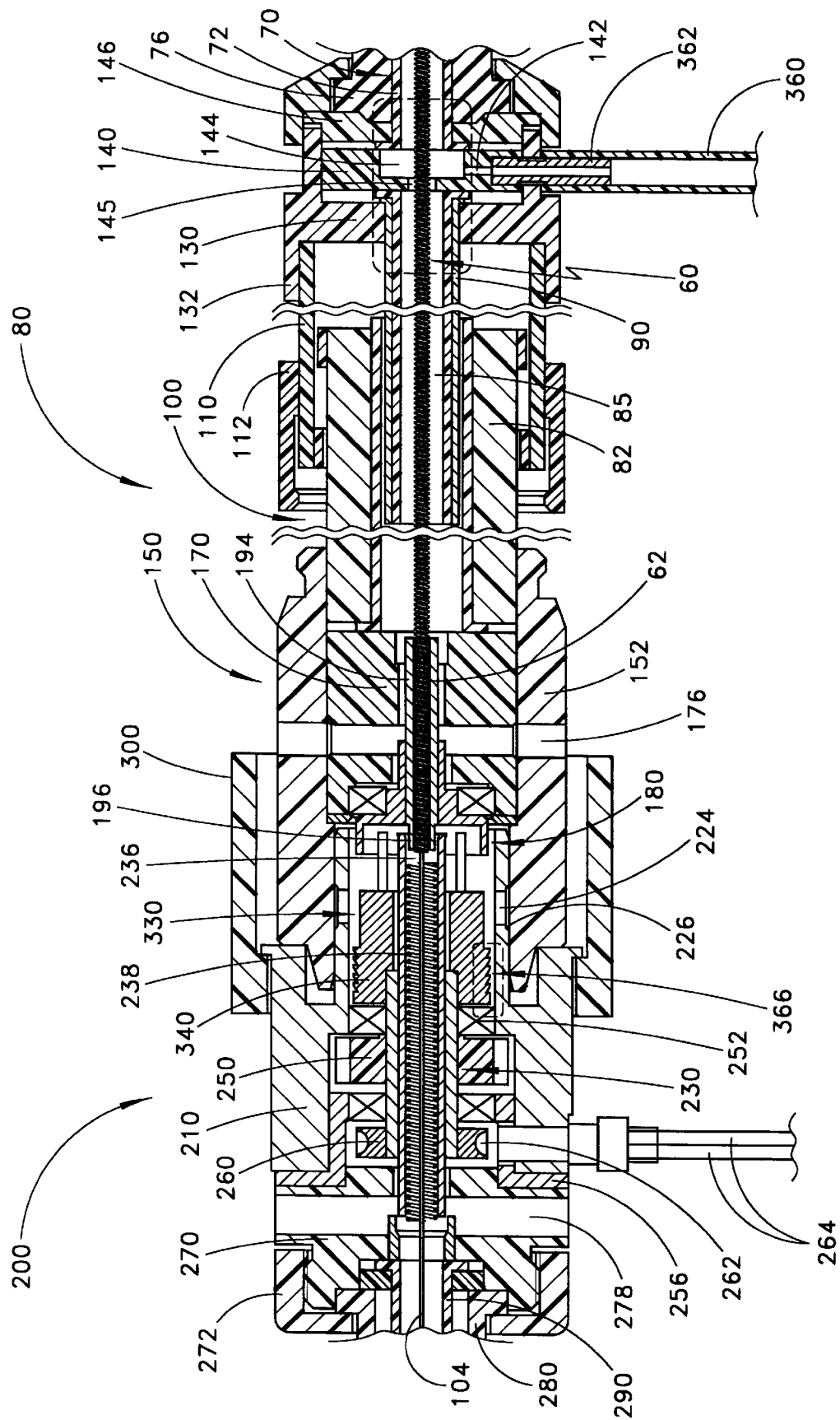
FIG. 60 is a longitudinal cross sectional view taken along line 60—60 of FIG. 34 and illustrating a flexible fluid supply tubing attached to the exchangeable drive shaft cartridge.

FIG. 60 is a longitudinal cross sectional view taken along line 60—60 of FIG. 34 and illustrating a flexible fluid supply tubing 360 attached to the exchangeable drive shaft cartridge 80. This flexible fluid supply tubing 360 is in fluid communication with the fluid-receiving recess 144 of the distal bulkhead 140. From the fluid-receiving recess 144, fluid may flow distally into the lumen of the catheter 70 and proximally into the lumen of the longitudinally extendable tube 100. As detailed above, the longitudinally extendable tube 100 is comprised of inner 90 and outer 82 telescoping tubes. The lumens of the outer 82 and inner 90 telescoping tubes and the lumen of the catheter 70 together define the drive shaft lumen 85 within which a majority of the length of the drive shaft is received.

Fluid supplied to the drive shaft lumen 85 will help reduce friction between the drive shaft 60 and the walls of the telescoping tubes 82, 90 and the catheter 70.

In the assembled device, the central extension 196 of the drive shaft socket 180 is received within the distal end of the guide wire lumen 236 of the prime mover shaft 230. This establishes fluid communication between the guide wire lumen of the drive shaft 60 and the guide wire lumen 236 of the prime mover shaft while minimizing leakage at this junction. The helically wound coil 238 disposed within the guide wire lumen 236 of the prime mover shaft rotates with the prime mover and is desirably oriented such that it will urge fluid proximally when the prime mover is rotated. The proximal end of the guide wire lumen 236 is in fluid communication with the short collar 276 and the proximal inner telescoping tube 290. A small gap is provided between the proximal end of the prime mover shaft 230 and the short collar 276 so some fluid may drain through the fluid outlet 278 in the proximal bulkhead 270.

One end of the flexible fluid supply tubing 360 communicates with an external fluid supply (not shown) while the other end of the tubing 360 is attached to the exchangeable drive shaft cartridge 80. Desirably, the fluid supply tubing 360 is attached to the exchangeable drive shaft cartridge 80 distally of at least one of the telescoping tubes 82, 90. Preferably, it is connected distally of both of the telescoping tubes 82, 90 and proximally of the catheter 70. In the illustrated embodiment, the fluid supply tubing 360 is attached to a metal tubing 362 carried by the distal bulkhead 140. The metal tubing 362 communicates with the fluid-receiving recess 144 in the bulkhead through the passageway 142. The distal bulkhead 140 is disposed between and operatively connects the inner telescoping tube 90 and the proximal end portion 72 of the catheter 70. Positioning the distal bulkhead 140 distally of the inner telescoping tube 90 assures that the fluid supply tubing 360 is attached to the exchangeable drive shaft cartridge 80 adjacent the distal end of the longitudinally extendable tube 100 and spaced distally from the drive shaft socket 180.

As noted above, the distal bulkhead 140 includes a narrow opening 145 which defines a reduced diameter segment of the drive shaft lumen 85. As better seen in the enlarged view of FIG. 61, the flexible drive shaft 60 passes through this narrow opening 145. Preferably, sufficient clearance exists between the drive shaft and the interior of the narrow opening 145 to permit a restricted flow of fluid proximally along the drive shaft lumen.

Figure 62:
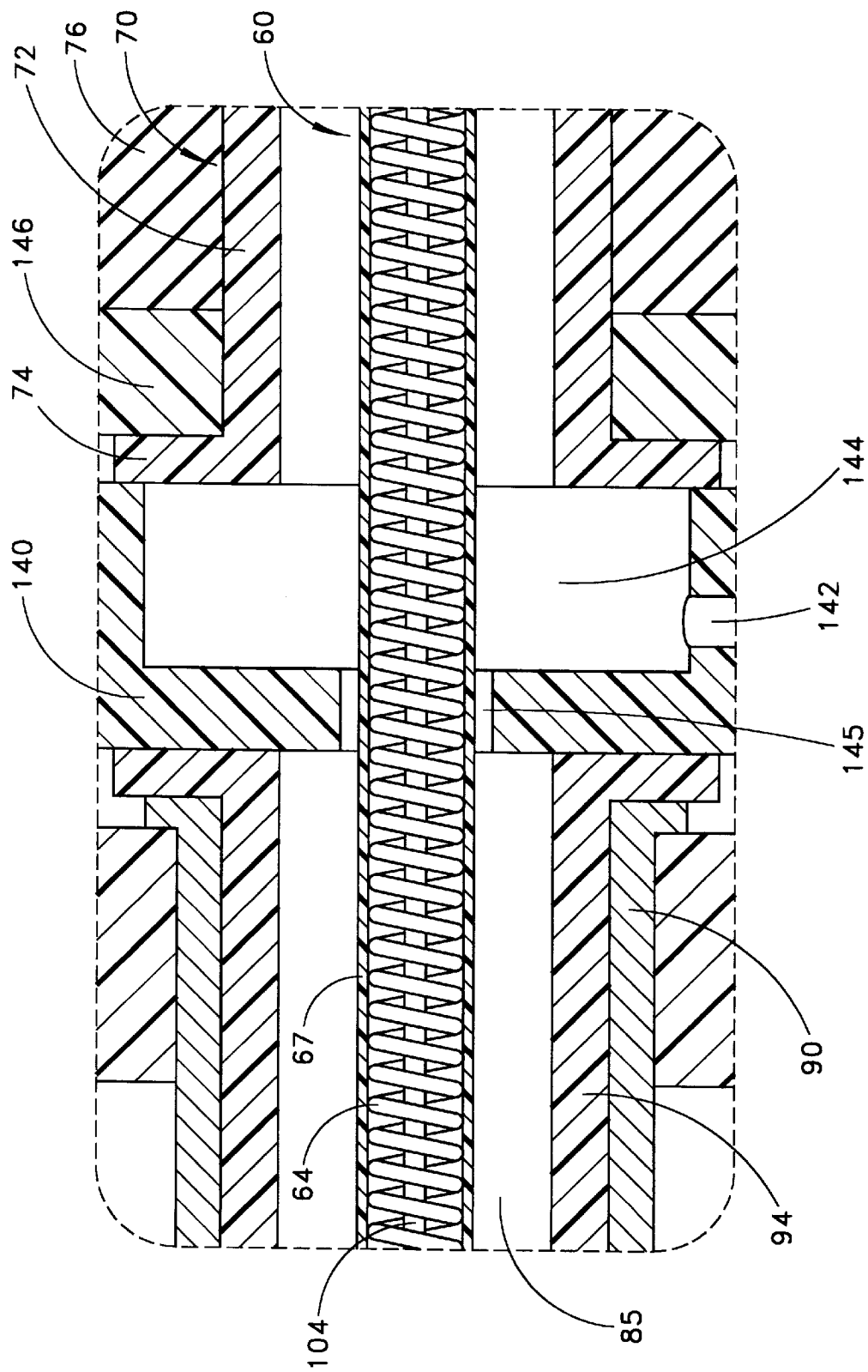
FIG. 62 is an enlarged view similar to FIG. 61, but illustrating a preferred embodiment wherein a heat shrinkable tubing has been shrunk onto a proximal length of an intermediate portion of the drive shaft.

FIG. 62 illustrates a preferred embodiment of a device of the invention wherein a thin-walled heat shrinkable tubing 67 has been shrunk onto a length of the intermediate portion 64 of the flexible drive shaft 60. This tubing desirably extends distally from the distal end of the inner tubular shaft portion 194 of the socket 180 to a point located distally of the narrow opening 145 even when the longitudinally extendable tube 100 is at its maximum length. Preferably, the tubing 67 extends distally beyond the location where the fluid supply tubing delivers fluid to the drive shaft lumen, and optimally extends distally into the proximal end portion of the catheter. In one embodiment which has been found to work well, the tubing 67 extends distally from the distal end of the inner tubular shaft portion 194 of the socket 180 for a length of at least about 160 mm, and preferably for a length of about 200 mm. This embodiment uses a polyester heat shrinkable tubing manufactured with an average inner diameter of 28 mils and an average wall thickness of 0.4 mils, such as is commercially available from Advanced Polymers, Inc. of Salem, N.H., USA as item 028040BHGS.

Figure 61:
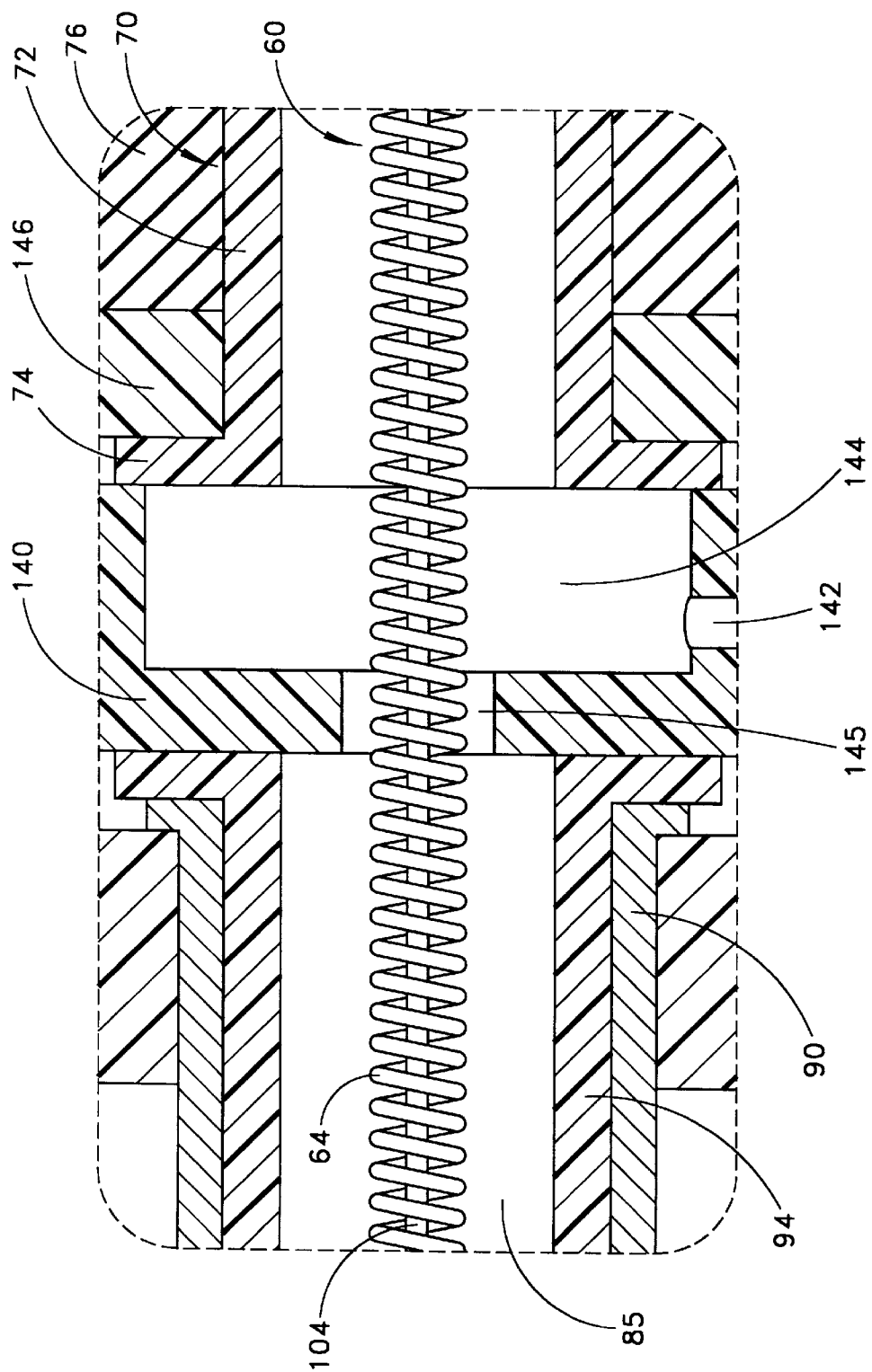
FIG. 61 is an enlarged view of that section outlined in FIG. 60 which shows where the fluid supply tubing delivers fluid to the drive shaft lumen.

It should be noted that FIGS. 61 and 62 are schematic and are not truly to scale. By way of example, in the embodiment of FIG. 62, one may use a flexible drive shaft 60 having an outer diameter of about 0.66 mm without the heat shrinkable tubing 67 and acquiring an outer diameter of about 0.69 mm after the tubing 67 has been heat shrunk on the drive shaft 60. In this illustrative embodiment, the narrow opening 145 has a diameter of about 0.80 mm and extends for about 3 mm. Fluid is supplied to the fluid-receiving recess 144, which is positioned distally of the narrow opening 145. As a result, more fluid will flow distally into the lumen of the catheter 70 than proximally into the lumen of the longitudinally extendable tube 100. As noted above, FIGS. 61 and 62 are not truly to scale and in the specific embodiment described above the fluid-receiving recess 144 has a diameter of about 1.1 mm.

Distally of the distal end of the heat shrinkable tubing 67, the fluid will pass between wire turns of the drive shaft 60 into the guide wire lumen of the drive shaft, thereby reducing friction between the drive shaft 60 and the guide wire 104. When the drive shaft 60 is rotated, the drive shaft will actively pump this fluid proximally along the guide wire lumen of the drive shaft. This pumping effect can be achieved by appropriately orienting the wire turns of the drive shaft and rotating the drive shaft in the appropriate direction.

In previous systems, a centrifugal pump rotated by the prime mover pumps fluid distally into a space defined by the telescoping tubes and then into the catheter. This generates significant pressure in that space, which will tend to urge the turbine block proximally. In order to move the tissue removal implement distally, the operator must apply significant manual force to the turbine block just to overcome this back pressure. This makes distal movement of the tissue removal implement more difficult and reduces the operator's tactile ability to gauge the force with which he is pressing the tissue removal implement against the stenosis.

One advantage of the illustrated invention is that the pressure of fluid within the longitudinally extendable tube 100 (telescoping tubes 82, 90) is reduced without compromising the flow of fluid distally through the catheter 70. As a result, the back pressure against the interconnected carriages 150, 200 is significantly reduced and the operator's tactile ability to gauge the force with which he is pressing the tissue removal implement against the stenosis is enhanced.

At the proximal end of the longitudinally extendable tube 100, fluid will flow proximally within the guide wire lumen of the proximal portion 62 of the drive shaft 60. Fluid also will flow proximally between the central core 170 of the drive shaft carriage 150 and the inner tubular shaft portion 194 of the drive shaft socket 180. The fluid flowing between the core 170 and the inner tubular shaft portion 194 will reduce friction between these two components and effectively serve as a fluid bearing, providing distal support to the tubular shaft of the drive shaft socket. In one useful embodiment, the inner diameter of this portion of the central core 170 is about 1.1 mm and the outer diameter of the inner tubular shaft portion 194 is about 1.07 mm. The fluid passing between the central core 170 and the tubular shaft 190 can drain out of the drive shaft carriage 150 through drainage outlets 176 passing through the central core 170 and the outer shell 152.

Most of the fluid which flows proximally within the guide wire lumen of the proximal portion 62 of the drive shaft 60 will tend to flow into the guide wire lumen 236 of the prime mover shaft 230. Some fluid may escape into the space surrounded by the guiding sleeve 220. To limit access of fluid to the distal bearing 252, the guiding sleeve 220 includes fluid drainage ports 224 which communicate with the fluid drainage ports 158 of the outer shell 152.

Figure 63:
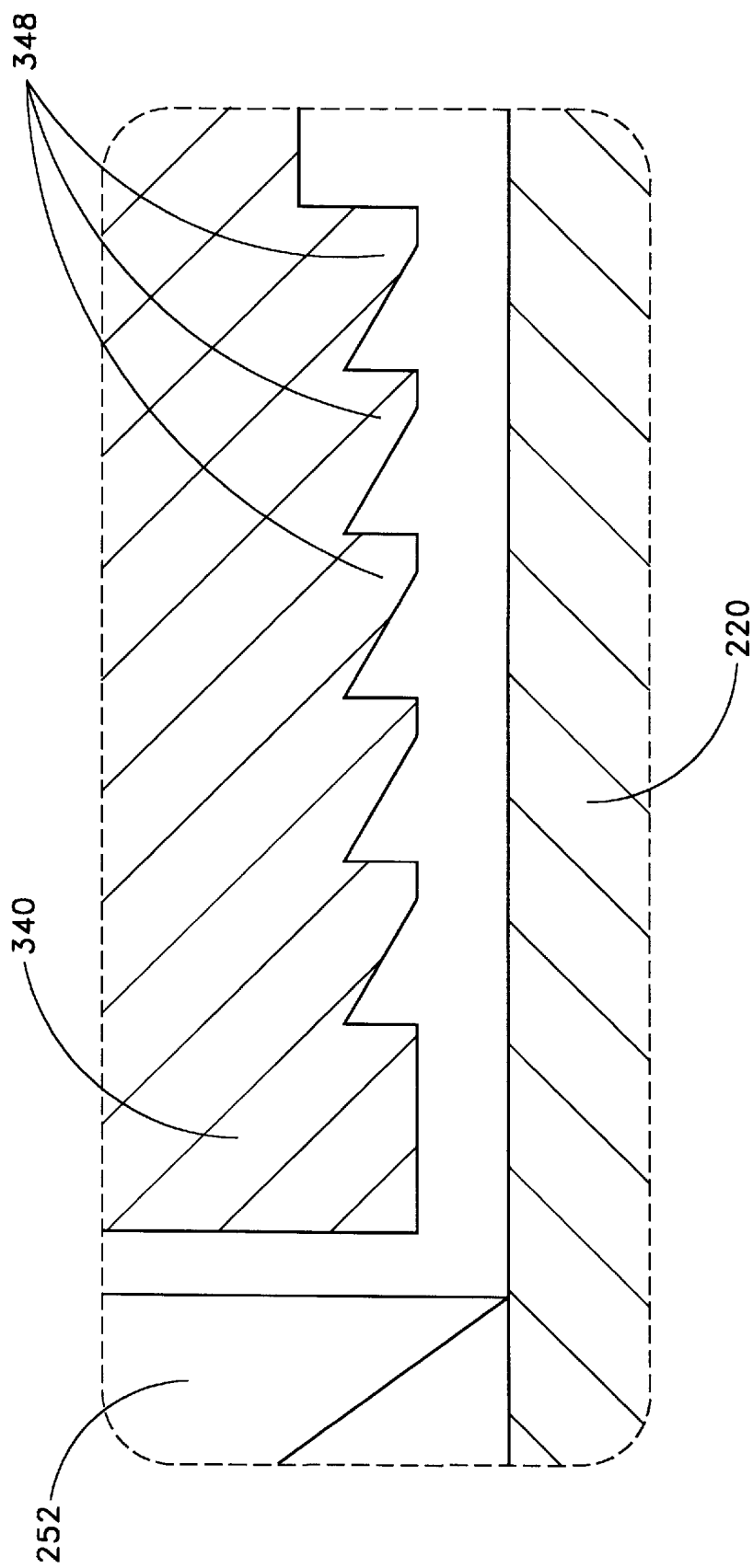
FIG. 63 is an enlarged view of that section outlined in FIG. 60 which shows a dynamic seal for urging fluid away from a bearing supporting the prime mover.

In one preferred embodiment, the coupling base 340 includes a dynamic seal 366 for urging fluid away from the distal bearing 252. As best seen in the enlarged view of FIG. 63, this dynamic seal is comprised of a series of generally frustoconical flanges 358 spaced along the proximal portion of the coupling base 340. Preferably, these frustoconical flanges 358 are formed integrally with the coupling base 340 and are oriented to flare outwardly in a distal direction. When the coupling base is rotated, these frustoconical flanges 358 will tend to urge fluid distally away from the distal bearing 252. As a result, each of the flanges acts as a barrier which centrifugally urges fluid distally in response to rotation of the prime mover.

In one embodiment which has been found to work well, there are five frustoconical flanges 358 in the dynamic seal 366. Each flange has a distal face which has a depth of about 0.4 mm. Each flange has a length of about 0.9 mm from the distal face of one flange to the distal face of the next flange. The frustoconical surface of each flange forms an angle of about 60° with respect to the distal face of the adjacent flange. There is a clearance of about 0.025 mm between the short cylindrical surface of each flange and the interior surface of the guiding sleeve 220.

In addition to the fluid drainage outlets already mentioned above, additional fluid drainage outlets can be provided. For example, the illustrated embodiment includes drainage outlets at the proximal and distal ends of the generally tubular housing 110 of the exchangeable drive shaft cartridge 80 to drain any fluid escaping into the housing from the longitudinally extendable tube 100.

Figure 64:
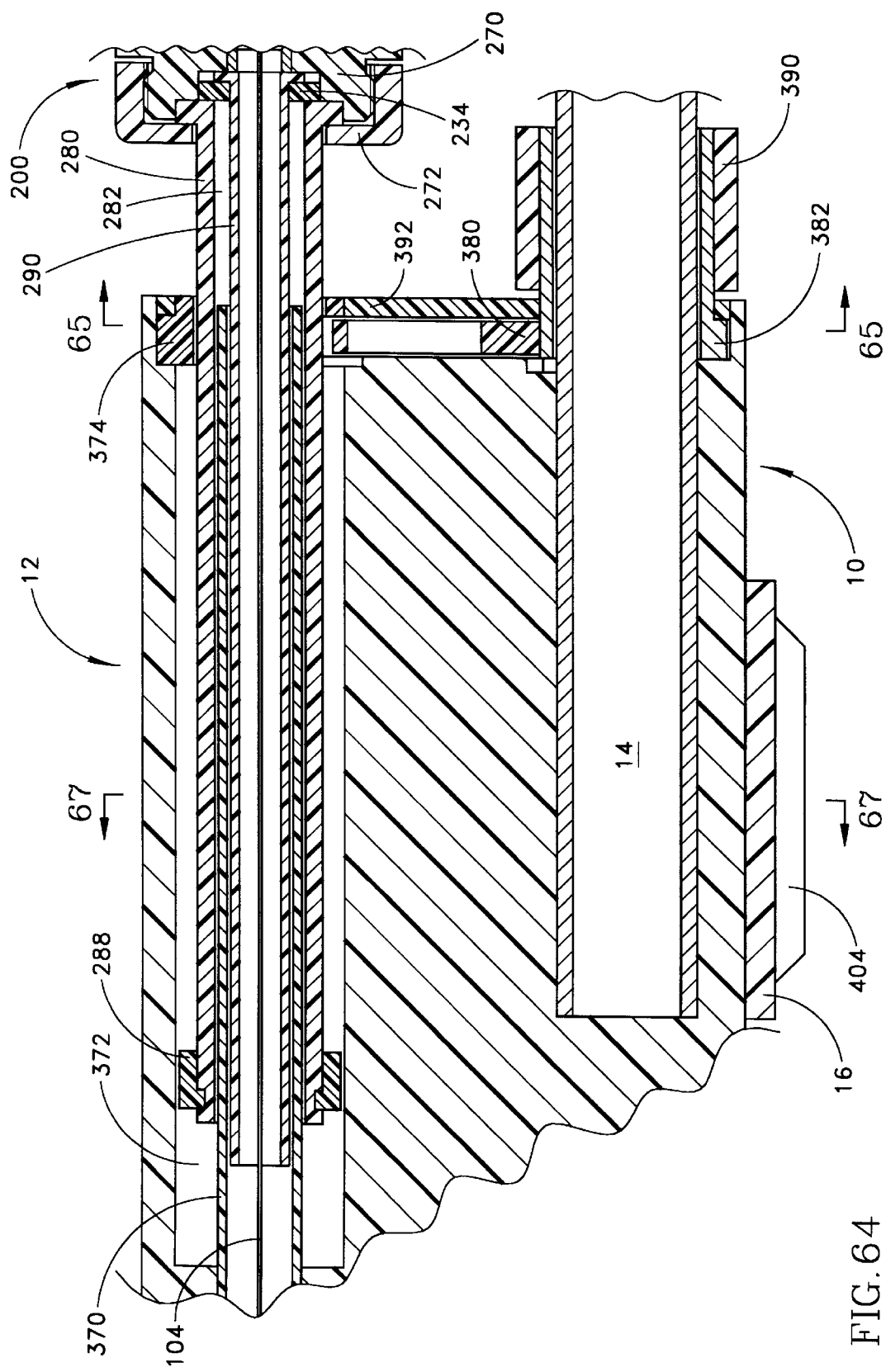
FIG. 64 is a broken-away, longitudinal cross sectional view of the proximal portion of the handle.

FIG. 64 is a broken-away, longitudinal cross sectional view of the proximal portion 12 of the handle 10 and the proximal end of the prime mover carriage 200. As noted above, two moveable proximal telescoping tubes 280 and 290 are secured to and extend proximally from the proximal bulkhead 270 of the prime mover carriage 200. These proximal telescoping tubes 280 and 290 are secured to the bulkhead 270 by the proximal cap 272 and the ring 234. The proximal outer telescoping tube 280 and the proximal inner telescoping tube 290 are moveable together with the prime mover carriage 200. As shown in the drawings, the proximal inner telescoping tube 290 has an outer diameter substantially smaller than the inner diameter of the proximal outer telescoping tube 280 so that an annular space 282 is formed between these two proximal telescoping tubes.

The moveable proximal telescoping tubes 280 and 290 are slidably received in the proximal portion 12 of the handle 10. In the illustrated embodiment, a stationary telescoping tube 370 is carried by the proximal portion 12 of the handle. This stationary telescoping tube 370 is disposed within a cylindrical recess in the proximal portion 12 of the handle. The stationary telescoping tube 370 is secured proximally to the proximal portion 12 of the handle. The stationary telescoping tube 370 has an outer diameter which is substantially smaller than the diameter of the cylindrical recess of the proximal portion 12 of the handle. As a result, there is an annular space 372 defined between the outer surface of the stationary telescoping tube 370 and the inner surface of the cylindrical recess.

The proximal outer telescoping tube 280 is slidably received in the annular space 372. The proximal inner telescoping tube 290 is slidably received within the stationary telescoping tube 370. As a consequence, when the prime mover carriage 200 is moved longitudinally with respect to the proximal portion 12 of the handle, the proximal telescoping tubes 280 and 290 will move longitudinally with respect to the stationary telescoping tube 370. Because the stationary telescoping tube 370 and both proximal telescoping tubes 280 and 290 desirably are round, the prime mover carriage 200 and the proximal telescoping tubes 280 and 290 may be rotated with respect to the proximal portion 12 of the handle.

To prevent the proximal telescoping tubes 280 and 290 from being removed from the proximal portion 12 of the handle, distal movement of the proximal outer telescoping tube 280 is limited by a pair of stops, one stop 288 being carried adjacent the proximal end of the proximal outer telescoping tube 280 and the other stop 374 being carried adjacent the distal end of the proximal portion 12 of the handle 10. To limit friction between the proximal outer telescoping tube 280 and the proximal portion 12 of the handle, these stops 288 and 374 may be formed of a low friction material such as polytetrafluoroethylene.

FIG. 64 also illustrates one possible manner of attaching the proximal portion 12 and intermediate portion 14 of the handle 10 to one another. In this embodiment, the intermediate portion 14 of the handle is formed of an elongate tube or rod. This tube may be press fitted, glued or otherwise secured within a mating recess in the proximal portion 12 of the handle. If so desired, the proximal portion 12 and intermediate portion 14 of the handle 10 could instead be integrally formed as a single component. The proximal portion 12 of the handle 10 optimally includes a detachable leg 16, discussed in more detail below in connection with FIG. 67.

Figure 65:
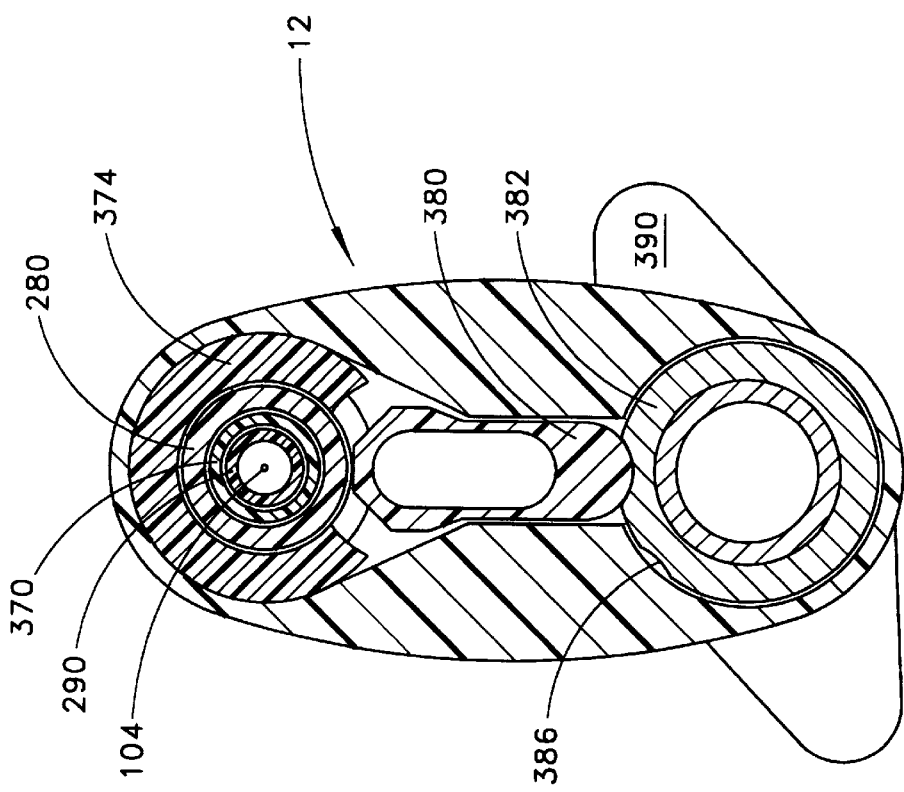
FIG. 65 is a transverse cross sectional view taken along line 65—65 in FIG. 64 and illustrating the carriage brake in an unlocked position wherein the telescoping tube attached to the prime mover carriage is free to move longitudinally.
Figure 66:
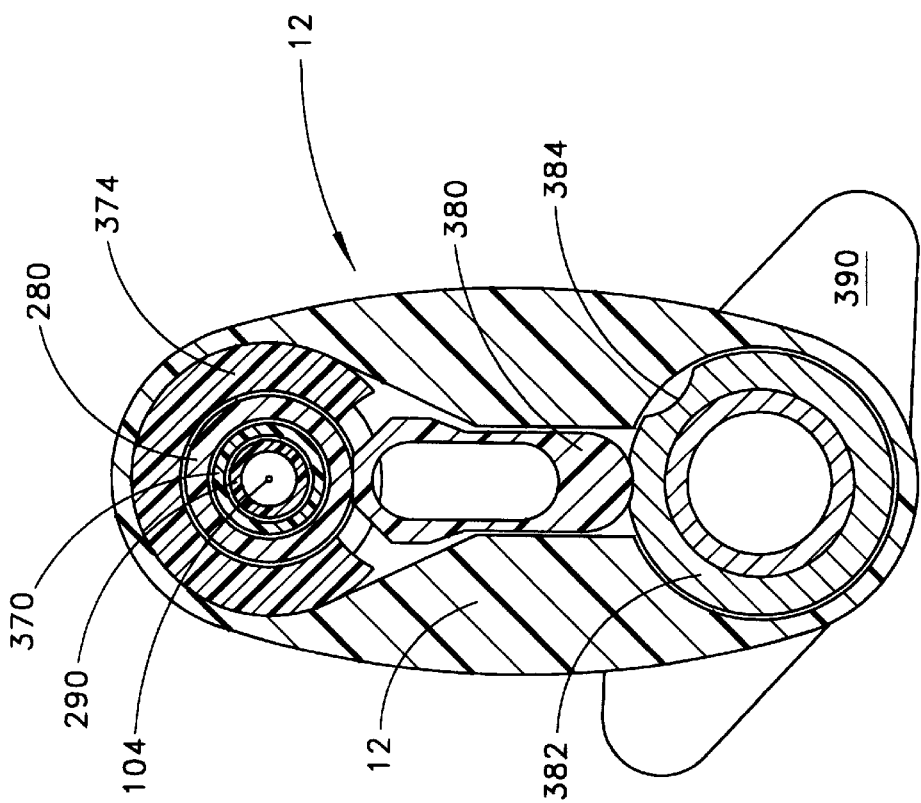
FIG. 66 is a cross sectional view similar to FIG. 65, but shows the carriage brake in a locked position wherein the telescoping tube attached to the prime mover carriage is prevented from moving longitudinally.

If so desired, the proximal portion 12 of the handle 10 may also include a carriage brake to lock the prime mover carriage 200 in a desired position. FIG. 64 shows this carriage brake in a longitudinal cross section at the distal end of the proximal portion 12 of the handle 10 while FIGS. 65 and 66 show the carriage brake in transverse cross section. The carriage brake generally includes a vertically moveable elongated braking shoe 380 and an actuating cam 382. A manually graspable actuating knob 390 is attached to the actuating cam 382 to enable a user to rotate the cam to engage and disengage the carriage brake. A distal plate 392 helps keep the braking shoe 380 and actuating cam 382 in place adjacent the distal end of the proximal portion 12 of the handle 10.

FIGS. 65 is a transverse cross sectional view taken along line 65—65 in FIG. 64 and illustrating the carriage brake in an unlocked position while FIG. 66 is a cross sectional view similar to FIG. 65, but showing the carriage brake in a locked position. As can be seen in these figures, the actuating cam 382 desirably has an unlocking recess 384 and a locking recess 386, with the locking recess being shallower than the unlocking recess. As shown in FIG. 65, when the lower end of the elongated braking shoe 380 is received in the unlocking recess of the actuating cam, the upper end of the elongated braking shoe 380 will be spaced away from the proximal outer telescoping tube 280. This permits the proximal outer telescoping tube 280 to move freely. As shown in FIG. 66, when the lower end of the elongated braking shoe 380 is received in the shallower locking recess of the actuating cam, the upper end of the elongated braking shoe 380 will be urged against the outer surface of the proximal outer telescoping tube 280. This will effectively lock the proximal outer telescoping tube 280 in place with respect to the proximal portion 12 of the handle.

Figure 67:
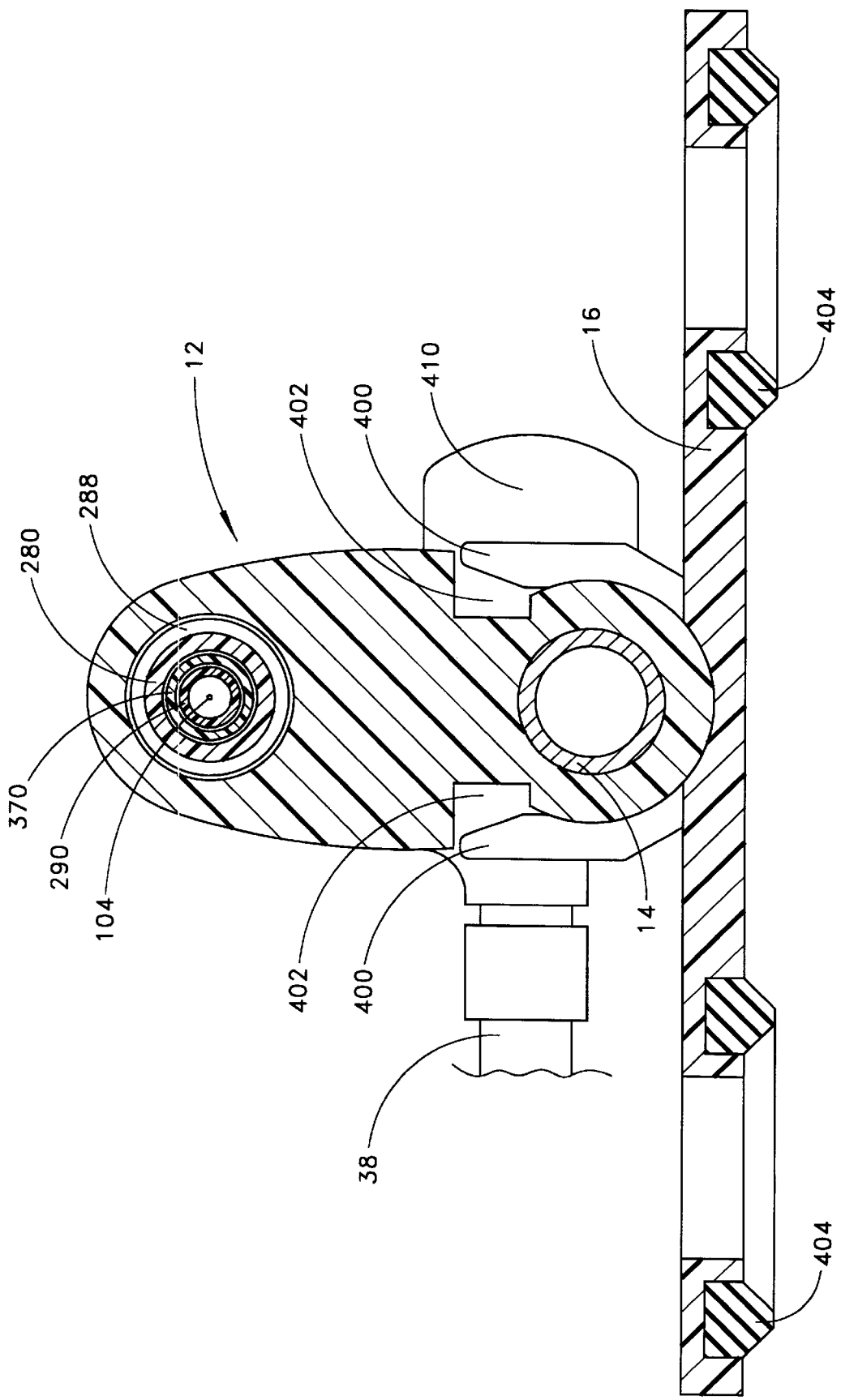
FIG. 67 is a transverse cross sectional view taken along line 67—67 in FIG. 65 and illustrating how a removable leg is clamped onto the proximal portion of the handle.

FIG. 67 is a transverse cross sectional view taken along line 67—67 in FIG. 64 and illustrating how a removable leg 16 is clamped onto the proximal portion 12 of the handle. As seen in FIG. 1, for example, there is a similar leg 16 clamped onto the distal portion 20 of the handle, as well. The legs help stabilize the handle 10 when an operator is placing an exchangeable drive shaft cartridge 80 in the groove 24 of the distal portion 20 of the handle 10 or removing an exchangeable drive shaft cartridge from the distal portion of the handle. The detachable legs 16, however, provide an operator with the ability to remove the legs during a procedure so he can manually grasp the distal portion 20 of the handle 10 with one hand while moving the interconnected carriages 150 and 200 with the other hand. Some operators or their assistants may also find it convenient to manually grasp the proximal portion 12 of the handle 10 when actuating the guide wire clamp override mechanism using the override button 410.

The legs 16 can be attached to the handle 10 using any one of a variety of disengageable mechanical linkages. A number of different mechanical linkages are described in U.S. patent application Ser. No. 08/792,102, filed 31 Jan. 1997, the teachings of which are incorporated herein by reference. In the illustrated embodiment, the legs 16 each comprise a horizontal foot and an upwardly extending clamp 400 for securing the leg 16 to the handle. The clamp has two pairs of upwardly extending arms sized and shaped to interlock with recesses 402 in the handle 10. One pair of such recesses 402 may be provided in each of the proximal portion 12 and distal portion 20 of the handle 10, permitting the legs 16 to be snapped on and off of the handle 10. Desirably, the legs 16 are interchangeable. If so desired, the horizontal foot of the leg 16 may also be provided with one or more pads 404.

While a preferred embodiment of the present invention has been described, it should be understood that various changes, adaptations and modifications may be made therein without departing from the spirit of the invention and the scope of the appended claims.

What is claimed is:

1. A rotational atherectomy device comprising:
   a. an exchangeable drive shaft cartridge comprising a rotatable drive shaft socket carried by a drive shaft carriage; a longitudinally extendable tube extending distally from the drive shaft carriage; an elongated catheter having a proximal end portion which is operatively connected to a distal end portion of the longitudinally extendable tube; and a rotatable flexible drive shaft having proximal, intermediate and distal portions, the proximal portion being attached to the drive shaft socket, the intermediate portion being disposed primarily within the tube and the catheter, and the distal portion extending distally from the catheter and having a tissue removal implement;
   b. a rotatable, radially expandable prime mover coupling connected to a prime mover for rotation therewith, the prime mover being carried by a prime mover carriage and the prime mover coupling including a radially expandable portion;
the drive shaft socket being sized to receive a length of the radially expandable portion of the prime mover coupling therein such that the radially expandable portion of the prime mover coupling does not effectively engage an interior surface of the drive shaft socket when the coupling is not rotating, but the radially expandable portion of the prime mover coupling radially expands to effectively engage the socket upon sufficiently rapid rotation of the prime mover, causing the socket and the drive shaft to rotate together with the prime mover coupling and the prime mover,
whereby when the prime mover is not rotating, the drive shaft is disconnected from the prime mover, thereby permitting the exchangeable drive shaft cartridge to be replaced by another exchangeable drive shaft cartridge.

2. The rotational atherectomy device of claim 1 wherein the radially expandable portion of the coupling resiliently regains a radially reduced dimension when it is not rotated, thereby disconnecting the drive shaft from the prime mover.

3. The rotational atherectomy device of claim 1 wherein the radially expandable portion of the prime mover coupling does not contact the interior surface of the drive shaft socket when the coupling is not rotating.

4. The rotational atherectomy device of claim 1 wherein the drive shaft socket includes a proximally extending engagement ring defining an interior engagement surface of the socket, the radially expandable portion of the coupling being adapted to radially expand into frictional engagement with the interior engagement surface of the socket in response to rotation of the prime mover shaft.

5. The rotational atherectomy device of claim 1 wherein the prime mover coupling further comprises a coupling base and the radially expandable portion of the coupling comprises at least two flexible pins, each pin being anchored adjacent one end thereof to the coupling base and having another end which is free to deflect radially outwardly to engage the drive shaft socket when the prime mover is rotated.

6. The rotational atherectomy device of claim 5 wherein the drive shaft socket includes a proximally extending engagement ring defining an interior engagement surface of the socket, the pins being adapted to deflect radially outwardly into frictional engagement with the interior engagement surface of the socket in response to rotation of the prime mover.

7. The rotational atherectomy device of claim 5 wherein the drive shaft socket includes a proximally extending engagement ring defining a generally cylindrical interior engagement surface of the socket, the pins being adapted to deflect radially outwardly into frictional engagement with the interior engagement surface of the socket in response to rotation of the prime mover.

8. The rotational atherectomy device of claim 5 wherein said pins are spaced equiangularly about an axis of the coupling base.

9. The rotational atherectomy device of claim 5 wherein there are at least six of said pins.

10. The rotational atherectomy device of claim 5 wherein each of the pins is formed of a superelastic material.

11. The rotational atherectomy device of claim 10 wherein said superelastic material is nitinol.

12. The rotational atherectomy device of claim 5 wherein an intermediate portion of each pin is received in a counterbore in the coupling base, each counterbore having an inner diameter greater than the outer diameter of the pin received therein.

13. The rotational atherectomy device of claim 5 wherein the coupling base includes at least one abutment spaced radially outwardly from each pin when the coupling base is not rotated and limiting outward deflection of an intermediate point along the length of the pin when the prime mover is rotated.

14. The rotational atherectomy device of claim 13 wherein the abutment comprises a single annular wall extending longitudinally from the coupling base and spaced radially outwardly from each of the pins when the coupling base is not rotated.

15. The rotational atherectomy device of claim 5 wherein the pins are integrally formed with the coupling base.

16. The rotational atherectomy device of claim 5 wherein the coupling base is integrally formed with a shaft of the prime mover.

17. The rotational atherectomy device of claim 5 wherein the pins, the coupling base and a shaft of the prime mover are all integrally formed.

18. The rotational atherectomy device of claim 5 wherein the prime mover carriage further comprises a coupling shield which restricts outward deflection of the free ends of the pins upon rotation of the prime mover when the free ends of the pins are not properly received within the drive shaft socket.

19. The rotational atherectomy device of claim 18 wherein the coupling shield is carried by the prime mover coupling and can be moved away from the free ends of the pins to permit the pins to be properly received within the socket so the pins can engage the drive shaft socket upon rotation of the prime mover.

20. The rotational atherectomy device of claim 1 wherein the prime mover coupling further comprises a coupling base and the radially expandable portion of the coupling comprises at least two flexible pins, each pin being anchored adjacent a proximal end to the coupling base and having a distal end which is free to deflect radially outwardly to engage an interior engagement surface of the drive shaft socket when the prime mover is rotated.

21. The rotational atherectomy device of claim 20 wherein the socket has a proximal end portion defining an interior surface, the pins being adapted to deflect radially outwardly into frictional engagement with the interior engagement surface of the socket in response to rotation of the prime mover shaft.

22. The rotational atherectomy device of claim 20 wherein said pins are spaced equiangularly about an axis of the coupling base.

23. The rotational atherectomy device of claim 20 wherein there are at least six of said pins.

24. The rotational atherectomy device of claim 20 wherein each of the pins is formed of a superelastic material.

25. The rotational atherectomy device of claim 24 wherein said superelastic material is nitinol.

26. The rotational atherectomy device of claim 20 wherein an intermediate portion of each pin is received in a counterbore in the coupling base, each counterbore having an inner diameter greater than the outer diameter of the pin received therein.

27. The rotational atherectomy device of claim 18 wherein the coupling base includes at least one abutment spaced radially outwardly from each pin when the coupling base is not rotated and limiting outward deflection of an intermediate point along the length of the pin when the prime mover is rotated.

28. The rotational atherectomy device of claim 27 wherein the abutment comprises a single annular wall extending longitudinally distally from the coupling base and spaced radially outwardly from each of the pins when the coupling base is not rotated.

29. The rotational atherectomy device of claim 20 wherein the pins are integrally formed with the coupling base.

30. The rotational atherectomy device of claim 20 wherein the coupling base is integrally formed with a shaft of the prime mover.

31. The rotational atherectomy device of claim 20 wherein the pins, the coupling base and a shaft of the prime mover are all integrally formed.

32. The rotational atherectomy device of claim 20 wherein the prime mover carriage further comprises a coupling shield which restricts outward deflection of the distal ends of the pins upon rotation of the prime mover when the distal ends of the pins are not properly received within the drive shaft socket.

33. The rotational atherectomy device of claim 32 wherein the coupling shield is carried by the base of the prime mover coupling and can be moved away from the distal ends of the pins to permit the pins to be properly received within the socket so the pins can engage the drive shaft socket upon rotation of the prime mover.

34. The rotational atherectomy device of claim 1 wherein the radially expandable portion of the prime mover coupling comprises an elastomeric, radially expandable tube, the tube being connected adjacent one end thereof to a prime mover shaft and having another end which is free to expand radially outwardly to engage the interior surface of the drive shaft socket when the prime mover is rotated.

35. The rotational atherectomy device of claim 34 wherein the radially expandable tube is connected to the prime mover shaft adjacent its proximal end and has a distal end which is free to expand radially outwardly.

36. The rotational atherectomy device of claim 35 wherein the tube has distal and intermediate portions which are both free to expand radially outwardly, the distal portion having a greater mass per unit length than the intermediate portion.

37. The rotational atherectomy device of claim 36 wherein the distal portion is thicker than the intermediate portion.

38. The rotational atherectomy device of claim 1 wherein the prime mover coupling further comprises a coupling base and the radially expandable portion of the coupling comprises at least two flyweights carried by the coupling base, each flyweight being free to move radially outwardly to engage an interior engagement surface of the drive shaft socket when the prime mover is rotated.

39. The rotational atherectomy device of claim 38 wherein each flyweight is slidably received in a radially extending bore in the coupling base, the coupling base including a circumferential stop for limiting outward movement of the flyweights.

40. The rotational atherectomy device of claim 38 wherein the interior engagement surface of the socket includes recesses for engaging the flyweights.

41. The rotational atherectomy device of claim 1 wherein the drive shaft carriage and the prime mover carriage are longitudinally moveable with respect to one another from an operational position wherein a length of the radially expandable portion of the prime mover coupling is received within the drive shaft socket to a non-operational position wherein the radially expandable portion of the prime mover coupling is withdrawn from the drive shaft socket.

42. The rotational atherectomy device of claim 41 wherein, in the operational position, the drive shaft carriage and the prime mover carriage are interconnected to move together as a unit to move the drive shaft and its tissue removal implement along a vascular lumen of a patient's body.

43. The rotational atherectomy device of claim 42 further comprising fittings associated with the drive shaft carriage and the prime mover carriage, the fittings being designed to fix the relative positions of the drive shaft socket and the prime mover coupling in the operational position.

44. The rotational atherectomy device of claim 43 wherein the fittings are connected to one another at three or more equiangularly spaced positions.

45. The rotational atherectomy device of claim 43 wherein at least one of the fittings is free to rotate with respect to the carriage with which it is associated to facilitate connection of the carriages to one another.

46. The rotational atherectomy device of claim 43 wherein the fittings comprise mating components of a bayonet joint.

47. The rotational atherectomy device of claim 1 wherein the drive shaft carriage and the prime mover carriage are provided with mating components of a bayonet joint to connect the carriages to one another.

48. The rotational atherectomy device of claim 47 wherein the mating components comprise pins and slots, the pins being carried by one of the carriages and the slots being formed in a bayonet collar carried by the other carriage.

49. The rotational atherectomy device of claim 48 wherein the bayonet collar is rotatable about the carriage which carries the bayonet collar.

50. The rotational atherectomy device of claim 47 wherein the bayonet joint connects the carriages to one another at three or more equiangularly spaced positions.

51. The rotational atherectomy device of claim 1 wherein the exchangeable drive shaft cartridge further comprises a generally tubular housing carrying the longitudinally extendable tube.

52. The rotational atherectomy device of claim 51 wherein the tubular housing of the drive shaft cartridge has a generally cylindrical outer surface.

53. The rotational atherectomy device of claim 51 wherein the longitudinally extendable tube includes outer and inner telescoping tubes, the outer telescoping tube being connected to the drive shaft carriage and the inner telescoping tube being connected to a distal end piece of the tubular housing.

54. The rotational atherectomy device of claim 53 wherein the outer telescoping tube is slidably received in an elongated annular space defined between an inner surface of the tubular housing and an outer surface of the inner telescoping tube.

55. The rotational atherectomy device of claim 54 wherein the outer telescoping tube is moveable both longitudinally and rotationally with respect to both the tubular housing and the in telescoping tube.

56. The rotational atherectomy device of claim 54 further comprising complementary fittings associated with the tubular housing and the drive shaft carriage for releasably locking the drive shaft carriage to the tubular housing when a majority of the length of the outer telescoping tube is received within the tubular housing of the drive shaft cartridge.

57. The rotational atherectomy device of claim 56 wherein the complementary fittings comprise at least one tab carried by one of the tubular housing and the drive shaft carriage and a flange carried by the other one of the tubular housing and the drive shaft carriage.

58. The rotational atherectomy device of claim 56 wherein the outer telescoping tube is free to rotate with respect to both the tubular housing and the inner telescoping tube when the drive shaft carriage is releasably locked to the tubular housing of the cartridge.

59. The rotational atherectomy device of claim 1 further comprising a handle which carries the prime mover carriage and which is adapted to releasably hold the drive shaft cartridge.

60. The rotational atherectomy device of claim 59 wherein the handle includes at least one clamp for releasably holding a generally tubular housing of the drive shaft cartridge.

61. The rotational atherectomy device of claim 59 wherein the prime mover carriage is longitudinally moveable with respect to the handle.

62. The rotational atherectomy device of claim 59 wherein the drive shaft carriage is longitudinally moveable with respect to the handle when the drive shaft cartridge is releasably held by the handle.

63. The rotational atherectomy device of claim 59 wherein the drive shaft carriage and the prime mover carriage are adapted to be interconnected for movement together as a unit longitudinally with respect to the handle.

64. The rotational atherectomy device of claim 59 wherein the drive shaft carriage and the prime mover carriage are adapted to be interconnected for movement together as a unit both longitudinally and rotationally with respect to the handle.

65. The rotational atherectomy device of claim 59 wherein an axis of the drive shaft carriage is substantially aligned with an axis of the prime mover carriage when the drive shaft cartridge is releasably held by the handle.

66. The rotational atherectomy device of claim 59 wherein the drive shaft carriage and the prime mover carriage are moveable with respect to one another longitudinally along their aligned axes from an operational position wherein a length of the radially expandable portion of the prime mover coupling is received within the drive shaft socket to a non-operational position wherein the radially expandable portion of the prime mover coupling is withdrawn from the drive shaft socket.

67. The rotational atherectomy device of claim 66 wherein the drive shaft carriage and the prime mover carriage are adapted to be interconnected for movement together as a unit longitudinally with respect to the handle along their aligned axes.

68. The rotational atherectomy device of claim 59 wherein the handle comprises a distal portion adapted to releasably hold the drive shaft cartridge, a proximal portion carrying the prime mover carriage, and an elongated rod connecting the distal and proximal portions of the handle to one another.

69. The rotational atherectomy device of claim 68 further comprising a telescoping tube slidably received in the proximal portion of the handle and having a distal end connected to the prime mover carriage.

70. The rotational atherectomy device of claim 69 wherein the elongated rod of the handle extends generally parallel to the telescoping tube connected to the prime mover carriage and is spaced therefrom a distance sufficient to permit both the drive shaft carriage and the prime mover carriage to move parallel to the elongated rod of the handle.

71. The rotational atherectomy device of claim 68 wherein the drive shaft carriage and the prime mover carriage are adapted to be interconnected for movement together as a unit longitudinally with respect to the handle.

72. The rotational atherectomy device of claim 68 wherein the drive shaft carriage and the prime mover carriage are adapted to be interconnected for movement together as a unit both longitudinally and rotationally with respect to the handle.

73. The rotational atherectomy device of claim 68 wherein the distal portion of the handle includes a pair of opposing walls defining a longitudinally extending groove for releasably holding a length of the drive shaft cartridge therein.

74. The rotational atherectomy device of claim 73 further comprising a slot in one of the opposing walls for receiving a flexible fluid supply tubing therein.

75. The rotational atherectomy device of claim 73 wherein the groove has a depth greater than an outer diameter of a tubular housing of the drive shaft cartridge, thereby limiting manual pressure on the tubular housing when a user grasps the handle around the groove.

76. The rotational atherectomy device of claim 73 wherein the distal portion of the handle includes at least one clamp for retaining the drive shaft cartridge in the groove.

77. The rotational atherectomy device of claim 76 wherein the handle includes two clamps, the clamps being spaced from one another longitudinally along the distal portion of the handle.

78. The rotational atherectomy device of claim 76 wherein the clamp is sized to releasably hold a generally tubular housing of the drive shaft cartridge.

79. The rotational atherectomy device of claim 78 wherein the groove in the distal portion of the handle has a depth greater than an outer diameter of the tubular housing of the drive shaft cartridge.

80. The rotational atherectomy device of claim 80 wherein the groove is upwardly open.

81. The rotational atherectomy device of claim 80 wherein the side walls defining the groove are sized to extend above the tubular housing to limit manual pressure on the tubular housing when a user grasps the handle around the groove.

82. The rotational atherectomy device of claim 76 wherein the clamp and the opposing walls defining the groove are all formed as a single component.

83. The rotational atherectomy device of claim 76 wherein the clamp and the distal portion of the handle are formed as a single component.

84. The rotational atherectomy device of claim 76 wherein the clamp, the opposing walls defining the groove and the distal portion of the handle are all formed as a single component.

85. The rotational atherectomy device of claim 76 wherein the clamp includes two opposing sides, one side of the clamp being integrally formed with one of the walls and the other side of the clamp being integrally formed with the other wall.

86. The rotational atherectomy device of claim 76 wherein the distal portion of the handle comprises two laterally opposed mating elements, one of the opposed walls and one side of the clamp being integrally formed with one of the mating elements, the other of the walls and another side of the clamp being integrally formed with another of the mating elements.

87. The rotational atherectomy device of claim 87 further comprising at least one leg removably interlockable with the handle.

88. The rotational atherectomy device of claim 87 wherein the leg includes a clamp sized and shaped to releasably interlock with the handle.

89. The rotational atherectomy device of claim 1 further comprising a flexible fluid supply tubing attached to the exchangeable drive shaft cartridge and in fluid communication with a drive shaft lumen of the drive shaft cartridge, the drive shaft lumen being defined by a lumen of the catheter and a lumen of the longitudinally extendable tube.

90. The rotational atherectomy device of claim 89 wherein the drive shaft lumen receives a majority of the length of the drive shaft.

91. The rotational atherectomy device of claim 89 wherein the drive shaft lumen includes a reduced inner diameter segment, the reduced inner diameter segment being positioned proximally of where the fluid supply tubing delivers fluid to the drive shaft lumen, thereby reducing flow of fluid proximally along the drive shaft lumen.

92. The rotational atherectomy device of claim 91 wherein a sufficient clearance exists between the drive shaft and the interior of the reduced inner diameter segment of the drive shaft lumen to permit a restricted flow of fluid proximally along the drive shaft lumen.

93. The rotational atherectomy device of claim 91 wherein a thin-walled tubing extends along a proximal length of an intermediate portion of the drive shaft from a distal end of a tubular shaft of the drive shaft socket to a point located distally of a proximal end of the reduced inner diameter segment of the drive shaft lumen.

94. The rotational atherectomy device of claim 93 wherein the thin-walled tubing extends distally beyond a distal end of the reduced inner diameter segment of the drive shaft lumen.

95. The rotational atherectomy device of claim 93 wherein the thin-walled tubing extends distally beyond the location where the fluid supply tubing delivers fluid to the drive shaft lumen.

96. The rotational atherectomy device of claim 93 wherein the thin-walled tubing extends distally into the proximal end portion of the catheter.

97. The rotational atherectomy device of claim 93 wherein the thin-walled tubing is a heat-shrinkable tubing.

98. The rotational atherectomy device of claim 93 wherein the thin-walled tubing is a heat-shrinkable polyester tubing.

99. The rotational atherectomy device of claim 93 wherein the thin-walled tubing extends for a length not less than about 160 mm.

100. The rotational atherectomy device of claim 89 wherein the fluid supply tubing delivers fluid from a fluid supply external the cartridge.

101. The rotational atherectomy device of claim 89 wherein the fluid supply tubing has two ends, one end being attached to the drive shaft cartridge distally of the drive shaft socket and the other end of the tubing being in fluid communication with an external fluid supply.

102. The rotational atherectomy device of claim 89 wherein the fluid supply tubing is attached to the drive shaft cartridge distally of the drive shaft socket.

103. The rotational atherectomy device of claim 89 wherein the fluid supply tubing is attached to the drive shaft cartridge distally of the drive shaft socket and proximally of the catheter.

104. The rotational atherectomy device of claim 89 wherein the fluid supply tubing is attached to the drive shaft cartridge adjacent a distal end of the longitudinally extendable tube.

105. The rotational atherectomy device of claim 89 wherein the longitudinally extendable tube includes at least two telescoping tubes.

106. The rotational atherectomy device of claim 105 wherein the fluid supply tubing is attached to the drive shaft cartridge distally of at least one of the telescoping tubes.

107. The rotational atherectomy device of claim 105 wherein the fluid supply tubing is attached to the drive shaft cartridge distally of all of the telescoping tubes.

108. The rotational atherectomy device of claim 105 wherein the fluid supply tubing is attached to the drive shaft cartridge distally of at least one of the telescoping tubes and proximally of the catheter.

109. The rotational atherectomy device of claim 105 wherein the fluid supply tubing is attached to the drive shaft cartridge primally of the catheter.

110. The rotational atherectomy device of claim 89 wherein the drive shaft comprises a helically wound coil which defines a guide wire lumen of the drive shaft, fluid supplied to the drive shaft lumen passing between wire turns of the drive shaft into the guide wire lumen.

111. The rotational atherectomy device of claim 110 wherein a generally tubular shaft of the prime mover defines a guide wire lumen which extends proximally from the guide wire lumen of the drive shaft when the radially expandable portion of the prime mover coupling is received in the drive shaft socket.

112. The rotational atherectomy device of claim 111 wherein the guide wire lumen of the drive shaft and the guide wire lumen of the prime mover shaft are aligned and in fluid communication with one another when the radially expandable portion of the prime mover coupling is received in the drive shaft socket, thereby permitting the drive shaft and the prime mover to be advanced together as a unit over the guide wire.

113. The rotational atherectomy device of claim 111 wherein the guide wire lumen of the drive shaft and the guide wire lumen of the prime mover shaft are aligned and in fluid communication with one another when the radially expandable portion of the prime mover coupling is received in the drive shaft socket, thereby permitting the drive shaft and the prime mover to be rotated together as a unit over the guide wire.

114. The rotational atherectomy device of claim 111 wherein the guide wire lumen of the drive shaft and the guide wire lumen of the prime mover shaft are aligned and in fluid communication with one another when the radially expandable portion of the prime mover coupling is received in the drive shaft socket, thereby permitting the drive shaft and the prime mover to be advanced and rotated together as a unit over the guide wire.

115. The rotational atherectomy device of claim 111 wherein the guide wire lumen of the prime mover shaft is in fluid communication with a fluid outlet located adjacent a proximal end of the prime mover shaft.

116. The rotational atherectomy device of claim 111 further comprising a helically wound coil disposed within the guide wire lumen of the prime mover shaft, the coil being rotatable together with the prime mover.

117. The rotational atherectomy device of claim 116 wherein the coil disposed within the prime mover shaft is oriented to urge fluid proximally when the prime mover is rotated.

118. The rotational atherectomy device of claim 111 wherein the drive shaft socket includes a proximally oriented face and a central extension which extends proximally from that face, the guide wire lumen of the prime mover shaft slidably receiving a proximal length of the central extension of the socket when the radially expandable portion of the prime mover coupling is received in the drive shaft socket such that the guide wire lumen of the drive shaft is in fluid communication with the guide wire lumen of the prime mover shaft.

119. The rotational atherectomy device of claim 1 wherein the prime mover coupling includes a dynamic seal for urging fluid away from a bearing supporting a shaft of the prime mover.

120. The rotational atherectomy device of claim 119 wherein the dynamic seal includes a barrier centrifugally urging fluid distally in response to rotation of the prime mover.

121. The rotational atherectomy device of claim 120 wherein the barrier comprises a generally frustoconical flange carried by a proximal portion of the prime mover coupling.

122. The rotational atherectomy device of claim 121 further comprising a plurality of such barriers spaced along the proximal portion of the prime mover coupling.

123. The rotational atherectomy device of claim 1 wherein the prime mover carriage further comprises a coupling shield which restricts radial expansion of the radially expandable portion of the prime mover coupling upon rotation of the prime mover when the radially expandable portion of the prime mover coupling is not properly received within the drive shaft socket.

124. The rotational atherectomy device of claim 123 wherein the coupling shield is carried by the prime mover coupling and can be moved away from a distal end of the coupling to permit the radially expandable portion of the coupling to be properly received within the socket so the radially expandable portion of the coupling can engage the drive shaft socket upon rotation of the prime mover.

125. The rotational atherectomy device of claim 124 wherein the coupling shield is biased toward the distal end of the prime mover coupling.

126. The rotational atherectomy device of claim 124 wherein the coupling shield is carried by a base of the prime mover coupling and is biased toward the distal end of the coupling by a compression spring disposed proximally of the shield around the base of the coupling.

127. The rotational atherectomy device of claim 126 wherein the shield presents a generally annular distal face, the distal face of the shield being sized to abut the drive shaft socket, thereby permitting the drive shaft socket to move the shield away from the distal end of the coupling to permit the radially expandable portion of the coupling to be properly received within the socket.

128. The rotational atherectomy device of claim 127 wherein the shield comprises an annular collar which surrounds a length of the radially expandable portion of the coupling.

129. The rotational atherectomy device of claim 128 wherein the base of the prime mover coupling and the collar are fitted together in a tongue-in-groove relationship to guide the collar generally longitudinally along the coupling base and limit rotation of the collar with respect to the base.

130. The rotational atherectomy device of claim 1 wherein the drive shaft carriage further comprises a bearing which supports the drive shaft socket.

131. The rotational atherectomy device of claim 130 wherein the bearing is a ball bearing.

132. The rotational atherectomy device of claim 1 wherein the longitudinally extendable tube includes at least two telescoping tubes.

133. The rotational atherectomy device of claim 132 wherein one of the telescoping tubes is connected to a distal end piece of a housing of the exchangeable drive shaft cartridge while another of the telescoping tubes carries the drive shaft carriage.

134. A rotational atherectomy device comprising:
   a) an exchangeable drive shaft cartridge comprising a rotatable drive shaft socket carried by a drive shaft carriage; a catheter; and a rotatable flexible drive shaft having a proximal, intermediate and distal portions, the proximal portion of the drive shaft being attached to the drive shaft socket, the intermediate portion of the drive shaft being disposed primarily within the catheter, and the distal portion of the drive shaft extending distally from the catheter and having an abrasive tissue removal implement;
   b) a rotatable prime mover coupling attached to a shaft of a prime mover for rotation therewith, the prime mover coupling including a radially expandable portion;
the drive shaft socket being sized to receive a length of the radially expandable portion of the coupling therein such that the radially expandable portion of the coupling does not contact an interior of the drive shaft socket when the prime mover coupling is not rotating, but the radially expandable portion of the coupling radially expands into frictional engagement with the socket upon sufficiently rapid rotation of the prime mover, causing the socket and the drive shaft to rotate together with the prime mover coupling and the prime mover,
whereby when the prime mover is not rotating, the drive shaft is disconnected from the prime mover, thereby permitting the exchangeable drive shaft cartridge to be replaced by another exchangeable drive shaft cartridge.

135. A rotational atherectomy device comprising:
   a) an exchangeable drive shaft cartridge comprising a rotatable drive shaft socket carried by a drive shaft carriage; a longitudinally extendable tube extending distally from the drive shaft carriage; a catheter extending distally from the tube; and a flexible drive shaft having a lumen for receiving a guidewire around which the drive shaft may rotate, the drive shaft having proximal, intermediate and distal portions, the proximal portion being attached to the drive shaft socket, the intermediate portion being disposed primarily within the tube and the catheter, and the distal portion extending distally from the catheter and having an abrasive tissue removal implement;

b) a rotatable prime mover coupling attached to a shaft of a prime mover for rotation therewith, the prime mover coupling including a radially expandable portion;

the drive shaft socket being sized to receive a length of the radially expandable portion of the coupling therein such that the radially expandable portion of the coupling does not contact an interior of the drive shaft socket when the prime mover coupling is not rotating, but the radially expandable portion of the coupling radially expands into frictional engagement with the socket upon sufficiently rapid rotation of the prime mover, causing the socket and the drive shaft to rotate together with the prime mover coupling and the prime mover, whereby when the prime mover is not rotating, the drive shaft is disconnected from the prime mover, thereby permitting the exchangeable drive shaft cartridge to be replaced by another exchangeable drive shaft cartridge.

136. The rotational atherectomy device of claim 134 or claim 135 wherein the prime mover and the rotatable prime mover coupling are carried by a prime mover carriage, the prime mover carriage and the drive shaft carriage having mating fittings which permit the carriages to be interconnected so they can be moved together as a unit.

137. The rotational atherectomy device of claim 136 wherein the fittings comprise mating components of a bayonet joint.

138. A rotational atherectomy device comprising:

a) an exchangeable drive shaft cartridge comprising a rotatable drive shaft socket carried by a drive shaft carriage; a longitudinally extendable tube extending distally from the drive shaft carriage; a catheter extending distally from the tube; and a rotatable flexible drive shaft having proximal, intermediate and distal portions, the proximal portion being attached to the drive shaft socket, the intermediate portion being disposed primarily within the tube and the catheter, and the distal portion extending distally from the catheter and having an abrasive tissue removal implement;

b) a flexible fluid supply tubing connected to the drive shaft cartridge distally of the drive shaft socket;

c) a rotatable prime mover coupling carried by a prime mover carriage and connected to a prime mover for rotation therewith, the prime mover coupling including a coupling base and at least two flexible pins, each pin being formed of a superelastic material and connected adjacent a proximal end to the coupling base and having a distal end portion which is free to deflect radially outwardly into frictional engagement with an interior surface of the drive shaft socket when the prime mover is rotated;

d) the drive shaft carriage and the prime mover carriage including mating fittings which permit the carriages to be interconnected to move together as a unit;

the drive shaft socket being sized to receive the distal end portions of the pins of the prime mover coupling therein such that the pins do not contact the interior surface of the drive shaft socket when the coupling is not rotating, but the distal end portions of the pins deflect into frictional engagement with the socket upon sufficiently rapid rotation of the prime mover, causing the socket and the drive shaft to rotate together with the prime mover coupling and the prime mover, whereby when the prime mover is not rotating, the drive shaft is disconnected from the prime mover, thereby permitting the exchangeable drive shaft cartridge to be replaced by another exchangeable drive shaft cartridge.

139. A rotational atherectomy device comprising:

a) an exchangeable drive shaft cartridge comprising a rotatable drive shaft socket carried by a drive shaft carriage; a longitudinally extendable tube extending distally from the drive shaft carriage; a catheter extending distally from the tube; and a rotatable flexible drive shaft having proximal, intermediate and distal portions, the proximal portion being attached to the drive shaft socket, the intermediate portion being disposed primarily within the tube and the catheter, and the distal portion extending distally from the catheter and having an abrasive tissue removal implement;

b) a flexible fluid supply tubing connected to the drive shaft cartridge distally of the drive shaft socket;

c) a rotatable prime mover coupling carried by a prime mover carriage and connected to a prime mover for rotation therewith, the prime mover coupling including a coupling base and at least six flexible pins, each pin being formed of a superelastic material and connected adjacent a proximal end to the coupling base and having a distal end portion which is free to deflect radially outwardly into frictional engagement with an interior surface of the drive shaft socket when the prime mover is rotated;

d) the drive shaft carriage and the prime mover carriage including mating fittings which permit the carriages to be interconnected to move together as a unit;

the drive shaft socket being sized to receive the distal end portions of the pins of the prime mover coupling therein such that the pins do not contact the interior surface of the drive shaft socket when the coupling is not rotating, but the distal end portions of the pins deflect into frictional engagement with the socket upon sufficiently rapid rotation of the prime mover, causing the socket and the drive shaft to rotate together with the prime mover coupling and the prime mover, whereby when the prime mover is not rotating, the drive shaft is disconnected from the prime mover, thereby permitting the exchangeable drive shaft cartridge to be replaced by another exchangeable drive shaft cartridge.

140. A rotational atherectomy device comprising:

a) an exchangeable drive shaft cartridge comprising a rotatable drive shaft socket carried by a drive shaft carriage; a longitudinally extendable tube extending distally from the drive shaft carriage; a catheter extending distally from the tube; and a rotatable flexible drive shaft having proximal, intermediate and distal portions, the proximal portion being attached to the drive shaft socket, the intermediate portion being disposed primarily within the tube and the catheter, and the distal portion extending distally from the catheter and having an abrasive tissue removal implement;

b) a flexible fluid supply tubing connected to the drive shaft cartridge distally of the drive shaft socket;

c) a rotatable prime mover coupling carried by a prime mover carriage and connected to a prime mover for rotation therewith, the prime mover coupling including a coupling base and at least two flexible pins, each pin being formed of a superelastic material and connected adjacent a proximal end to the coupling base and having a distal end portion which is free to deflect radially outwardly into frictional engagement with an interior surface of the drive shaft socket when the prime mover is rotated;

d) the drive shaft carriage and the prime mover carriage including mating components of a bayonet joint to connect the carriages to one another to permit the carriages to move together as a unit;

the drive shaft socket being sized to receive the distal end portions of the pins of the prime mover coupling therein such that the pins do not contact the interior surface of the drive shaft socket when the coupling is not rotating, but the distal end portions of the pins deflect into frictional engagement with the socket upon sufficiently rapid rotation of the prime mover, causing the socket and the drive shaft to rotate together with the prime mover coupling and the prime mover, whereby when the prime mover is not rotating, the drive shaft is disconnected from the prime mover, thereby permitting the exchangeable drive shaft cartridge to be replaced by another exchangeable drive shaft cartridge.

141. A rotational atherectomy device comprising:

a) an exchangeable drive shaft cartridge comprising a rotatable drive shaft socket carried by a drive shaft carriage; a longitudinally extendable tube extending distally from the drive shaft carriage; a catheter extending distally from the tube; and a rotatable flexible drive shaft having proximal, intermediate and distal portions, the proximal portion being attached to the drive shaft socket, the intermediate portion being disposed primarily within the tube and the catheter, and the distal portion extending distally from the catheter and having an abrasive tissue removal implement;

b) a flexible fluid supply tubing connected to the drive shaft cartridge distally of the drive shaft socket;

c) a rotatable prime mover coupling carried by a prime mover carriage and connected to a prime mover for rotation therewith, the prime mover coupling including a coupling base and at least six flexible pins, each pin being formed of a superelastic material and connected adjacent a proximal end to the coupling base and having a distal end portion which is free to deflect radially outwardly into frictional engagement with an interior surface of the drive shaft socket when the prime mover is rotated;

d) the drive shaft carriage and the prime mover carriage including mating components of a bayonet joint to connect the carriages to one another to permit the carriages to move together as a unit;

the drive shaft socket being sized to receive the distal end portions of the pins of the prime mover coupling therein such that the pins do not contact the interior surface of the drive shaft socket when the coupling is not rotating, but the distal end portions of the pins deflect into frictional engagement with the socket upon sufficiently rapid rotation of the prime mover, causing the socket and the drive shaft to rotate together with the prime mover coupling and the prime mover, whereby when the prime mover is not rotating, the drive shaft is disconnected from the prime mover, thereby permitting the exchangeable drive shaft cartridge to be replaced by another exchangeable drive shaft cartridge.

142. The rotational atherectomy device of claim 141 further comprising a flexible fluid supply tubing attached to the exchangeable drive shaft cartridge and in fluid communication with a drive shaft lumen of the drive shaft cartridge, the drive shaft lumen including a reduced inner diameter segment, the reduced inner diameter segment being positioned proximally of where the fluid supply tubing delivers fluid to the drive shaft lumen, thereby reducing flow of fluid proximally along the drive shaft lumen.

143. A rotational atherectomy device comprising:

a) an exchangeable drive shaft cartridge comprising a rotatable drive shaft socket carried by a drive shaft carriage; and a rotatable flexible drive shaft having a proximal, intermediate and distal portions, the proximal portion being attached to the drive shaft socket, the intermediate portion being disposed primarily within a catheter, and the distal portion extending distally from the catheter and having a tissue removal implement;

b) a flexible fluid supply tubing connected to the drive shaft cartridge distally of the drive shaft socket;

c) a rotatable, radially expandable prime mover coupling carried by a prime mover carriage and connected to a prime mover for rotation therewith;

the drive shaft socket being sized to receive a length of the prime mover coupling therein such that the prime mover coupling does not effectively engage an interior of the drive shaft socket when the coupling is not rotating, but the prime mover coupling radially expands to effectively engage the socket upon sufficiently rapid rotation of the prime mover, causing the socket and the drive shaft to rotate together with the prime mover coupling and the prime mover, whereby when the prime mover is not rotating, the drive shaft is disconnected from the prime mover, thereby permitting the exchangeable drive shaft cartridge to be replaced by another exchangeable drive shaft cartridge.

144. The rotational atherectomy device of claim 143 wherein one of the prime mover carriage and the drive shaft carriage is stationary and the other of the prime mover carriage and the drive shaft carriage can be moved longitudinally with respect to the stationary carriage.

145. A rotational atherectomy device comprising:

a. an exchangeable drive shaft cartridge comprising a housing; a drive shaft carriage positioned proximally of the housing; a rotatable drive shaft socket carried by the drive shaft carriage; a flexible fluid supply tubing connected to the housing distally of the drive shaft socket; a catheter extending distally from the housing; and a rotatable flexible drive shaft having proximal, intermediate and distal portions, the proximal portion being attached to the drive shaft socket, the intermediate portion being disposed primarily within the catheter, and the distal portion extending distally from the catheter and having a tissue removal implement;

b. a rotatable, radially expandable prime mover coupling connected to a prime mover for rotation therewith, the prime mover being carried by a prime mover carriage and the prime mover coupling including a radially expandable portion;

the drive shaft socket being sized to receive a length of the radially expandable portion of the prime mover coupling therein such that the radially expandable portion of the prime mover coupling does not effectively engage an interior of the drive shaft socket when the coupling is not rotating, but the radially expandable portion of the prime mover coupling radially expands to effectively engage the socket upon sufficiently rapid rotation of the prime mover, causing the socket and the drive shaft to rotate together with the prime mover coupling and the prime mover, whereby when the prime mover is not rotating, the drive shaft is disconnected from the prime mover, thereby permitting the exchangeable drive shaft cartridge to be replaced by another exchangeable drive shaft cartridge.

146. The rotational atherectomy device of claim 134, claim 135, claim 143 or claim 145 wherein the prime mover coupling comprises a coupling base and at least two flexible pins, each pin being anchored adjacent a proximal end to the coupling base and having a distal end which is free to deflect radially outwardly to engage the interior of the drive shaft socket when the prime mover is rotated.

147. The rotational atherectomy device of claim 146 further comprising a coupling shield carried by the prime mover coupling, the coupling shield restricting outward deflection of the distal ends of the pins upon rotation of the prime mover when the distal ends of the pins are not properly received within the drive shaft socket.

148. The rotational atherectomy device of claim 138, claim 139, claim 140, claim 141, claim 143, or claim 145 further comprising a handle which includes a distal portion adapted to releasably hold the drive shaft cartridge, a proximal portion carrying the prime mover carriage, and an elongated rod connecting the distal and proximal portions of the handle to one another.

149. The rotational atherectomy device of claim 134, claim 135 or claim 145 further comprising a flexible fluid supply tubing attached to the exchangeable drive shaft cartridge and in fluid communication with a drive shaft lumen of the drive shaft cartridge.

150. The rotational atherectomy device of claim 149 wherein the drive shaft lumen includes a reduced inner diameter segment, the reduced inner diameter segment being positioned proximally of where the fluid supply tubing delivers fluid to the drive shaft lumen, thereby reducing flow of fluid proximally along the drive shaft lumen.

151. A system for releasably connecting a drive shaft to a prime mover comprising:
  a) an exchangeable drive shaft cartridge comprising a rotatable drive shaft socket carried by a drive shaft carriage and a rotatable drive shaft having a proximal portion attached to the drive shaft socket;
  b) a rotatable, radially expandable prime mover coupling connected to a prime mover for rotation therewith, the prime mover coupling comprising a coupling base and at least two flexible pins, each pin being anchored adjacent one end thereof to the coupling base and having another end which is free to deflect radially outwardly to engage the drive shaft socket when the prime mover is rotated;
the drive shaft socket being sized to receive free end portions of the pins of the prime mover coupling therein such that the pins do not contact the interior surface of the drive shaft socket when the coupling is not rotating, but the free end portions of the pins deflect into frictional engagement with the socket upon sufficiently rapid rotation of the prime mover, causing the socket and the drive shaft to rotate together with the prime mover coupling and the prime mover, whereby when the prime mover is not rotating, the drive shaft is disconnected from the prime mover, thereby permitting the exchangeable drive shaft cartridge to be replaced by another exchangeable drive shaft cartridge.

152. The system of claim 151 wherein the coupling base includes at least one abutment spaced radially outwardly from each pin when the coupling base is not rotated and limiting outward deflection of an intermediate point along the length of the pin when the prime mover is rotated.

153. A method of removing tissue, comprising:
  a) providing a tissue removal device which comprises:
    i) an exchangeable drive shaft cartridge comprising a rotatable drive shaft socket carried by a drive shaft carriage; a longitudinally extendable tube extending distally from the drive shaft carriage; an elongated catheter having a proximal end portion which is operatively connected to a distal end portion of the longitudinally extendable tube; and a rotatable flexible drive shaft having proximal, intermediate and distal portions, the proximal portion being attached to the drive shaft socket, the intermediate portion being disposed primarily within the tube and the catheter, and the distal portion extending distally from the catheter and having a tissue removal implement; and
    ii) a rotatable, radially expandable prime mover coupling carried by a prime mover carriage and connected to a prime mover for rotation therewith;
  b) positioning a length of the prime mover coupling within the drive shaft socket such that the prime mover coupling does not effectively engage an interior surface of the drive shaft socket;
  c) rotating the prime mover and the prime mover coupling at a speed sufficient to cause the prime mover coupling to radially expand to effectively engage the socket, causing the socket, the drive shaft and the tissue removal implement to rotate together with the prime mover coupling and the prime mover;
  d) contacting tissue with the tissue removal implement;
  e) removing tissue with the tissue removal implement; and
  f) stopping rotation of the prime mover, thereby disconnecting the drive shaft from the prime mover.

154. The method of claim 153 further comprising, after stopping rotation of the prime mover, replacing the exchangeable drive shaft cartridge with another exchangeable drive shaft cartridge.

155. A method of removing tissue, comprising:
  a) providing a tissue removal device which comprises:
    i) an exchangeable drive shaft cartridge comprising a rotatable drive shaft socket carried by a drive shaft carriage; a longitudinally extendable tube extending distally from the drive shaft carriage; an elongated catheter having a proximal end portion which is operatively connected to a distal end portion of the longitudinally extendable tube; and a rotatable flexible drive shaft having proximal, intermediate and distal portions, the proximal portion being attached to the drive shaft socket, the intermediate portion being disposed primarily within the tube and the catheter, and the distal portion extending distally from the catheter and having a tissue removal implement; and
    ii) a rotatable, radially expandable prime mover coupling carried by a prime mover carriage and connected to a prime mover for rotation therewith;
  b) positioning a length of the prime mover coupling within the drive shaft socket such that the prime mover coupling does not effectively engage an interior surface of the drive shaft socket;
  c) advancing the flexible drive shaft and the catheter over a guide wire into a body passageway of interest;
  d) thereafter, rotating the prime mover coupling at a speed sufficient to cause it to radially expand to effectively engage the socket, causing the socket and the drive shaft to rotate together with the prime mover coupling and the prime mover;

e) advancing the rotating flexible drive shaft and its tissue removal implement against tissue;

f) removing tissue with the tissue removal implement; and g) stopping rotation of the prime mover, thereby disconnecting the drive shaft from the prime mover.

156. The method of claim 155 further comprising, after stopping rotation of the prime mover, replacing the exchangeable drive shaft cartridge with another exchangeable drive shaft cartridge.

157. The method of 156 further comprising, after replacing the exchangeable drive shaft cartridge, repeating steps b–f.

* * * * *